US012616773B2

(12) United States Patent
Yang et al.

(10) Patent No.: US 12,616,773 B2
(45) Date of Patent: May 5, 2026

(54) BIOADHESIVE COMPOSITIONS AND METHODS OF MAKING THE SAME

(71) Applicant: THE PENN STATE RESEARCH FOUNDATION, University Park, PA (US)

(72) Inventors: Jian Yang, State College, PA (US); Jinshan Guo, Mason, OH (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 644 days.

(21) Appl. No.: 17/788,925

(22) PCT Filed: Dec. 18, 2020

(86) PCT No.: PCT/US2020/065951
§ 371 (c)(1),
(2) Date: Jun. 24, 2022

(87) PCT Pub. No.: WO2021/133663
PCT Pub. Date: Jul. 1, 2021

(65) Prior Publication Data

US 2023/0087713 A1 Mar. 23, 2023

Related U.S. Application Data

(60) Provisional application No. 63/028,691, filed on May 22, 2020, provisional application No. 62/953,401, filed on Dec. 24, 2019.

(51) Int. Cl.

| | |
|---|---|
| ***A61L 24/00*** | (2006.01) |
| ***A61L 27/52*** | (2006.01) |
| ***A61L 27/54*** | (2006.01) |
| ***C08L 67/02*** | (2006.01) |

(52) U.S. Cl.
CPC ....... *A61L 24/0031* (2013.01); *A61L 24/0015* (2013.01); *A61L 27/52* (2013.01); *A61L 27/54* (2013.01); *C08L 67/02* (2013.01); *A61L 2300/406* (2013.01); *A61L 2300/414* (2013.01)

(58) Field of Classification Search
CPC .. A61L 24/0031; A61L 24/0015; A61L 27/52; A61L 27/54; A61L 2300/406; A61L 2300/414; C08L 67/02
See application file for complete search history.

(56) References Cited

U.S. PATENT DOCUMENTS

| | | | |
|---|---|---|---|
| 7,264,823 | B2 | 9/2007 | Beckman et al. |
| 2013/0217790 | A1 | 8/2013 | Yang et al. |
| 2016/0199541 | A1 | 7/2016 | Yang et al. |
| 2017/0080125 | A1 | 3/2017 | Yang |
| 2017/0202998 | A1 | 7/2017 | Yang et al. |
| 2020/0140607 | A1 | 5/2020 | Yang et al. |

FOREIGN PATENT DOCUMENTS

| | | | |
|---|---|---|---|
| JP | 2019-504922 | A | 2/2019 |
| WO | 2018/227151 | | 12/2018 |
| WO | 2018/227151 | A1 | 12/2018 |
| WO | 2019/070561 | A1 | 4/2019 |

OTHER PUBLICATIONS

D.A. Hickman, C.L. Pawlowski, U.D.S. Sekhon, J. Marks, AS Biomaterials and advanced technologies for hemostatic management of bleeding, Adv. Mater. 30 (4) (2018) 1700859-1700899.
D. Xie, J. Guo, M.R. Mehdizadeh, R.T. Tran, R. Chen, D. Sun, G. Qian, D. Jin, X. Bai, J. Yang, Development of injectable citrate-based bioadhesive bone implants, J. Mater. Chem. B. 3 (2015) 387-398.
A.P. Duarte, J.F. Coelho, J.C. Bordado, M.T. Cidade, M.H. Gil, Surgical adhesives: Systematic review of the main types and development forecast, Prog. Polym. Sci. 37 (8) (2012) 1031-1050.
J. Li, A.D. Celiz, J. Yang, Q. Yang, I. Wamala, W. Whyte, B.R. Seo, N.V. Vasilyev, J.J. Vlassak, Z. Suo, D.J. Mooney, Tough adhesives for diverse wet surfaces, Science 357 (6349) (2017) 378-381.
J. Guo, W. Sun, J.P. Kim, X. Lu, Q. Li, M. Lin, O. Mrowczynski, E. B. Rizk, J. Cheng, G. Qian, J. Yang, Development of tannin-inspired antimicrobial bioadhesives, Acta Biomater. 72 (2018) 35-44 .
N. Annabi, K. Yue, A. Tamayol, A. Khademhosseini, Elastic sealants for surgical applications, Eur. J. Pharm. Biopharm. 95 (2015) 27-39.
T. Fattahi, M. Mohan, G.T. Caldwell, Clinical applications of fibrin sealants, J. Oral. Maxillofac. Surg. 62 (2) (2004) 218-224.
J.L. Lim, W.K. Lee, Enhanced biocompatibility and adhesive properties by aromatic amino acid-modified allyl 2-cyanoacrylate-based bio-glue, Colloid. Surface B. 122 (2014) 669-673.
J.R. Dusick, C.A. Mattozo, F. Esposito, D.F. Kelly, BioGlue for prevention of postoperative cerebrospinal fluid leaks in transsphenoidal surgery: A case series, Surg. Neurol. 66 (2006) 371-376.
W. Furst, A. Banerjee, Conflict of interest disclosure relating to Release of glutaraldehyde from an albumin-glutaraldehyde tissue adhesive causes significant in vitro and in vivo toxicity, Ann. Thorac. Surg. 79 (2005) 1522-1528.
PJM Bouten, M. Zonjee, J. Bender, S.T.K. Yauw, H. van Goor, JCM van Hest, R. Hoogenboom, The chemistry of tissue adhesive materials, Prog. Polym. Sci. 39 (7) (2014) 1375-1405.
G. Lee, C.K. Lee, M. Bynevelt, DuraSeal-hematoma: concealed hematoma causing spinal cord compression, Spine 35 (25) (2010) E1522-E1524.
R. Wang, J. Li, W. Chen, T. Xu, S. Yun, Z. Xu, Z. Xu, T. Sato, B. Chi, H. Xu, A biomimetic mussel-inspired e-poly-L-lysine hydrogel with robust tissue-anchor and anti-infection capacity, Adv. Funct. Mater. 27 (8) (2017) 1604894-1604907.
M. Mehdizadeh, H. Weng, D. Gyawali, L. Tang, J. Yang, Injectable citrate-based mussel-inspired tissue bioadhesives with high wet strength for sutureless wound closure, Biomaterials 33 (32) (2012) 7972-7983.

(Continued)

*Primary Examiner* — Shirley V Gembeh
(74) *Attorney, Agent, or Firm* — Meunier Carlin & Curfman LLC

(57) ABSTRACT

Disclosed herein are citrate-based mussel-inspired bioadhesives and methods of making and using the same. Also disclosed herein are methods of treating wounds.

19 Claims, 12 Drawing Sheets

(56) References Cited

OTHER PUBLICATIONS

J. Guo, W. Wang, J. Hu, D. Xie, E. Gerhard, M. Nisic, D. Shan, G. Qian, S. Zheng, J. Yang, Synthesis and characterization of antibacterial and anti-fungal citrate-based mussel-inspired bioadhesives, Biomaterials 85 (2016) 204-217.

J. Guo, G.B. Kim, D. Shan, J.P. Kim, J. Hu, W. Wang, F.G. Hamad, G. Qian, E.B. Rizk, J. Yang, Click chemistry improved wet adhesion strength of mussel-inspired citrate-based antimicrobial bioadhesives, Biomaterials 112 (2017) 275-286.

Y. Liu, H. Meng, Z. Qian, N. Fan, W. Choi, F. Zhao, B.P. Lee, A moldable nanocomposite hydrogel composed of a mussel-inspired polymer and a nanosilicate as a fit-to-shape tissue sealant, Angew. Chem. Int. Ed. 56 (15) (2017) 4224-4228.

Z. Gu, S. Li, F. Zhang, S. Wang, Understanding surface adhesion in nature: A peeling model, Adv. Sci. 3 (7) (2016) 1500327-1500340.

D.G. Barrett, G.G. Bushnell, P.B. Messersmith, Mechanically robust, negative-swelling, mussel-inspired tissue adhesives, Adv. Healthcare Mater. 2 (5) (2013) 745-755.

C. Ma, X. Tian, J.P. Kim, D. Xie, X. Ao, D. Shan, Q. Lin, M. R. Hudock, X. Bai, J. Yang, Citrate-based materials fuel human stem cells by metabonegenic regulation, Proc. Natl. Acad. Sci. U. S. A. 115 (50) (2018) E11741-E11750.

D. Shan, S.- R. Kothapalli, D.J. Ravnic, E. Gerhard, J.P. Kim, J. Guo, C. Ma, J. Guo, L. Gui, L. Sun, D. Lu, J. Yang, Development of citrate-based dual-imaging enabled biodegradable electroactive polymers, Adv. Funct. Mater. 28 (34) (2018) 1801787.

J. Guo, Z. Xie, R. T. Tran, D. Xie, D. Jin, X. Bai, J. Yang, Click chemistry plays a dual role in biodegradable polymer design. Adv. Mater. 26 (12) (2014) 1906-1911.

K. Sannier, A. Dompmartin, J. Theron, D. Labbe, M.T. Barrellier, R. Leroyer, P. Toure, D. Leroy, A new sclerosing agent in the treatment of venous malformations. Study on 23 cases, Interv. Neuroradiol. 10 (2) (2004) 113-127.

M.M. Smith, M.P. Lin, R.V. Hovsepian, D. Wood, T. Nguyen, G.R.D. Evans, G.A. Wirth, Postoperative seroma formation after abdominoplasty with placement of continuous infusion local anesthetic pain pump, Can. J. Plast. Surg. 17 (4) (2009) 127-129.

L. Cardenas-Camarena, L.E. Gonzalez, Large-volume liposuction and extensive abdominoplasty: a feasible alternative for improving body shape, Plast. Reconstr. Surg. 102 (5) (1998) 1698-1707.

D.J. Hickey, B. Ercan, L. Sun, T.J. Webster, Adding MgO nanoparticles to hydroxyapatite-PLLA nanocomposites for improved bone tissue engineering applications, Acta Biomater. 14 (2015) 175-184.

O. Yamamotoa, T. Ohira, K. Alvarez, M. Fukuda, Antibacterial characteristics of CaC03-MgO composites, Mater. Sci. Eng. B. 173 (1-3) (2010) 208-212.

Y. Rao, W. Wang, F. Tan, Y. Cai, J. Lu, X. Qiao, Influence of different ions doping on the antibacterial properties of MgO nanopowders, Appl. Surf. Sci. 284 (2013) 726-731.

S. Sakai, K. Hirose, K. Taguchi, Y. Ogushi, K. Kawakami, An injectable, in situ enzymatically gellable, gelatin derivative for drug delivery and tissue engineering, Biomaterials 30 (20) (2009) 3371-3377.

B.P. Lee, J.L. Dalsin, P.B. Messersmith, Synthesis and gelation of DOPA-modified polyethylene glycol) hydrogels, Biomacromolecules 3 (5) (2002) 1038-1047. L.C. Su, Z. Xie, Y. Zhang, K.T. Nguyen, J. Yang, Study on the Antimicrobial Properties of Citrate-Based Biodegradable Polymers, Front. Bioeng. Biotechnol. 2 (2014) 23.

NA. Vasil'eva, L.M. Plyasova, G.V. Odegova, Defective magnesium oxides with oxygen-containing anion fragments incorporated in the oxide structure, Kinet. Catal. 50 (6) (2009) 816-818.

Z.-X. Tang, B.-F. Lv, MgO nanoparticles as antibacterial agent: preparation and activity, Braz. J. Eng Chem. 31 (3) (2014) 591-601.

M. Mittal, M.R. Siddiqui, K. Tran, S.P. Reddy, A.B. Malik, Reactive oxygen species in inflammation and tissue injury. Antioxid. Redox Sign. 20 (2014) 1126-1167.

S. Xu, A.D. Chisholml , C. Elegans epidermal wound induces a mitochondrial ROS burst that promotes wound repair. Dev. Cell 31 (2014) 48-60.

D. Gyawali, P. Nair, Y. Zhang, R.T. Tran, C. Zhang, M. Samchukov, M. Makarov, H.K. Kim, J. Yang, Citric acid-derived in situ crosslinkable biodegradable polymers for cell delivery, Biomaterials 31 (34) (2010) 9092-9105.

F. Sekiya, M, Yoshida, T. Yamashita, Magnesium(II) is a crucial constituent of the blood coagulation cascade. Potentiation of coagulant activities of factor IX by $Mg^{2+}$ions, J. Biol. Chem. 271 (15) (1996) 8541-8544.

AMHP van den Besselaar, Magnesium and manganese ions accelerate tissue factor-induced coagulation independently of factor IX, Blood Coagul. Fibrinolysis. 13 (1) (2002) 19-23.

E.M. Liotta, S. Prabhakaran, R.S. Sangha, R.A. Bush, A.E. Long, S.A. Trevick, M.B. Potts, B.S. Jahromi, M. Kim, E.M. Manno, F.A. Sorond, A.M. Naidech, M.B. Maas, Magnesium, hemostasis, and outcomes in patients with intracerebral hemorrhage, Neurology 89 (8) (2017) 813-819.

English translation of Japanese Office Action issued in JP2022-538990, mailed Dec. 24, 2025.

International Searching Authority (ISA/US). International Search Report and Written Opinion, issued in PCT Application No. PCT/US2020/065951 on Apr. 23, 2021. 16 pages.

Extended European Search Report issued in EP 20904347.0, mailed Dec. 19, 2023.

Office Action issued in Canadian Application No. 3163006, mailed Jan. 19, 2024.

First Examination Report issued in Australian Application No. 2020412597, dated Mar. 3, 2026.

Citric acid (CA)

PEG-PPG-PEG

Dopamine iC-EPE Pre-polymer $R_1$ = H or polymer chain

A = -O- or -NH- $R_2$ = H or polymer chain or

BIOADHESIVE COMPOSITIONS AND METHODS OF MAKING THE SAME

CROSS-REFERENCE TO RELATED APPLICATIONS

This application is a national stage application filed under 35 U.S.C. § 371 of PCT/US2020/065951, filed Dec. 18, 2020, which claims the benefit of U.S. Provisional Application No. 62/953,401, filed Dec. 24, 2019, and U.S. Provisional Application No. 63/028,691, filed May 22, 2020, the contents of which are incorporated herein by reference in their entireties.

TECHNICAL FIELD

The present disclosure generally relates to bioadhesive compositions that can be used as wound closing or bone filling compositions and methods of making the same.

BACKGROUND

Tissue (bio)adhesives have attracted increased attention in recent years due to their wide applicability in the biomedical field, including wound closure, hemostat, tissue sealing, implant fixation, and drug delivery. Commercially available biologically-derived fibrin glue (Tisseel), which is mainly composed of concentrated fibrinogen, thrombin, and calcium chloride, thus duplicating the last stage of biological coagulation cascade, is the most widely used tissue adhesive due to its fast curing and biodegradability and often considered as the gold standard of tissue adhesives. However, there are also limitations, such as poor wet tissue adhesion, thus reducing its efficacy for applications where strong tissue adhesion is required.

Other adhesives, for example, cyanoacrylate adhesives, offer advantages such as ease of use, strong adhesion to tissue. However, the applications of cyanoacrylates have also been mainly limited to topical uses due to concerns such as slow degradation, exothermic polymerization, and toxicity of degradation products.

Additional adhesives, such as albumin-glutaraldehyde bioadhesives (BioGlue), are clinically used in cardiac and vascular repair and pulmonary repair, but it also brings concern on their toxicity due to the use of a toxic crosslinking component. Urethane-based (TissuGlu) tissue adhesives may offer strong tissue adhesion and fast curing, but they may suffer from vigorous exothermic chemical reactions and slow degradation. Poly(ethylene glycol) (PEG)-based bioadhesives, such as CoSeal and DuraSeal, have been used as tissue sealants for some applications, but concerns on their large swelling ratios and rapid degradation were believed to possibly trigger significant post-surgical complications such as rapid leakage, compression on the nearby nerve ends, and the formation of a hematoma.

Accordingly, a need still exists for alternative bioadhesive compositions that have superior biocompatibility and strong wet tissue adhesion strength. Still further, a need exists for bioadhesives that are not toxic, have acceptable swelling ratios, and the desired degradation rate. Also, there are needs for methods of making such compositions. These needs and other needs are at least partially satisfied by the present disclosure.

SUMMARY

The present invention is directed to a crosslinked composition comprising: a) a polymerization product of one or more monomers of Formula (I) and one or more units of a block copolymer comprising one or more monomers of Formula (II) and/or Formula (II'), one or more monomers of Formula (III), and/or optionally one or more compounds of Formula (IV):

(I)

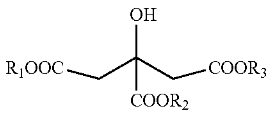

(II)

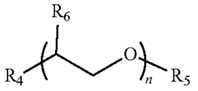

or (II')

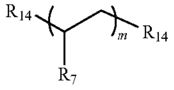

(III)

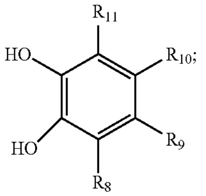

(IV)

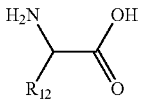

wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; $R_6$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m are, independently, integers from 1 to 20; $R_{12}$ is an amino acid side chain; $R_{14}$ is —OH or —$NH_2$; and wherein the polymerization product does not comprise metal cations b) a first crosslinking initiator having a formula $A_{b''}O_{a'}$, wherein A is a monovalent, divalent, or trivalent metallic cation and wherein a' and b" are dependent on the valency of A; wherein A is not a transition metal cation and wherein the first crosslinking initiator is configured to crosslink the reaction product to form the crosslinked composition; wherein the crosslinked composition is a polymer network having at least one crosslink comprising two catechol moieties directly and covalently coupled to each other; and wherein the crosslinked composition is a hydrogel or an organogel and is an adhesive composition.

In still further aspects, the composition as disclosed herein comprises aspects where $R_1$, $R_2$, and $R_3$ are, independently, selected from hydrogen, $—CH_3$ group, or $—CH_2CH_3$ group; $R_4$ is selected from hydrogen, a hydroxyl group, $—NH_2$, $—OCH_3$, $—OCH_2CH_3$, $—CH_3$, $—CH_2CH_3$ group; a $C_3$ to $C_{22}$ alkyl or alkenyl group, $—CH_2CH_2OH$, or $—CH_2CH_2NH_2$; $R_5$ is hydrogen, a hydroxyl group, $—NH_2$, $—CH_3$, or $—CH_2CH_3$ group, a $C_3$ to $C_{22}$ alkyl or alkenyl group, $—CH_2CH_2OH$, or $—CH_2CH_2NH_2$; $R_6$ is selected from hydrogen, $—CH_3$ group, or $—CH_2CH_3$ group; $—CH_2CH_2OH$, or $—CH_2CH_2NH_2$; $R_7$ is selected from hydrogen or $—CH_3$ group; $R_8$, $R_9$, $R_{10}$, and $R_{11}$ are, independently, selected from hydrogen, $—CH_2(CH_2)_xNH_2$, $—CH_2(CHR_{13})NH_2$, or $—CH_2(CH_2)_xCOOH$ groups; and wherein at least one of $R_8$, $R_9$, $R_{10}$, and $R_{11}$ is not hydrogen; $R_{13}$ is $—COOH$ or $—(CH_2)_yCOOH$ group; n and m, are independently integers from 1 to 20; x is an integer from 0 to 20; and y is an integer from 1 to 20.

In still further aspects, the first crosslinking initiator simultaneously behaves as a first filler. Also disclosed herein aspects wherein the composition further comprises a second crosslinking initiator that is different from the first crosslinking initiator. In still further aspects, the second crosslinking initiator can comprise sodium periodate, silver nitrate, or ferric chloride, or any combination thereof.

Also disclosed are aspects directed to a crosslinked composition formed by a) forming a polymerization product by reacting a polycarboxylic acid of one or more monomers of Formula (I) with a block copolymer comprising one or more monomers of Formula (II), and/or Formula (II'), one or more monomers of Formula (III), and/or optionally one or more compounds of Formula (IV):

(I)

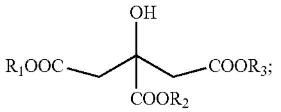

(II)

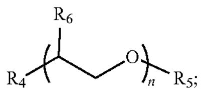

(II')

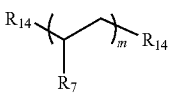

-continued (III)

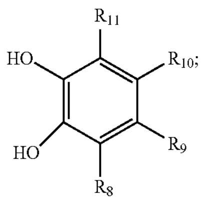

(IV)

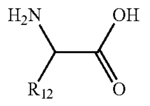

Wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; $R_6$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m, are independently integers from 1 to 20; $R_{12}$ is an amino acid side chain; $R_{14}$ is —OH or $—NH_2$; and wherein the polymerization product does not comprise metal cations; b) crosslinking the polymerization product with a first crosslinking initiator having a formula $A_{b''}O_{a'}$, wherein A is a monovalent, divalent, or trivalent metallic cation and wherein a' and b" are defined by the valency of A; wherein A is not a transition metal cation; wherein the crosslinked composition is a polymer network having at least one crosslink comprising two catechol moieties directly and covalently coupled to each other; wherein the crosslinked composition is a hydrogel or organogel and is an adhesive composition.

Also disclosed herein are methods of making the disclosed compositions. In certain aspects, disclosed herein is a method of making a composition, comprising: a) reacting a polycarboxylic acid of one or more monomers of Formula (I)

(I)

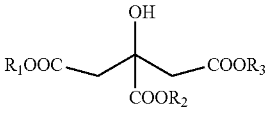

with one or more units of a block copolymer comprising one or more monomers of Formula (II) and (II'), (II)

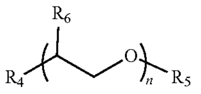

or (II')

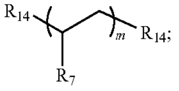

with a compound of one or more monomers of Formula (III)

(III)

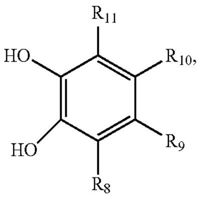

and optionally
with one or more compounds of Formula (IV)

(IV)

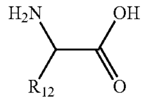

at conditions effective to form a prepolymer composition configured to be crosslinked; wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; $R_6$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m, are independently integers from 1 to 20; $R_{12}$ is an amino acid side chain; $R_{14}$ is —OH or —$NH_2$; and wherein the polymerization product does not comprise metal cations; b) adding a first crosslinking initiator to the prepolymer composition; wherein the first crosslinking initiator has a formula $A_bB_a$, wherein A is a monovalent, divalent, or trivalent metallic cation and B is an anion, and wherein a and b are defined by the valency of A and B; wherein A is not a transition metal cation and c) crosslinking the prepolymer composition to form a crosslinked composition comprising a polymer network, wherein at least one crosslink in the crosslinked polymer comprises two catechol moieties directly and covalently coupled to each other; and wherein the crosslinked composition is a hydrogel or organogel and is adhesive.

Also disclosed herein are aspects describing a method of adhering a biological tissue, comprising: a) disposing the composition as described herein between a first portion of biological tissue and a second portion of biological tissue; and b) contacting the first portion of biological tissue with the second portion of biological tissue.

Further, in certain aspects, disclosed is a method of treating disease, comprising disposing the composition as described herein within the biological body, wherein the at least one pharmaceutically active component is active towards the disease and is configured to be released into the biological body at a predetermined time.

Also is disclosed is a method of promoting a biological tissue growth comprising providing a scaffold comprising the composition as described herein and disposing the scaffold in a tissue growth media.

Also disclosed herein is a kit for adhering a biological tissue comprising any of the disclosed herein crosslinked compositions.

Also disclosed herein is a method of delivering at least one pharmaceutically active component in an efficient amount wherein the method comprises: a) incorporating the at least one pharmaceutically active component into a composition comprising: i) a polymerization product of one or more monomers of Formula (I) and one or more units of a block copolymer comprising one or more monomers of Formula (II), and/or Formula (II'), one or more monomers of Formula (III), and/or optionally one or more compounds of Formula (IV):

(I)

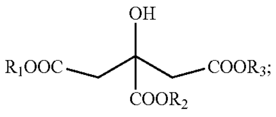

(II)

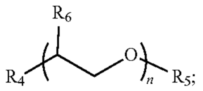

-continued (II')

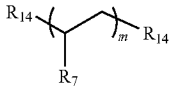

(III)

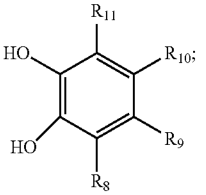

(IV)

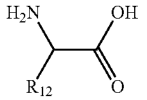

Wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; $R_6$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m, are independently integers from 1 to 20; $R_{12}$ is an amino acid side chain; $R_{14}$ is —OH or —$NH_2$; and wherein the polymerization product does not comprise metal cations; and ii) a first crosslinking initiator having a formula $A_{b''}O_{a'}$, wherein A is a monovalent, divalent, or trivalent metallic cation and wherein a' and b'' are dependent on the valency of A; wherein A is not a transition metal cation and wherein the first crosslinking initiator is configured to crosslink the reaction product to form the crosslinked composition; and wherein the crosslinked composition is a polymer network having at least one crosslink comprising two catechol moieties directly and covalently coupled to each other; wherein the crosslinked composition is a hydrogel or an organogel and is an adhesive composition; b) releasing the at least one pharmaceutical agent into a biological body at a predetermined time.

Additional aspects of the disclosure will be set forth, in part, in the detailed description, figures, and claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF DRAWINGS

FIG. 1A—Synthesis of iC-EPE (injectable citrate-based mussel-inspired bioadhesives (iCMBAs, iC) made with PEG-PPG-PEG (EPE) diol) prepolymers; FIG. 1B—Magnesium oxide (MgO) serves both as a crosslinker and a composite filler to enable a wide tunability on the crosslinking time and the adhesion strengths of the resultant iC-EPE/MgO hydrogels that hold great potential for a myriad of surgical applications such as wound closure and healing.

(FIG. 9A) Gross observation of skin wounds treated with suture and W10 at different time points (5 min, 7 days and 28 days; the images of the reverse side of the harvested skin samples near the treated wounds at day 28 are also shown on the right); H&E staining images (FIG. 9B) and the infiltrated cell densities in the incision areas (FIG. 9C) of the sutured group and the W10 groups; Images of CD11b immunohistochemical staining (FIG. 9D) and the numbers of CD11 b positive cells around the wound areas of the sutured group and W10 group (FIG. 9E); Masson trichrome staining images (FIG. 9F) and the collagen densities in the wound areas of the sutured group and W10 group (FIG. 9G). $^{\#}p>0.05$, $*p<0.05$, $**p<0.01$.

DETAILED DESCRIPTION

Figure 1A:
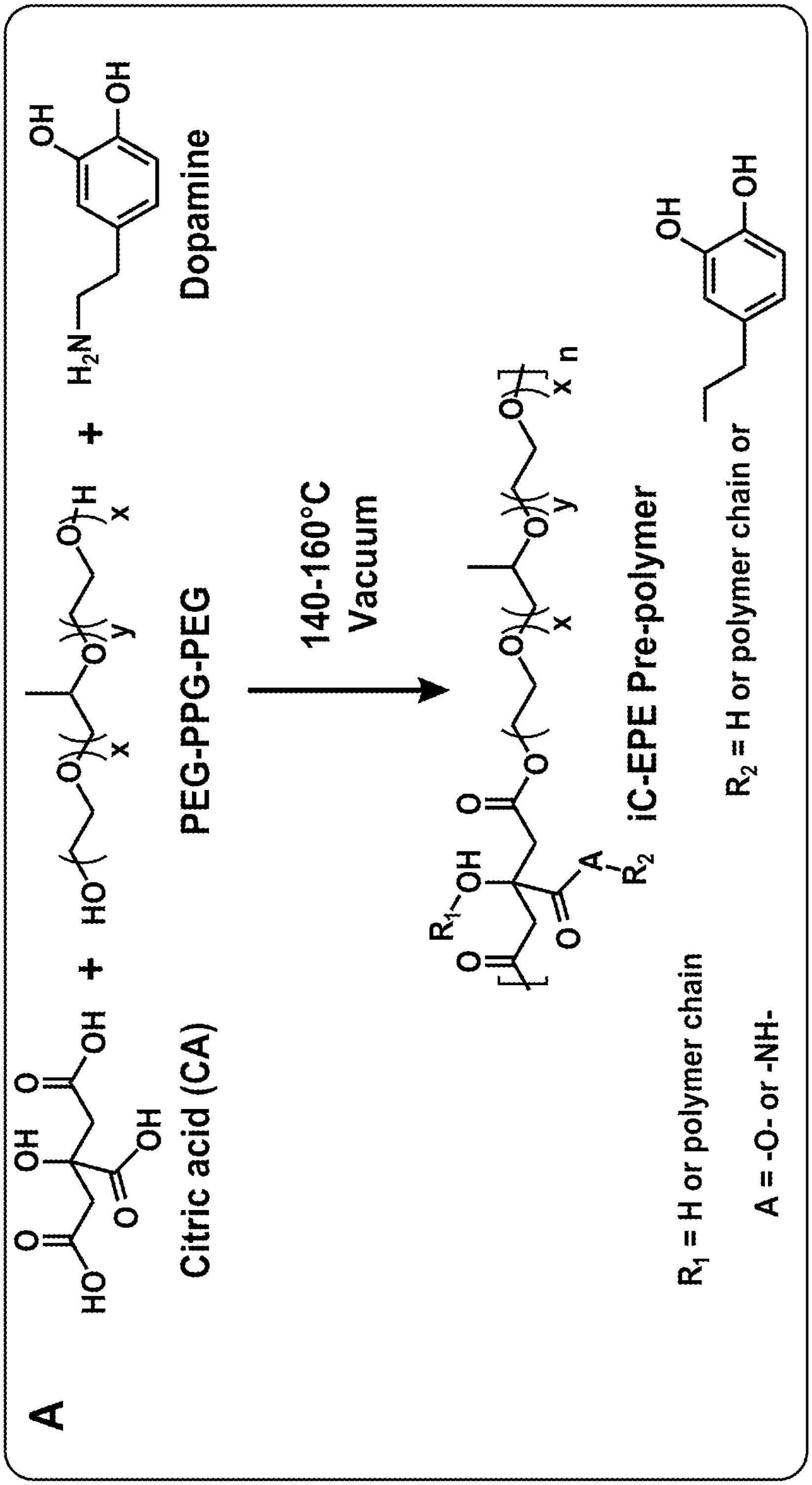
FIGS. 1A-1B depict the following.

The present invention can be understood more readily by reference to the following detailed description, examples, drawings, and claims, and their previous and following description. However, before the present articles, systems, and/or methods are disclosed and described, it is to be understood that this invention is not limited to the specific or exemplary aspects of articles, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein while still obtaining the beneficial results of the present invention. It will also be apparent that some of the desired benefits of the present invention can be obtained by selecting some of the features of the present invention without utilizing other features. Accordingly, those of ordinary skill in the pertinent art will recognize that many modifications and adaptations to the present invention are possible and may even be desirable in certain circumstances and are a part of the present invention. Thus, the following description is again provided as illustrative of the principles of the present invention and not in limitation thereof.

Definitions

As used herein, the terms "optional" or "optionally" means that the subsequently described event or circumstance can or cannot occur and that the description includes instances where said event or circumstance occurs and instances where it does not.

It is appreciated that certain features of the disclosure, which are, for clarity, described in the context of separate aspects, can also be provided in combination in a single aspect. Conversely, various features of the disclosure, which are, for brevity, described in the context of a single aspect, can also be provided separately or in any suitable subcombination.

As used in the description and the appended claims, the singular forms "a," "an," and "the" include plural referents unless the context clearly dictates otherwise. Thus, for example, a reference to "a functional group" includes two or more such functional groups, reference to "a composition" includes two or more such compositions and the like.

It is also to be understood that the terminology used herein is for the purpose of describing particular aspects only and is not intended to be limiting. As used in the specification and in the claims, the term "comprising" can include the aspects "consisting of" and "consisting essentially of." Unless defined otherwise, all technical and scientific terms used herein have the same meaning as commonly understood by one of ordinary skill in the art to which this invention belongs. In this specification and in the claims, which follow, reference will be made to a number of terms that shall be defined herein.

For the terms "for example" and "such as," and grammatical equivalences thereof, the phrase "and without limitation" is understood to follow unless explicitly stated otherwise.

As used herein, the term "substituted" means that a hydrogen atom is removed and replaced by a substituent. It is contemplated to include all permissible substituents of organic compounds. As used herein, the phrase "optionally substituted" means unsubstituted or substituted. It is to be understood that substitution at a given atom is limited by valency. In a broad aspect, the permissible substituents include acyclic and cyclic, branched and unbranched, carbocyclic and heterocyclic, and aromatic and nonaromatic substituents of organic compounds.

Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with a permitted valence of the substituted atom and the substituent and that the substitution results in a stable compound, e.g., a compound that does not spontaneously undergo transformation such as by rearrangement, cyclization, elimination, etc. In still further aspects, it is understood that when the disclosure describes a group being substituted, it means that the group is substituted with one or more (i.e., 1, 2, 3, 4, or 5) groups as allowed by valence selected from alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The expressions "ambient temperature" and "room temperature" as used herein are understood in the art and refer generally to a temperature, e.g., a reaction temperature, that is about the temperature of the room in which the reaction is carried out, for example, a temperature from about 20° C. to about 30° C.

The term "aliphatic" as used herein refers to a nonaromatic hydrocarbon group and includes branched and unbranched, alkyl, alkenyl, or alkynyl groups. As used herein, the term "$C_n$-$C_m$ alkyl," employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, teri-butyl, isobutyl, sec-butyl; higher homologs such as 2-methyl-I-butyl, n-pentyl, 3-pentyl, n-hexyl, 1,2,2-trimethylpropyl, heptyl, octyl, nonyl, decyl, dodecyl, tetradecyl, hexadecyl, eicosyl, tetracosyl, and the like. The alkyl group can also be substituted or unsubstituted. Throughout the specification, the term "alkyl" is generally used to refer to both unsubstituted alkyl groups and substituted alkyl groups; however, substituted alkyl groups are also specifically referred to herein by identifying the specific substituent(s) on the alkyl group. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below and the like. When "alkyl" is used in one instance, and a specific term such as "alkylalcohol" is used in another, it is not meant to imply that the term "alkyl" does not also refer to specific terms such as "alkylalcohol" and the like.

As used herein, "$C_n$-$C_m$ alkenyl" refers to an alkyl group having one or more double carbon-carbon bonds and having n to m carbons. Examples of alkenyl groups include, but are not limited to, ethenyl, n-propenyl, isopropenyl, n-butenyl, seobutenyl, and the like. In various aspects, the alkenyl moiety contains 2 to 6, 2 to 4, or 2 to 3 carbon atoms. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, thiol, or phosphonyl, as described below.

As used herein, "$C_n$-$C_m$ alkynyl" refers to an alkyl group having one or more triple carbon-carbon bonds and having n to m carbons. Exemplary alkynyl groups include, but are not limited to, ethynyl, propyn-1-yl, propyn-2-yl, and the like. In various aspects, the alkynyl moiety contains 2 to 6, 2 to 4, or 2 to 3 carbon atoms. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described below.

As used herein, the term "$C_n$-$C_m$ alkylene," employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In various aspects, the alkylene moiety contains to 6, 2 to 4, 2 to 3, 1 to 6, 1 to 4, or 1 to 2 carbon atoms.

As used herein, the term "$C_n$-$C_m$ alkoxy," employed alone or in combination with other terms, refers to a group of formula —O-alkyl, wherein the alkyl group has n to m carbons. Example of alkoxy groups includes methoxy, ethoxy, propoxy (e.g., w-propoxy and isopropoxy), teributoxy, and the like. In various aspects, the alkyl group has 1 to 6, 1 to 4, or 1 to 3 carbon atoms.

The terms "amine" or "amino" as used herein are represented by the formula —$NR^1R_2$, where $R^1$ and $R^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)$NR^1R_2$.

The term "aldehyde" as used herein is represented by the formula —C(O)H. Throughout this specification, the term "C(O)" or "CO" is a shorthand notation for C═O, which is also referred to herein as a "carbonyl."

The term "carboxylic acid" as used herein is represented by the formula —C(O) OH A "carboxylate" or "carboxyl" group as used herein is represented by the formula —C(O)$O^-$.

The term "ester" as used herein is represented by the formula —OC(O)$R^1$ or —C(O)O$R^1$, where $R^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $R^1OR^2$ where $R^1$ and $R^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $R^1C(O)R^2$, where $R^1$ and $R^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

As used herein, the term "thio" refers to a group of formula —SH.

As used herein, the term "$C_n$-$C_m$ alkylthio" refers to a group of formula —S— alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfmyl" refers to a group of formula —S(O)-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfonyl" refers to a group of formula —$S(O)_2$-alkyl, wherein the alkyl group has n to m carbon atoms. In various aspects, the alkyl group has 1 to 6, 1 to 4, or 1 to 3 carbon atoms.

As used herein, the term "carbamyl" to a group of formula —$C(O)NH_2$.

As used herein, the term "carbonyl," employed alone or in combination with other terms, refers to a —C(═O)— group, which may also be written as C(O).

As used herein, the term "carboxy" refers to a group of formula —C(O) OH.

As used herein, "halogen" refers to F, Cl, Br, or I. The term "hydroxyl" as used herein is represented by the formula —OH.

The term "cyano" as used herein is represented by the formula —CN. The term "nitro" as used herein is represented by the formula —$NO_2$.

The term "phosphonyl" is used herein to refer to the phospho-oxo group represented by the formula —P(O)$(OR^1)_2$, where $R^1$ can be absent, hydrogen, an alkyl, alkenyl, alkynyl, aryl, heteroaryl, cycloalkyl, or cycloalkenyl.

The term "silyl" as used herein is represented by the formula —$SiR^1R^2R^3$, where $R^1$, $R^2$, and $R^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —$S(O)_2R^1$, where $R^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

As used herein, "cycloalkyl" refers to nonaromatic cyclic hydrocarbons, including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example of cycloalkyl groups includes cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In various aspects, cycloalkyl is cyclopropyl, cyclobutyl, cyclopentyl, cyclohexyl, cyclopentyl, or adamantyl.

As used herein, "heterocycloalkyl" refers to nonaromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example of heterocycloalkyl groups includes pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or $S(O)_2$, etc.). The heterocycloalkyl group can be attached through a ring-forming carbon atom or a ring-forming heteroatom. In various aspects, the heterocycloalkyl group contains 0 to 3 double bonds.

The term "cycloalkenyl," as used herein, is a nonaromatic carbon-based ring composed of at least three carbon atoms and containing at least one double bond, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above and is included within the meaning of the term "cycloalkenyl," where at least one of the carbon atoms of the ring is substituted with a heteroatom such as, but not limited to, nitrogen, oxygen, sulfur, or phosphorus.

The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described herein.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In various aspects, aryl groups have from 6 to about 20 carbon atoms, from 6 to about 15 carbon atoms, or from 6 to about 10 carbon atoms. In various aspects, the aryl group is a substituted or unsubstituted phenyl.

As used herein, "heteroaryl" refers to a monocyclic or polycyclic aromatic heterocycle having at least one heteroatom ring member selected from sulfur, oxygen, phosphorus, and nitrogen. In various aspects, the heteroaryl ring has 1, 2, 3, or 4 heteroatom ring members independently selected from nitrogen, sulfur, and oxygen. In various aspects, any ring-forming N in a heteroaryl moiety can be an N-oxide. In various aspects, the heteroaryl has 5-10 ring atoms and 1, 2, 3 or 4 heteroatom ring members independently selected from nitrogen, sulfur, and oxygen. In various aspects, the heteroaryl has 5-6 ring atoms and 1 or 2 heteroatom ring members independently selected from nitrogen, sulfur, and oxygen. In various aspects, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl, and pyridazinyl.

The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described herein. The term "biaryl" is a specific type of aryl group and is included in the definition of aryl. Biaryl refers to two aryl groups that are bound together via a fused ring structure, as in naphthalene or are attached via one or more carbon-carbon bonds, as in biphenyl.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within the second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value and/or to "about" another particular value. When such a range is expressed, another aspect includes from the one particular value and/or to the other particular value.

Similarly, when values are expressed as approximations, by use of the antecedent "about," it will be understood that the particular value forms another aspect. It will be further understood that the endpoints of each of the ranges are significant both in relation to the other endpoint and independently of the other endpoint. Unless stated otherwise, the term "about" means within 5% (e.g., within 2% or 1%) of the particular value modified by the term "about."

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the endpoints of the range unless expressly stated otherwise. For example, a range of "between 5 and 10," "from 5 to 10," or "5-10" should generally be considered to include the endpoints 5 and 10. Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

As used herein, the term "composition" is intended to encompass a product comprising the specified ingredients in the specified amounts, as well as any product which results, directly or indirectly, from a combination of the specified ingredients in the specified amounts.

The polymeric or oligomeric compositions of the present invention may be a self-setting. The term "self-setting," as used herein, refers to the ability of the composition to create a crosslinked polymer network. In some aspects, a self-setting composition may be a liquid composition that may polymerize into a rigid polymer network. The crosslinking (setting) reactions are capable of proceeding at room and physiological temperature without modifications of the reagents or the addition of catalysts, etc. Thus, in some aspects, the crosslinked polymer network can form spontaneously, e.g., at room temperature or at body temperature, i.e., about 37° C. In some aspects, the crosslinked polymer network can form inside a subject, e.g., a human subject, after the polymeric or oligomeric composition of the invention is injected into the subject.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

It will be understood that when an element is referred to as being "connected" or "coupled" to another element, it can be directly connected or coupled to the other element, or intervening elements may be present. In contrast, when an element is referred to as being "directly connected" or "directly coupled" to another element, there are no intervening elements present. Other words used to describe the relationship between elements or layers should be interpreted in a like fashion (e.g., "between" versus "directly between," "adjacent" versus "directly adjacent," "on" versus "directly on"). As used herein, the term "and/or" includes any and all combinations of one or more of the associated listed items.

As used herein, the term or phrase "effective," "effective amount," or "conditions effective to" refers to such amount or condition that is capable of performing the function or property for which an effective amount or condition is expressed. As will be pointed out below, the exact amount or particular condition required will vary from one aspect to another, depending on recognized variables such as the materials employed and the processing conditions observed. Thus, it is not always possible to specify an exact "effective amount" or "condition effective to." However, it should be understood that an appropriate effective amount will be readily determined by one of ordinary skill in the art using only routine experimentation.

It will be understood that, although the terms "first," "second," etc., may be used herein to describe various elements, components, regions, layers and/or sections. These elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of example aspects.

As used herein, the term "substantially" means that the subsequently described event or circumstance completely occurs or that the subsequently described event or circumstance generally, typically, or approximately occurs.

Still further, the term "substantially" can in some aspects refer to at least about 80%, at least about 85%, at least about 90%, at least about 91%, at least about 92%, at least about 93%, at least about 94%, at least about 95%, at least about 96%, at least about 97%, at least about 98%, at least about 99%, or about 100% of the stated property, component, composition, or other condition for which substantially is used to characterize or otherwise quantify an amount.

In other aspects, as used herein, the term "substantially free" when used in the context of a composition or component of a composition that is substantially absent, is intended to refer to an amount that is then about 1% by weight, e.g., less than about 0.5% by weight, less than about 0.1% by weight, less than about 0.05% by weight, or less than about 0.01% by weight of the stated material, based on the total weight of the composition.

As used herein, the term "substantially" in, for example, the context "substantially identical" or "substantially similar" refers to a method or a system, or a component that is at least about 90%, at least about 91%, at least about 92%, at least about 93%, at least about 94%, at least about 95%, at least about 96%, at least about 97%, at least about 98%, at least about 99%, or about 100% by similar to the method, system, or the component it is compared to.

As used herein, the terms "substantially identical reference composition" or "substantially identical reference article" refer to a reference composition or article comprising substantially identical components in the absence of an inventive component. In another exemplary aspect, the term "substantially" in, for example, the context "substantially identical reference composition," refers to a reference composition comprising substantially identical components and wherein an inventive component is substituted with a common in the art component.

While aspects of the present invention can be described and claimed in a particular statutory class, such as the system statutory class, this is for convenience only and one of ordinary skill in the art will understand that each aspect of the present invention can be described and claimed in any statutory class. Unless otherwise expressly stated, it is in no way intended that any method or aspect set forth herein be construed as requiring that its steps be performed in a specific order.

Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The present invention may be understood more readily by reference to the following detailed description of various aspects of the invention and the examples included therein and to the Figures and their previous and following description.

The present invention may be understood more readily by reference to the following detailed description of various aspects of the invention and the examples included therein and to the Figures and their previous and following description.

Composition

The current disclosure relates to new bioadhesives with superior biocompatibility and strong wet tissue adhesion strength. Inspired by the strong adhesion of marine mussels to multiple heterogeneous surfaces underwater, mussel-inspired bioadhesives have been developed by incorporating, for example, L-DOPA (L-3,4-dihydroxyphenylalanine) or dopamine into polymers to achieve enhanced wet tissue adhesion and biocompatibility. Previously develops injectable citrate-based mussel-inspired bioadhesives (iCMBAs, or iCs) demonstrated strong tissue adhesion strengths in the range of 30-215 kPa (lap shear strength), 2.5-13.0 times stronger than that of the gold standard fibrin glue (~15 kPa). However, harsh oxidants, such as sodium periodate (PI), silver nitrite (SN), and iron (III) chloride ($FeCl_3$) used to crosslink these materials generated significant toxicity concerns. Additionally, constituted with hydrophilic PEG, crosslinked iCMBAs possess high swelling ratios (up to >1000 wt %).

In the present disclosure, a more hydrophobic iCMBA prepolymer (iC-EPE) was synthesized to provide compositions having lower swelling ratios, higher compatibility, and adhesion.

The present invention is directed to a composition comprising: a) polymer composition that is a polymerization product of one or more monomers of Formula (I), one or more monomers of Formula (II) and/or (II'), one or more monomers of Formula (III), and/or optionally one or more compounds of Formula (IV):

(I)

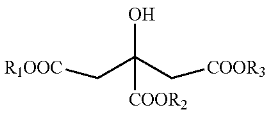

-continued (II)

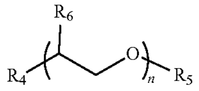

or (II')

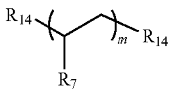

(III)

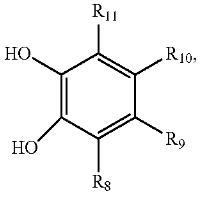

(IV)

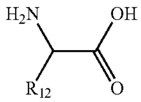

wherein $R_1$, $R_2$, and $R_3$ are, independently, selected from hydrogen, $C_1$-$C_{22}$ alkyl group; wherein each of $R_1$, $R_2$, and $R_3$, can be optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group, $C_2$-$C_{22}$ alkenyl group; $R_5$ is selected from hydrogen, amine, a hydroxyl group, alkoxyl group, or a $C_1$-$C_{22}$ alkyl group, $C_2$-$C_{22}$ alkenyl group; Re is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group, or a $C_2$-$C_{22}$ alkenyl group; wherein each of $R_4$, $R_5$, $R_6$, and $R_7$, can be optionally substituted with $C_1$-$C_{22}$ alkyl, $C_1$-$C_{22}$ alkoxy, $C_2$-$C_{22}$ alkenyl, $C_2$-$C_{22}$alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, $C_1$-$C_{22}$ alkyl group, amine, or a carboxylic acid, wherein each of $R_8$, $R_9$, $R_{10}$, and $R_{11}$, can be optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; n and m, are independently, integers from 1 to 2,000; $R_{12}$ is an amino acid side chain; $R_{14}$ is —OH or —$NH_2$; and wherein the formed polymer composition does not comprise metal cations; b) adding a first crosslinking initiator to the formed polymer composition; and c) crosslinking the formed polymer composition to form a composition comprising a crosslinked polymer composition forming a polymer network, wherein at least one crosslink in the crosslinked polymer comprises two catechol moieties directly and covalently coupled to each other; and wherein the composition is an adhesive composition.

In still further aspects, the disclosure is directed to a crosslinked composition comprising: a) a polymerization product of one or more monomers of Formula (I) and one or more units of a block copolymer comprising one or more monomers of Formula (II), and/or Formula (II'), one or more monomers of Formula (III), and/or optionally one or more compounds of Formula (IV):

(I)

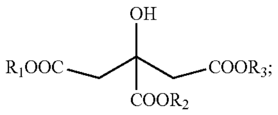

(II)

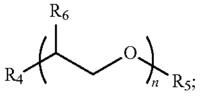

(II')

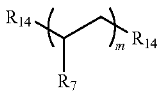

(III)

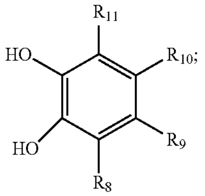

(IV)

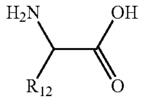

wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; $R_6$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m, are independently integers from 1 to 20; $R_{12}$ is an amino acid side chain; $R_{14}$ is —OH or —$NH_2$; and wherein the polymerization product does not comprise metal cations; and b) a first crosslinking initiator having a formula $A_{b'}O_{a''}$, wherein A is a monovalent, divalent, or trivalent metallic cation and wherein a' and b'' are dependent on the valency of A; wherein A is not a transition metal cation and wherein the first crosslinking initiator is configured to crosslink the reaction product to form the crosslinked composition; and wherein the crosslinked composition is a polymer network having at least one crosslink comprising two catechol moieties directly and covalently coupled to each other; wherein the crosslinked composition is a hydrogel or an organogel and is an adhesive composition.

It is understood that n and m can be an integer from 1 to 2,000, including exemplary values of 1 to 100, or 1-250, or 1-500, or 1-750, or 1-1,000, or 1-1,250, or 1-1,500, or 1-1,750.

In yet other aspects, n and m can be any integer between 1 and 20, including exemplary values of 2, 3, 4, 5, 6, 7, 8, 9, 10, 11, 12, 13, 14, 15, 16, 17, 18, and 19.

In still further aspects, the composition as disclosed herein comprises aspects wherein $R_1$, $R_2$, and $R_3$ are, independently, selected from hydrogen, —$CH_3$ group, or —$CH_2CH_3$ group; $R_4$ is selected from hydrogen, a hydroxyl group, —$NH_2$, —$OCH_3$, —$OCH_2CH_3$, —$CH_3$, —$CH_2CH_3$ group; a $C_3$ to $C_{22}$ alkyl or alkenyl group, —$CH_2CH_2OH$, or —$CH_2CH_2NH_2$; $R_5$ is selected from hydrogen, a hydroxyl group, —$NH_2$, —$OCH_3$, —$OCH_2CH_3$, —$CH_3$, or —$CH_2CH_3$ group, a $C_3$ to $C_{22}$ alkyl or alkenyl group, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$; $R_7$ is selected from hydrogen or —$CH_3$ group; $R_8$, $R_9$, $R_{10}$, and $R_{11}$ are, independently, selected from hydrogen, —$CH_2(CH_2)_xNH_2$, —$CH_2(CHR_{13})NH_2$, or —$CH_2(CH_2)_xCOOH$ groups; $R_{13}$ is —COOH or —$(CH_2)_yCOOH$ group; n and m are, independently, integers from 1 to 2,000; x is an integer from 0 to 20; and y is an integer from 1 to 20.

Yet in further aspects, the crosslinked composition disclosed herein comprises aspects wherein $R_1$, $R_2$, and $R_3$ are, independently selected from hydrogen, —$CH_3$ group, or —$CH_2CH_3$ group; $R_4$ is selected from hydrogen, a hydroxyl group, —$NH_2$, —$OCH_3$, —$OCH_2CH_3$, —$CH_3$, —$CH_2CH_3$ group; a $C_3$ to $C_{22}$ alkyl or alkenyl group, —$CH_2CH_2OH$, or —$CH_2CH_2NH_2$; $R_5$ is hydrogen, a hydroxyl group, —$NH_2$, —$CH_3$, or —$CH_2CH_3$ group, a $C_3$ to $C_{22}$ alkyl or alkenyl group, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$; $R_7$ is selected from hydrogen or —$CH_3$ group; $R_8$, $R_9$, $R_{10}$, and $R_{11}$ are, independently, selected from hydrogen, —$CH_2(CH_2)_xNH_2$, —$CH_2(CHR_{13})NH_2$, or —$CH_2(CH_2)_xCOOH$ groups; and wherein at least one of $R_8$, $R_9$, $R_{10}$, and $R_{11}$ is not hydrogen; $R_{13}$ is —COOH or —$(CH_2)_yCOOH$ group; n and m, are independently integers from 1 to 20; x is an integer from 0 to 20; and y is an integer from 1 to 20.

It is understood that in certain aspects, n and m can be any integers described above. Yet in other aspects, x can be any integer from 0 to 20, including exemplary values of 1, 2, 3, 4, 5, 6, 7, 8, 9, 10, 11, 12, 13, 14, 15, 16, 17, 18, and 19. While in other aspects, y can be any integer from 0 to 20, including exemplary values of 1, 2, 3, 4, 5, 6, 7, 8, 9, 10, 11, 12, 13, 14, 15, 16, 17, 18, and 19.

In still further aspects, the formula (I) can comprise an alkoxylated, alkenoxylated, or non-alkoxylated and non-alkenoxylated citric acid or ester/amide of citric acid.

In yet further aspects, the formula (II) can comprise polyethylene glycol, polypropylene glycol, or any combination thereof. In yet other aspects, a block polymer comprising polyethylene glycol, polypropylene glycol, and polyethylene glycol sequences can be formed. In yet further exemplary aspects, the formula (II) can comprise a poly (ethylene glycol) (PEG) or poly(propylene glycol) (PPG) having terminal hydroxyl or amine groups. In some aspects, for instance, a PEG or PPG has a weight average molecular weight between about 100 and about 5,000 or between about 200 and about 1,000, or between 200 and about 100,000 Da.

In some aspects, the block copolymer as disclosed herein can comprise repeating units of two or more monomers of Formula (II);

(II)

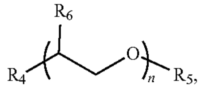

wherein $R_4$ is selected from hydrogen, a hydroxyl group, $—NH_2$, $—CH_2CH_2OH$, or $—CH_2CH_2NH_2$; $R_5$ is hydrogen, a hydroxyl group, $—NH_2$, $—CH_2CH_2OH$, or $—CH_2CH_2NH_2$; $R_6$ is selected from hydrogen, $—CH_3$ group, or $—CH_2CH_3$ group; $—CH_2CH_2OH$, or $—CH_2CH_2NH_2$.

For example, and without limitations, the block copolymer can have a formula (V) or formula (V'):

(V)

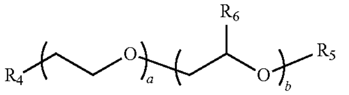

(V')

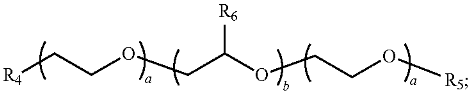

wherein a and b are independently chosen from n=1-20, and wherein $R_6$ is not hydrogen.

In still further aspects, the monomer of formula (II') can comprise any known in the art polyol. In certain aspects, the monomer of formula (II') can comprise a diol. While in other aspects, the monomer of formula (II') can also comprise a polyamine. In such exemplary aspects, the monomer of formula (II') can also comprise a diamine. Non-limiting examples of polyols/polyamines suitable for use in some aspects described herein include $C_2$-$C_{20}$, $C_2$-$C_{12}$, or $C_2$-$C_6$ aliphatic alkane diols/diamines, including α,ω-η-alkane diols/diamines, or α,ω-alkene diols/diamines. For instance, in some aspects, a polyol or polyamine can comprise 1,4-butanediol or 1,4 butane diamine, 1,6-hexanediol or 1,6-hexane diamine, 1,8-octanediol or, 8-octane diamine, 1,10-decanediol or 10-decane diamine, 1,12-dodecanediol or 1,12-dodecane diamine, 1,16-hexadecanediol or 1,16-hexadecane diamine, or 1,20-icosanediol or 1,20-icosane diamine. Branched aw-alkane diols/diamines or α,ω-alkene diols/diamines can also be used. Additionally, a polyol/polyamine can also be an aromatic diol/diamine.

Further, an amine, in some aspects, when present, can comprise one or more primary amines having two to ten carbon atoms. In other cases, an amine can comprise one or more secondary or tertiary amines having two to fifteen carbon atoms. An isocyanate, in some aspects, comprises a monoisocyanate. In other instances, an isocyanate comprises a diisocyanate, such as an alkane diisocyanate having four to twenty carbon atoms. An isocyanate described herein may also include a monocarboxylic acid moiety. Some additional examples of various isocyanates can be found in U.S. Patent Application Publication No. 2020/0140607 and International Patent Application Publication No. WO2018/227151, the contents of which are incorporated herein in its whole entirety.

In yet further aspects, the nucleophilic group of the one or more monomers of formula (III) is configured to react with at least one of $R_1COO—$, $R_2COO—$, or $R_3COO—$ of the one or more monomer of formula (I) to form a covalent bond. In still further aspects, the formula (III) can comprise any catechol-containing species. In certain aspects, the catechol-containing species can comprise at least one moiety that can form an ester or amide bond with another chemical species used to form a polymer in aspects where the monomers are reacted. For example, in some cases, a catechol-containing species comprises an alcohol moiety, an amine moiety, a carboxylic acid moiety, or a combination thereof. Further, in some instances, a catechol-containing species comprises a hydroxyl moiety that is not part of the catechol moiety. In some aspects, a catechol-containing species comprises dopamine. In other aspects, a catechol-containing species comprises L-3,4-dihydroxyphenylalanine (L-DOPA) or D-3,4-dihydroxyphenylalanine (D-DOPA). In still other aspects, a catechol-containing species comprises gallic acid or caffeic acid.

In some cases, a catechol-containing species comprises 3,4-dihydroxyhydrocinnamic acid. Additionally, a catechol-containing species can also comprise a naturally-occurring species or a derivative thereof, such as tannic acid or tannin. Moreover, in some aspects, a catechol-containing species is coupled to the backbone of the polymer through an amide bond. In other aspects, a catechol-containing species is coupled to the backbone of a polymer formed by the monomers through an ester bond. Some additional examples can be found in U.S. Patent Application Publication No. 2020/0140607, and International Patent Application Publication No. WO2018/227151, the contents of which are incorporated herein in its whole entirety.

In still further aspects, the formula (III) can comprise dopamine, L-DOPA, D-DOPA, and 3,4-dihydroxyhydrocinnamic acid. In still further aspects, the monomer of Formula (III) comprises dopamine of L-DOPA. In some aspects, the composition comprises one or more monomers selected from maleic acid, maleic anhydride, and fumaric acid.

In certain exemplary and unlimiting aspects, the polymerization product can comprise:

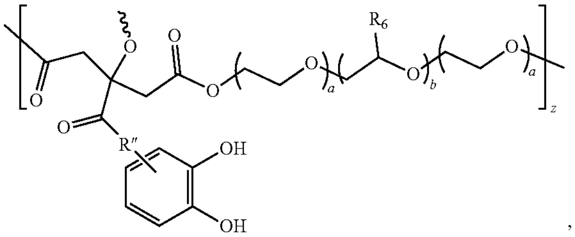

, wherein R" is —N(H)$R_{15}$, or —O(CO)($R_{15}$), or —O($R_{15}$); wherein $R_{15}$ is independently selected from $C_1$-$C_{22}$ alkyl group, optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl groups; wherein $R_6$ is not hydrogen; wherein ∿∿∿ defines a bond to hydrogen, or optionally to a predetermined polymer chain if present; wherein a and b are independently chosen from n=1-20, and wherein z=1-100.

In still further aspects, the polymer composition can comprise the one or more monomers of Formula (II) and (II').

In still further aspect, where the compound of Formula (IV) is present, the compound can comprise an alpha-amino acid. In still further aspects, the alpha-amino acid can comprise an L-amino acid, a D-amino acid, or a D, L-amino acid. In some cases, an alpha-amino acid can comprise alanine, arginine, asparagine, aspartic acid, cysteine, glycine, glutamine, glutamic acid, histidine, isoleucine, leucine, lysine, methionine, praline, phenylalanine, serine, threonine, tyrosine, tryptophan, valine, or a combination thereof. Further, in some instances, an alpha-amino acid comprises an alkyl-substituted alpha-amino acid, such as a methyl-substituted amino acid derived from any of the 22 "standard" or proteinogenic amino acids, such as methyl serine. It is understood that in some aspects, the polymerization product as described herein can be a polymerization product of one or more monomers of Formula (I) and compounds of formula (IV) with or without one or more monomer so Formula (II) and/o (II') or Formula (III). In yet further aspects where the compound of formula (IV) are present in the polymerization product, the composition can exhibit fluorescent, or phosphorescent, or luminescent properties.

Additional examples for monomers to be used to form the polymer composition and their ratios can be found in U.S. Patent Application Publication No. 2020/0140607, and International Patent Application Publication No. WO2018/227151, the contents of which are incorporated herein in its whole entirety.

In still further aspects, the polymerization product as recited herein can also be formed from the cited herein monomers of Formula (I), (II) and/or (II'), (III), and a polycarboxylic acid such as a dicarboxylic acid or a functional equivalent of a polycarboxylic acid, such as a cyclic anhydride or an acid chloride of a polycarboxylic acid. In such cases, the polyol/polyamine can comprise any polyol/polyamine described above, and the ester of citric acid can comprise any ester/amide of citric acid described above. Moreover, the polycarboxylic acid or functional equivalent thereof can be saturated or unsaturated. For example, in some instances, the polycarboxylic acid or functional equivalent thereof comprises maleic acid, maleic anhydride, fumaric acid, or fumaryl chloride. A vinyl-containing polycarboxylic acid or a functional equivalent thereof may also be used, such as allylmalonic acid, allylmalonic chloride, itaconic acid, or itaconic chloride.

Further, in some cases, the polycarboxylic acid or functional equivalent thereof can be at least partially replaced with an olefin-containing monomer that may or may not be a polycarboxylic acid. In such aspects, for instance, an olefin-containing monomer comprises an unsaturated polyol, such as a vinyl-containing diol. Additional examples can be found in U.S. Patent Application Publication No. 2020/0140607, and International Patent Application Publication No. WO2018/227151, the contents of which are incorporated herein in its whole entirety.

In still further aspects, the polymer composition is the polymerization product, which is a product of a condensation polymerization reaction of any of the disclosed herein monomers and their combinations. In some aspects, at least two of the identified species or monomers polymerize to form a copolymer. In still further aspects, and as disclosed herein, at least two of the identified species or monomer form a block copolymer. In yet further aspects, the block copolymers described herein can be formed prior to forming the disclosed herein polymerization product. For example, and without limitations, the block copolymer can be first formed from two or more monomers of formula (II) and then reacted with the monomer of formula (I) and/or (III). In some such aspects, the monomers react to form an alternating copolymer or a statistical copolymer of the reacted monomers. Additionally, species or monomers described hereinabove may also react to form pendant groups or side chains of a copolymer or can form cyclic structures that may form part of the backbone of a polymer or oligomer.

In yet further aspects, the polymerization product as recited herein can also be formed from the cited herein monomers of Formula (I), (II) and/or (II'), (III), and/or optionally compound of Formula (IV) and one or more monomers comprising one or more alkyne moieties or one or more azide moieties. While in other aspects, diols described herein can comprise diazido-diols or alkyne diols. Additional examples for alkyne moieties or azide moieties can be found in U.S. Patent Application Publication No. 2020/0140607, and International Patent Application Publication No. WO2018/227151, the contents of which are incorporated herein in its whole entirety.

Additionally, in some aspects, a monomer used herein to form the polymer compositions can be functionalized with a bioactive species. Moreover, an additional monomer can comprise one or more alkyne and/or azide moieties. For example, in some instances, a polymer composition described herein is formed from one or more monomers comprising a peptide, polypeptide, nucleic acid, or polysaccharide, wherein the peptide, polypeptide, nucleic acid, or polysaccharide is functionalized with one or more alkyne and/or azide moieties. In some cases, the bioactive species of a polymer composition described herein is a growth factor or signaling molecule. Further, a peptide can comprise a dipeptide, tripeptide, tetrapeptide, or a longer peptide. As described further hereinbelow, forming a polymer composition from such a monomer, in some aspects, can provide additional biological functionality to a composition described herein.

In still other aspects, the composition comprises a compound having a formula $A_bB_a$, wherein A is a metal a monovalent, divalent, or trivalent cation and B is an anion, and wherein a and b are defined by the valency of A and B. It is understood that the compound $A_bB_a$ can comprise any salt or oxide known in the art. For example, in some cases, A is a monovalent, divalent, or trivalent metal cation, and B is a simple anion or a complex anion. The monovalent, divalent, or trivalent cation described herein is not limited and can include, for example, at least one of $Mg^{2+}$, $Ca^{2+}$, $Zn^{2+}$, $Cu^{2+}$, $Co^{2+}$, $Fe^{2+}$, $Fe^{3+}$, $Cr^{2+}$, $Mn^{2+}$, $Co^{3+}$, $Sr^{2+}$, $V^{2+}$, $V^{3+}$, $Ti^{2+}$, $Ti^{3+}$, $Sr^{2+}$, $Ni^{2+}$, $Al^{3+}$, $Al^{2+}$, $Cr^{3+}$, $Ba^{2+}$, $Na^{+}$, $K^{+}$, and $Li^{+}$. The anion B is not limited and can be any anion that forms a neutral salt or an oxide with the monovalent, divalent, or trivalent metal cation. For example, and without limitations, B can be $O^{2-}$, $Cl^{-}$, citrate, $Br^{-}$, $C_3^{2-}$, $PO_4^{3-}$, or $NO_3^{-}$. Other anions can also be used.

Yet, in other aspects, the composition as disclosed herein comprises a first crosslinking initiator having a formula $A_{b'}O_{a''}$, wherein A is a monovalent, divalent, or trivalent metallic cation and wherein a' and b" are dependent on the valency of A; wherein A is not a transition metal cation. For example, in some cases, A is a monovalent, divalent, or trivalent metal cation. The monovalent, divalent, or trivalent cation described herein is not limited and can include, for example, at least one of $Mg^{2+}$, $Ca^{2+}$, $Zn^{2+}$, $Cu^{2+}$, $Co^{2+}$, $Fe^{2+}$, $Fe^{3+}$, $Cr^{2+}$, $Mn^{2+}$, $Co^{3+}$, $Sr^{2+}$, $V^{2+}$, $V^{3+}$, $Ti^{2+}$, $Ti^{3+}$, $Sr^{2+}$, $Ni^{2+}$, $A^{3+}$, $Al^{2+}$, $Cr^{3+}$, $Ba^{2+}$, $Na^{+}$, $K^{+}$, and $Li^{+}$. In yet other aspects, the first crosslinking initiator having formula $A_{b'}O_{a'}$ can comprise magnesium oxide, calcium oxide, zinc oxide, barium oxide, cesium oxide, or any combination thereof.

In still further aspects, the compound having a formula $A_bB_a$ behaves as a first crosslinking initiator. It is understood that when the product of polymerization, as described herein, is mixed with the first crosslinking initiator, a crosslinked polymer composition, as claimed, is formed. It is further understood that such a composition still comprises an amount of the compound having a formula $A_bB_a$. In still further aspects, the compound of a formula $A_bB_a$ comprises a metal oxide. In such exemplary aspects, the metal oxide is a metal oxide of Zn, Mg, Cu, Fe, $B_a$, Ca, or a combination thereof In yet other aspects, the compositions disclosed herein comprise the first crosslinking initiator having formula $A_{b'}O_{a''}$. In such aspects, similarly to any aspects disclosed above, when the product of polymerization, as described herein, is mixed with the first crosslinking initiator having formula $A_{b'}O_{a''}$, a crosslinked polymer composition, as claimed, is formed. It is further understood that such a composition still comprises an amount of the compound having a formula $A_{b'}O_{a''}$. Again, it is understood that any of the disclosed metal oxides can be used.

In yet further aspects, this first crosslinking initiator can also behave as a filler. In such aspects, the first crosslinking initiator can behave as both a crosslinking initiator and filler simultaneously. In such exemplary aspects, substantially no other fillers need to be added. However, in still further aspects, for example, in the aspects where the composition is self-setting, additional fillers such as hydroxyapatite, B-tricalcium phosphate, pearl powder, and octacalcium phosphate, or any combination thereof, can be added.

As shown herein, the metal oxides can act as both crosslinking initiators (biocompatible oxidant) and composite fillers in the first instance, to simultaneously enhance the cohesion and adhesion strengths of these bioadhesives, and as a bioactive component promoting antibacterial and regulating cellular activities over the lifetime of the composite.

In still further aspects, the compound of a formula $A_bB_a$ or $A_{b'}O_{a'}$ can be present in an amount from greater than 0 wt % to less than 100 wt % based on a weight percent of a dry polymer or a dry polymerization product. In some exemplary aspects, the first crosslinking initiator, or the compound of a formula $A_bB_a$, or, more specifically, for example, and without limitation, $A_{b'}O_{a'}$ can be present in an amount of about 0.1 wt %, about 0.5 wt %, about 1 wt %, about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, and about 95 wt %. In yet further aspects, the compound of a formula $A_bB_a$ or $A_{b'}O_{a'}$ can be present in an amount from greater than 0 wt % to about 40 wt % based on a weight percent to dry polymer (or a dry polymerization product), including exemplary values of about 1 wt %, about 5 wt %, about 10 wt %, about 15 wt %, about 20 wt %, about 25 wt %, about 30 wt %, and about 35 wt %.

In still further aspects, the polymer composition or the crosslinked polymer composition, as described herein, represents a majority of the composition. In still further aspects, the polymer compositions as described herein is present in an amount of more than 60%, more than 70%, more than 80%, more than 90%, more than 95%, more than 99%, or more than about 99% of the total weight of the composition. Yet, in other aspects, the polymer composition, as described herein, can be in any amount from greater than 0 wt % to less than 100 wt %. For example, the polymer compositions as described herein can be present in an amount of about 10%, about 20%, about 30%, about 40%, about 50%, about 60%, about 70%, about 80%, about 90%, or about 95%, the total weight of the composition.

In still further aspects, the polymer composition and the compound of a formula $A_bB_a$ or $A_{b'}O_{a'}$ can be present in any ratio between 1:10 and 10:1. For example, they can be present in a ratio of 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1.

In yet further aspects, the first crosslinking initiator, or the compound of a formula $A_bB_a$ or $A_{b'}O_{a'}$ can be added to form the current composition as a solid or as a dispersion. In certain aspects, the first crosslinking initiator, or the compound of a formula $A_bB_a$ or $A_{b'}O_{a'}$ can be present at a concentration of about 0.001 M or higher, e.g., about 0.005 M or higher, about 0.01 M or higher, about 0.05 M or higher, about 0.1 M or higher, about 0.5 M or higher, or about 1 M or higher. In still further aspects, the first crosslinking initiator, or the compound of a formula $A_bB_a$ can be present at a concentration of about 0.001 M or higher, e.g., about 0.005 M or higher, about 0.01 M or higher, about 0.05 M or higher, about 0.1 M or higher, about 0.5 M or higher, or about 1 M or higher.

In some aspects, the polymeric or oligomeric compositions of the invention may comprise salt, e.g., associated or dissociated salt comprising a monovalent, divalent, or trivalent metal cation, or metal oxide at a concentration of about 0.001 M to about 2 M, about 0.001 M to about 0.01 M, about 0.005 M to about 0.01 M, about 0.005 M to about 0.05M, about 0.01 M to about 0.1 M, about 0.05 M to about 0.1 M, about 0.1 M to about 1 M, or about 0.5 M to about 2M.

In yet further aspects, the composition is a hydrogel or an organogel. In still further aspects, the composition can comprise an amount of a solvent. In certain aspects, the solvent can comprise water or a mixture of water and an organic solvent. In further aspects, the mixture is formed primarily from water, e.g., the solvent comprises at least 95% by volume water. An aqueous solvent comprises a majority (greater than 50%) water and may comprise more than 60%, more than 70%, more than 80%, more than 90%, more than 95%, more than 99%, but not 100% water. In some aspects, the aqueous solvent also comprises an organic co-solvent, including a polar or non-polar organic solvent (such as acetone or ethanol) in an amount greater than 0% but not greater than 50%. In yet further aspects, the organic solvent can be any biocompatible solvent. In still further aspects, the organic solvent comprises ethanol. In such exemplary aspects, the solvent can be water, ethanol, or a combination thereof.

In some aspects, the first crosslinking initiator, or the compound of a formula $A_bB_a$ or $A_{b'}O_{a'}$ can have a solubility of at least 50 g/100 mL in water at 25° C. In some aspects, the first crosslinking initiator, or the compound of a formula $A_bB_a$ or $A_{b'}O_{a'}$ can have a solubility of 5.0 g/L or less in water at 25° C. In some aspects, the first crosslinking initiator, or the compound of a formula $A_bB_a$ or $A_{b'}O_{a'}$ has a solubility of 1.0 g/L or less in water at 25° C. In some aspects, the first crosslinking initiator, or the compound of a formula $A_bB_a$ or $A_{b'}O_{a'}$ can have described herein, may be soluble, partially soluble, or insoluble in water or an aqueous or water-based solvent described herein. In still further aspects, the first crosslinking initiator, or the compound of a formula $A_bB_a$ or $A_{b'}O_{a'}$ can be added as a dispersion. In some cases, the solubility of the first crosslinking initiator, or the compound of a formula $A_bB_a$ or $A_{b'}O_{a'}$ in water can be at least 30 g/100 mL, at least 50 g/100 mL, or at least 75 g/100 mL at 25° C. Alternatively, in other aspects, the solubility of the compound of a formula $A_bB_a$ or $A_{b'}O_{a'}$ in water may be less than 30 g/L, less than 20 g/L, less than 10 g/L, less than 5 g/L, or less than 1 g/L at 25° C.

In still further aspects, described herein are the compositions where a combination of the compound of a formula $A_{b'}O_{a'}$ and $A_bB_a$, where B is not oxygen, can also be present. The ration of these two compounds $A_{b'}O_{a'}$:$A_bB_a$ can be anywhere between 10:1 to 1:10, including exemplary values of about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, and about 1:9. It is understood that any ratios in between any two foregoing values can also be used.

In still further aspects, the composition can further comprise a second crosslinking initiator. In such aspects, the second crosslinking initiator can be different from the first crosslinking initiator. It is understood that any known in the art additional crosslinking initiator can be added. In certain aspects, the crosslinking initiator can comprise sodium periodate, silver nitrate, or ferric chloride, or any combination thereof. In still further aspects, the second crosslinking initiator can be present in any amount from greater than 0 wt % to about 40 wt % based on a weight percent to a dry polymer or a polymerization product, including exemplary values of about 1 wt %, about 5 wt %, about 10 wt %, about 15 wt %, about 20 wt %, about 25 wt %, about 30 wt %, and about 35 wt %. In yet still further aspects, the second crosslinking initiator is present in an amount from greater than 0 wt % to about 8 wt %, including exemplary values of about 0.01 wt %, about 0.05 wt %, about 0.1 wt %, about 0.5 wt %, about 1 wt %, about 1.5 wt %, about 2 wt %, about 2.5 wt %, about 3 wt %, about 3.5 wt %, about 4 wt %, about 4.5 wt %, about 5 wt %, about 5.5 wt %, about 6 wt %, about 6.5 wt %, about 7 wt %, and about 7.5 wt %, based on a weight percent of a dry polymerization product.

In such aspects, the second crosslinking initiator can be added to the composition in any form similar to the first crosslinking initiator. In yet further aspects, the second and the first crosslinking initiator have a synergistic effect on the composition.

In still further aspects, the composition can comprise a sol content less than about 25%, less than about 20%, less than about 15%, less than about 10%, or less than about 5%.

In yet further aspects, the composition exhibits a swelling ratio of less than about 200%, less than about 190%, less than about 180%, less than about 170%, less than about 160%, less than about 150%, less than about 140%, less than about 130%, less than about 120%, less than about 110%, less than about 100%, less than about 90%, less than about 80%, less than about 70%, less than about 60%, or less than about 50%.

In still further aspects, the composition, as described herein, can also be a self-setting composition. Self-setting formulations described herein, in some aspects, are capable of acting as void fillers with significant mechanical strength, elasticity, and self-healing potential. Self-setting formulations described herein can also be altered with the addition of ceramics or other additives. Metal oxide derived crosslinks described herein are capable of incorporating ions including calcium, magnesium, and zinc, which possess osteogenic differentiation potential, as well as ions including copper and zinc with antibacterial capability. Self-setting citrate-based materials described herein, therefore, have potential in the orthopedic field as void fillers and anchoring for surgical implants and scaffolds, as well as, when combined with porogens and other additives, anatomically correct scaffolds based on patient specific anatomy. In some aspects, the self-setting composition of the invention has a setting time of less than 120 minutes at room temperature (25° C.), e.g., less than 80 minutes at room temperature (25° C.) or less than 60 minutes at room temperature (25° C.). In some aspects, the self-setting composition of the invention has a setting time of less than 40 minutes at a physiological temperature of 37° C., e.g., less than 20 minutes at a physiological temperature of 37° C. In some aspects, the composition does not comprise a catalyst that affects setting time.

In yet other aspects, the compositions disclosed herein are not self-setting.

In still further aspects, the compositions can exhibit a tensile strength of about 1 to about 10 MPa in a dry state as measured according to ASTM D412A, including exemplary values of about 2 MPa, about 3 MPa, about 4 MPa, about 5 MPa, about 6 MPa, about 7 MPa, about 8 MPa, and about 9 MPa.

In yet further aspects, the composition can exhibit an elongation at break from about 15% to about 150% a dry state as measured according to ASTM D412A, including exemplary values of about 18%, about 20%, about 22%, about 25%, about 27%, about 30%, about 32%, about 35%, about 37%, about 40%, about 42%, about 45%, about 47%, about 50%, about 52%, about 55%, about 57%, about 60%, about 62%, about 65%, about 67%, about 70%, about 72%, about 75%, about 77%, about 80%, about 82%, about 85%, about 87%, about 90%, about 92%, about 95%, about 97%, about 100%, about 102%, about 105%, about 107%, about 110%, about 112%, about 115%, about 117%, about 120%, about 122%, about 125%, about 127%, about 130%, about 132%, about 135%, about 137%, about 140%, about 142%, about 145%, and about 147%.

In still further aspects, the compositions can exhibit a modulus of about 1 to about 10 MPa in a dry state as measured according to ASTM D412A, including exemplary values of about 2 MPa, about 3 MPa, about 4 MPa, about 5 MPa, about 6 MPa, about 7 MPa, about 8 MPa, and about 9 MPa.

In still further aspects, the composition can exhibit a lap shear strength of greater than about 30 kPa, greater than about 35 kPa, greater than about 40 kPa, greater than about 45 kPa, greater than about 50 kPa, greater than about 55 kPa, or greater than about 60 kPa, as measured according to a modified ASTM D1002-05 method.

In still further aspects, the composition can exhibit a higher cytocompatibility as measured against human mesenchymal stem cells when compared to a substantially identical reference composition with an absence of the metal oxide. In still further aspects, the composition exhibits an increased inhibition against *S. aureus* and *E. coli* when compared to a substantially identical reference composition in the absence of the metal oxide.

In still further aspects, the composition can comprise at least one pharmaceutically active component. In such aspects, the pharmaceutically active components can comprise, for example, and without limitation, any drugs that can assist in a specified treatment, such as antibiotics, inflammatory compounds, steroids, etc.

In still further aspects, the composition is injectable. In yet other aspects, the composition is configured to fill a void, wherein the void can be physiological. In yet further aspects, the composition is a wound closing composition.

In still further aspects, the compositions of the present invention can have multiple potential uses in tissue engineering, including in situ setting, formation of anatomically correct scaffolds when combined with molding, and 3D printing of scaffolds utilizing the rapid setting potential of the system. Additionally, the compositions of the present invention have potential uses in the orthopedic field as void fillers and as anchoring for surgical implants and scaffolds, as well as, when combined with porogens and other additives, as anatomically correct scaffolds based on patient specific anatomy.

In still further aspects, the use of the disclosed herein compositions include but is not limited to the following: orthopedic tissue engineering materials including composites and porous scaffolds for critical size segmental defect repair and fixation and spinal fusion and films for periosteum repair and barrier functionality; antibacterial capable materials for preventing and controlling infection; hemostat capable materials for controlling bleeding in wounds and surgical implantation procedures; self-setting materials for void filling and fracture fixation; and self-setting materials for the generation of molded or 3D printed scaffolds.

Any of the disclosed herein compositions can also be formed by a) forming a polymerization product by reacting a polycarboxylic acid of one or more monomers of Formula (I) with a block copolymer comprising one or more monomers of Formula (II), and/or Formula (II'), one or more monomers of Formula (III), and/or optionally one or more compounds of Formula (IV):

(I)

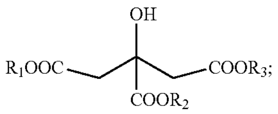

(II)

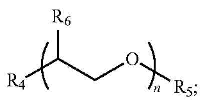

(II')

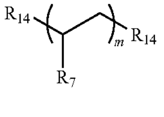

(III)

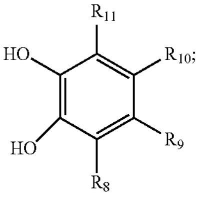

-continued (IV)

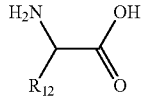

Wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; $R_6$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m, are independently integers from 1 to 20; $R_{12}$ is an amino acid side chain; $R_{14}$ is —OH or —$NH_2$; and wherein the polymerization product does not comprise metal cations; b) crosslinking the polymerization product with a first crosslinking initiator having a formula $A_{b'}O_{a'}$, wherein A is a monovalent, divalent, or trivalent metallic cation and wherein a' and b" are defined by the valency of A; wherein A is not a transition metal cation; wherein the crosslinked composition is a polymer network having at least one crosslink comprising two catechol moieties directly and covalently coupled to each other; wherein the crosslinked composition is a hydrogel or organogel and is an adhesive composition.

It is understood that any of the disclosed above compounds, monomer, solvents, reactants can be utilized to form the disclosed herein composition.

Methods

Also disclosed herein are the methods of making the described above compositions. In such aspects, disclosed is a method of making a composition, comprising: a) mixing a polycarboxylic acid of one or more monomers of Formula (I)

(I)

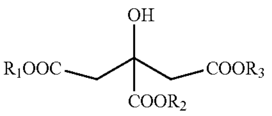

with a compound comprising one or more monomers of Formula (II) and/or (II')

(II)

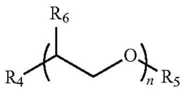

or (II')

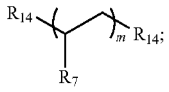

and/or with a compound of one or more monomers of Formula (III)

(III)

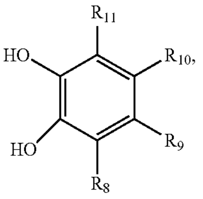

and/or optionally with one or more compounds of Formula (IV)

(IV)

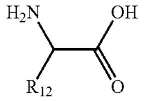

at conditions effective to form a polymer composition configured to be crosslinked; wherein $R_1$, $R_2$, and $R_3$ are, independently, selected from hydrogen, $C_1$-$C_{22}$ alkyl group; wherein each of $R_1$, $R_2$, and $R_3$, can be optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group, $C_2$-$C_{22}$ alkenyl group; $R_5$ is selected from hydrogen, amine, a hydroxyl group, alkoxyl group, or a $C_1$-$C_{22}$ alkyl group, $C_2$-$C_{22}$ alkenyl group; Re is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group, or a $C_2$-$C_{22}$ alkenyl group; wherein each of $R_4$, $R_5$, $R_6$, and $R_7$, can be optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, $C_1$-$C_{22}$ alkyl group, amine, or a carboxylic acid, wherein each of $R_8$, $R_9$, $R_{10}$, and $R_{11}$, can be optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; n and m are, independently, integers from 1 to 2000; $R_{12}$ is amino acid side chain; $R_{14}$ is —OH or —$NH_2$; and wherein the formed polymer composition does not comprise metal cations; b) adding a first crosslinking initiator to the formed polymer composition; and c) crosslinking the formed polymer composition to form a composition comprising a crosslinked polymer composition forming a polymer network, wherein at least one crosslink in the crosslinked polymer comprises two catechol moieties directly and covalently coupled to each other; and wherein the composition is an adhesive composition.

In yet other aspects, disclosed are methods of making a composition, comprising: a) reacting a polycarboxylic acid of one or more monomers of Formula (I)

(I)

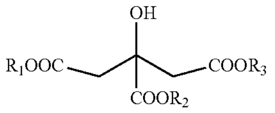

with one or more units of a block copolymer comprising one or more monomers of Formula (II) and (II'), (II)

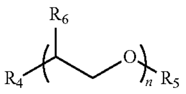

or (II')

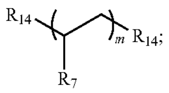

and with a compound of one or more monomers of Formula (III)

(III)

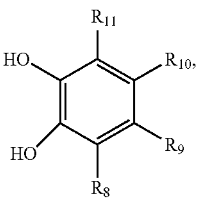

and optionally with one or more compounds of Formula (IV)

(IV)

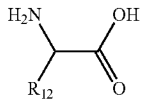

at conditions effective to form a prepolymer composition configured to be crosslinked; wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; $R_5$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m, are independently integers from 1 to 20; $R_{12}$ is an amino acid side chain; $R_{14}$ is —OH or —$NH_2$; and wherein the polymerization product does not comprise metal cations; b) adding a first crosslinking initiator to the prepolymer composition; wherein the first crosslinking initiator has a formula $A_bB_a$, wherein A is a monovalent, divalent, or trivalent metallic cation and B is an anion, and wherein a and b are defined by the valency of A and B; wherein A is not a transition metal cation and c) crosslinking the prepolymer composition to form a crosslinked composition comprising a polymer network, wherein at least one crosslink in the crosslinked polymer comprises two catechol moieties directly and covalently coupled to each other; and wherein the crosslinked composition is a hydrogel or organogel and is adhesive In still further aspects, $R_1$, $R_2$, and $R_3$ are, independently, selected from hydrogen, —$CH_3$ group, or —$CH_2CH_3$ group; $R_4$ is selected from hydrogen, a hydroxyl group, —$NH_2$, —$OCH_3$, —$OCH_2CH_3$, —$CH_3$, —$CH_2CH_3$ group; a $C_3$ to $C_{22}$ alkyl or alkenyl group, —$CH_2CH_2OH$, or —$CH_2CH_2NH_2$; $R_5$ hydrogen, a hydroxyl group, —$NH_2$, —$OCH_3$, —$OCH_2CH_3$, —$CH_3$, or —$CH_2CH_3$ group, a $C_3$ to $C_{22}$ alkyl or alkenyl group, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$; $R_7$ is selected from hydrogen or —$CH_3$ group; $R_8$, $R_9$, $R_{10}$, and $R_{11}$ are, independently, selected from hydrogen, —$CH_2(CH_2)_xNH_2$, —$CH_2(CHR_{13})NH_2$, or —$CH_2(CH_2)_xCOOH$ groups; $R_{13}$ is —COOH or —$(CH_2)_y$COOH group; n and m, are independently, integers from 1 to 2,000; x is an integer from 0 to 20; and y is an integer from 1 to 20.

While in still further aspects, $R_1$, $R_2$, and $R_3$ are, independently, selected from hydrogen, —$CH_3$ group, or —$CH_2CH_3$ group; $R_4$ is selected from hydrogen, a hydroxyl group, —$NH_2$, —$OCH_3$, —$OCH_2CH_3$, —$CH_3$, —$CH_2CH_3$ group; a $C_3$ to $C_{22}$ alkyl or alkenyl group, —$CH_2CH_2OH$, or —$CH_2CH_2NH_2$; $R_5$ is hydrogen, a hydroxyl group, —$NH_2$, —$CH_3$, or —$CH_2CH_3$ group, a $C_3$ to $C_{22}$ alkyl or alkenyl group, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$; $R_7$ is selected from hydrogen or —$CH_3$ group; $R_8$, $R_9$, $R_{10}$, and $R_{11}$ are, independently, selected from hydrogen, —$CH_2(CH_2)_xNH_2$, —$CH_2(CHR_{13})NH_2$, or —$CH_2(CH_2)_xCOOH$ groups; and wherein at least one of $R_8$, $R_9$, $R_{10}$, and $R_{11}$ is not hydrogen; $R_{13}$ is —COOH or —$(CH_2)_y$COOH group; n and m, are independently integers from 1 to 20; x is an integer from 0 to 20; and y is an integer from 1 to 20.

In yet further aspects, the nucleophilic group of the one or more monomers of formula (III) reacts with at least one of $R_1COO$—, $R_2COO$—, or $R_3COO$— of the one or more monomer of formula (I) to form a covalent bond In still further aspects, any of the disclosed monomers of the formula (I), (II), (II'), or (III) can be used in the disclosed methods.

In still further aspects, the block copolymer can be formed prior to reacting in step a) disclosed above.

Also disclosed herein are methods where the block copolymer is formed prior to reacting in step a) and comprises repeating units of two or more monomers of Formula (II);

(II)

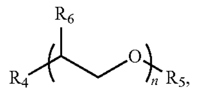

wherein $R_4$ is selected from hydrogen, a hydroxyl group, —$NH_2$, —$CH_2CH_2OH$, or —$CH_2CH_2NH_2$; $R_5$ is hydrogen, a hydroxyl group, —$NH_2$, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$.

In some exemplary and unlimiting aspects, the block copolymer can have a formula (V) or formula (V'):

(V)

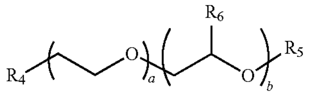

(V')

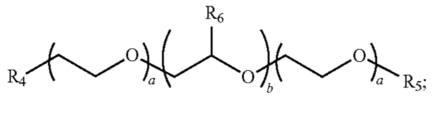

wherein a and b are independently chosen from n=1-20, and wherein $R_6$ is not hydrogen.

Any of the disclosed above monomers of formula (III) can be reacted with the disclosed herein block polymers and monomers of formula (I).

In some exemplary and unlimiting aspects, the polymerization product formed by the disclosed herein methods can comprise:

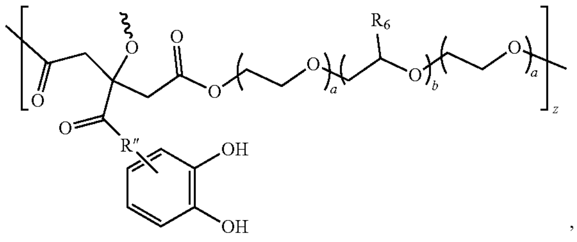
, wherein R" is —N(H)$R_{15}$, or —O(CO)($R_{15}$), or —O($R_{15}$); wherein $R_{15}$ is independently selected from $C_1$-$C_{22}$ alkyl group, optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl groups; wherein $R_6$ is not hydrogen; wherein ∿∿∿ defines a bond to hydrogen, or optionally to a predetermined polymer chain if present; wherein a and b are independently chosen from n=1-20, and wherein z=1-100.

In still further aspects, the first crosslinking initiator can be any compounds in any amounts, as disclosed above. It is understood that these compounds can be added as solids or as a solution, and the compositions disclosed herein can be formed by simple mixing. In still further aspects, where the first crosslinking initiator is provided as a solution, it can be a dispersion of the first crosslinking initiator in a solvent. Any of the disclosed above solvents can be utilized.

In such aspects, the first crosslinking initiator simultaneously can also behave as a first filler. In certain exemplary and unlimiting aspects, no other fillers are added to the composition. Yet, in some additional aspects, an additional filler that is different from the first crosslinking initiator can also be added.

In still further aspects, the methods disclosed herein comprise addition of a second crosslinking initiator. Any known crosslinking initiators can be utilized. In certain aspects, the second crosslinking initiator comprises sodium periodate, silver nitrate, or ferric chloride, or any combination thereof. In still further aspects, the second crosslinking is added in the solvent dispersion of the first crosslinking initiator. While in other aspects, the second crosslinking initiator can be added as a separate solvent dispersion of the second crosslinking initiator. Any amounts of the first and/or second crosslinking initiators disclosed herein can be used in the described methods.

In still further aspects, the formed compositions disclosed herein are hydrogels or organogels. In such aspects, a gel time needed to form the hydrogel or organogel is from about 500 s to less than about 10 s, including exemplary values of about 450 s, about 400 s, about 350 s, about 300 s, about 250 s, about 200 s, about 150 s, about 100 s, about 50 s, about 40 s, about 30 s, about 20 s, about 10 s, about s, or even about 1 s.

In still further aspects, the first and the second crosslinking initiators have a synergistic effect on the steps of forming the desired composition.

In certain aspects, the methods described herein comprise a crosslinking rate that is substantially higher when compared to a substantially identical reference method in the absence of the metal oxide.

Also disclosed are methods where the compound of Formula (IV) is also present.

In still further aspects, the step of crosslinking comprises: metal oxide initiated crosslinking via coupling of catechol groups of the polymer composition, formation of a metal complex with the catechol groups of the polymer composition, bonding metal oxide via hydrogen bonds or surface bonds with carboxyl groups or catechol groups of the polymer composition; or any combination thereof.

In yet further aspects, the formed compositions exhibit a sol content and swelling ratio, as described above. For example, in some aspects, the formed compositions can comprise a sol content less than about 25%, less than about 20%, less than about 15%, less than about 10%, or less than about 5%. While in other aspects, the formed composition can exhibit a swelling ratio of less than about 200%, less than about 190%, less than about 180%, less than about 170%, less than about 160%, less than about 150%, less than about 140%, less than about 130%, less than about 120%, less than about 110%, less than about 100%, less than about 90%, less than about 80%, less than about 70%, less than about 60%, or less than about 50%.

In yet further aspects, the formed by the methods disclosed herein compositions can exhibit a tensile strength of about 1 to about 10 MPa in a dry state as measured according to ASTM D412A, including exemplary values of about 2 MPa, about 3 MPa, about 4 MPa, about 5 MPa, about 6 MPa, about 7 MPa, about 8 MPa, and about 9 MPa.

In yet further aspects, the formed by the methods disclosed herein composition can exhibit an elongation at break from about 15% to about 150% a dry state as measured according to ASTM D412A, including exemplary values of about 18%, about 20%, about 22%, about 25%, about 27%, about 30%, about 32%, about 35%, about 37%, about 40%, about 42%, about 45%, about 47%, about 50%, about 52%, about 55%, about 57%, about 60%, about 62%, about 65%, about 67%, about 70%, about 72%, about 75%, about 77%, about 80%, about 82%, about 85%, about 87%, about 90%, about 92%, about 95%, about 97%, about 100%, about 102%, about 105%, about 107%, about 110%, about 112%, about 115%, about 117%, about 120%, about 122%, about 125%, about 127%, about 130%, about 132%, about 135%, about 137%, about 140%, about 142%, about 145%, and about 147%.

In still further aspects, the formed by the methods disclosed herein compositions can exhibit a modulus of about 1 to about 10 MPa in a dry state as measured according to ASTM D412A, including exemplary values of about 2 MPa, about 3 MPa, about 4 MPa, about 5 MPa, about 6 MPa, about 7 MPa, about 8 MPa, and about 9 MPa.

In still further aspects, the formed by the methods disclosed herein composition can exhibit a lap shear strength of greater than about 30 kPa, greater than about 35 kPa, greater than about 40 kPa, greater than about 45 kPa, greater than about 50 kPa, greater than about 55 kPa, or greater than about 60 kPa, as measured according to a modified ASTM D1002-05 method.

In still further aspects, the formed by the methods disclosed herein composition can exhibit a higher cytocompatibility as measured against human mesenchymal stem cells when compared to a substantially identical reference composition with an absence of the metal oxide. In still further aspects, the composition exhibits an increased inhibition against *S. aureus* and *E. coli* when compared to a substantially identical reference composition in the absence of the metal oxide.

In still further aspects, when the compositions are self-setting compositions, the composition is let to set for the disclosed above times. In the aspects where the methods comprise forming self-setting compositions, the methods further comprise adding any of the disclosed above additional fillers.

In still further aspects, the methods comprise adding at least one pharmaceutically active component to the formed composition.

In still further aspects, the method can comprise adding a porogen to the metal oxide/polymer mixture. In some aspects, the method further comprises forming a film or mold from the metal oxide/polymer mixture. In some aspects, the method further comprises injecting the metal oxide/polymer mixture into a void, e.g., an orthopedic void. In some aspects, the method further comprises evaporating the liquid or a solvent of the metal oxide/polymer mixture. In some aspects, the method further comprises thermally crosslinking the metal oxide/polymer mixture, e.g., after the liquid or a solvent of the metal oxide/polymer mixture is evaporated.

In some aspects, the disclosure also provides a method of additive manufacturing that comprises forming a plurality of layers of a three-dimensional object from any of the disclosed above compositions.

In some aspects, the disclosure also provides a method of filling a void that comprises injecting any of the disclosed above compositions into the void, e.g., an orthopedic void, such as a fracture.

In some aspects, the present disclosure also provides a method of adhering a biological tissue, comprising: a) disposing any of the disclosed herein compositions between a first portion of biological tissue and a second portion of biological tissue; and b) contacting the first portion of biological tissue with the second portion of biological tissue.

In yet further aspects, disclosed herein is a method of treating disease, comprising disposing the composition comprising at least one pharmaceutically active within the biological body, wherein the at least one pharmaceutically active component is active towards the disease and is configured to be released into the biological body at a predetermined time.

Still further disclosed herein are methods of promoting a biological tissue growth comprising providing a scaffold comprising any of the disclosed above compositions and disposing the scaffold in a tissue growth media.

Also disclosed herein are methods of delivering at least one pharmaceutically active component in an efficient amount wherein the method comprises: a) incorporating the at least one pharmaceutically active component into a composition comprising: i) a polymerization product of one or more monomers of Formula (I) and one or more units of a block copolymer comprising one or more monomers of Formula (II), and/or Formula (II'), one or more monomers of Formula (III), and/or optionally one or more compounds of Formula (IV):

(I)

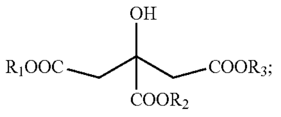

(II)

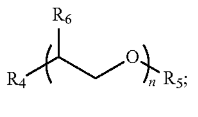

-continued (II')

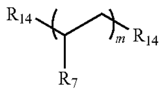

(III)

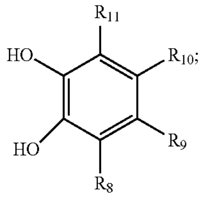

(IV)

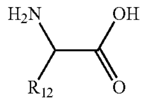

Wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; Re is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m, are independently integers from 1 to 20; $R_{12}$ is an amino acid side chain; $R_{14}$ is —OH or —$NH_2$; and wherein the polymerization product does not comprise metal cations; and ii) a first crosslinking initiator having a formula $A_{b'}O_{a'}$, wherein A is a monovalent, divalent, or trivalent metallic cation and wherein a' and b'' are dependent on the valency of A; wherein A is not a transition metal cation and wherein the first crosslinking initiator is configured to crosslink the reaction product to form the crosslinked composition; and wherein the crosslinked composition is a polymer network having at least one crosslink comprising two catechol moieties directly and covalently coupled to each other; wherein the crosslinked composition is a hydrogel or an organogel and is an adhesive composition; b) releasing the at least one pharmaceutical agent into a biological body at a predetermined time.

In such aspects, any of the disclosed above compounds and monomers can be utilized.

Also disclosed herein are kits for adhering a biological tissue comprising any of the disclosed herein the crosslinked compositions.

EXAMPLES

The following examples are put forth so as to provide those of ordinary skill in the art with a complete disclosure and description of how the compounds, compositions, articles, devices and/or methods claimed herein are made and evaluated and are intended to be purely exemplary and are not intended to limit the disclosure. Efforts have been made to ensure accuracy with respect to numbers (e.g., amounts, temperature, etc.), but some errors and deviations should be accounted for.

Materials

All reagents and solvents, including magnesium oxide (MgO, Lot #MKBS7178V, ~325 mesh), poly(ethylene glycol)-block-poly(propylene glycol)-block-poly(ethylene glycol) (PEG-PPG-PEG, Pluronic® L-31, with an average molecular weight of 1100 Da), and dopamine, were purchased from Sigma-Aldrich and used without further purification unless otherwise specified.

Synthesis and Characterization of IC-EPE Prepolymers

The iC-EPE prepolymer was synthesized by the polycondensation of citric acid (CA), PEG-PPG-PEG, and dopamine (DP), as reported previously (FIG. 1A). Briefly, CA, PEG-PPG-PEG, and DP (molar ratio=1.2:1.0:0.3) were placed in a one-necked round-bottom flask equipped with a vacuum stopper, and the mixture was heated to 160° C. under stirring until complete melting was observed. Then, the temperature was reduced to 140° C. and the reaction was continued under vacuum until the stir bar stopped turning at 60 rpm. The reaction mixture was dissolved in ethanol and precipitated in extensive deionized (DI) water and then was lyophilized to obtain the purified iC-EPE prepolymer.

Fourier transform infrared (FTIR) spectra of iC-EPE and normal iC-$P_{400}$ (iCMBA-$P_{400}D_{0.3}$, synthesized as known in the art, for example, according to M. Mehdizadeh, et al., "Injectable citrate-based mussel-inspired tissue bioadhesives with high wet strength for sutureless wound closure," Biomaterials 33 (32) (2012) 7972-7983; J. Guo et al., "Click chemistry improved wet adhesion strength of mussel-inspired citrate-based antimicrobial bioadhesives," Biomaterials 112 (2017) 275-286), were obtained with a Nicolet 6700 FTIR spectrometer to characterize the functional groups of the prepolymers. Prepolymer solutions in acetone were cast onto KBr plates, and the solvent was evaporated, with blank KBr used as background. $^{1}$H-NMR spectra of prepolymers in DMSO-$d_6$ were recorded on a 300 MHz Bruker DPX-300 FT-NMR spectrometer. The dopamine content of prepolymer was determined by UV-vis spectra using a Shimadzu UV-2450 spectrophotometer with a minimum wavelength resolution of 0.2 nm.

Preparation of IC-EPE/MGO Composite Hydrogels and Gel Time Test

The iC-EPE prepolymer was dissolved in mixed solution (ethanol: DI water=80:20, w/w) to form a 40 wt % polymer solution, and then 5, 10, 15, or 20 wt % (weight percent to dry polymer (dry polymerization product)) of MgO powder was dispersed in DI water, ethanol or sodium periodate (PI) solution (dissolved in DI water) and used as crosslink initiator. iC-EPE/MgO composite hydrogels were fabricated by mixing polymer solution and MgO dispersion with a volume ratio of 2:1. Unless specified otherwise, all hydrogels were allowed to cure for 24 hours and then freeze-dried for at least 2 days for further characterization. The gel times of different samples were measured via a tilting test. For each sample, testing was conducted three times to obtain the average values.

The sample names of iC-EPE prepolymer crosslinked by different amounts of MgO, different solvent/solution used to disperse MgO, and with/without PI, are shown in Table 1. Table 1 shows the nomenclature of different iC-EPE composite hydrogels crosslinked by different MgO contents, different MgO dispersing solvent/solution, and with/without sodium (meta) periodate (PI). These composite hydrogels were all crosslinked at room temperature.

TABLE 1

Nomenclature of different iC-EPE composite hydrogels

| Sample [a] | W5/10/15/20 | E5/10/15/20 | 8PI | W5/10/15 + 2/4/8 PI |
|---|---|---|---|---|
| MgO (wt %)[b] | 5/10/15/20 | 5/10/15/20 | 0 | 5/10/15 |
| Solvent/ Solution[c] | DI water | Ethanol | 8 wt % PI | 2/4/8 wt % PI |

[a] To crosslink iC-EPE prepolymer, the iC-EPE prepolymer was dissolved in ethanol/water (80/20, w/w) into a 40 wt % solution, and MgO was dispersed in the solvent/solution as shown in the table. The volume ratios between polymer solution and MgO dispersion were all 2/1 (v/v);

[b]MgO to composite ratio, MgO was dispersed in water (W), ethanol (E), PI solution, or the combination of MgO and PI in water. W5/10/15/20 are a series of hydrogels of W5, W10, W15, and W20, similar to the others.

Rheological Testing of IC-EPE/MGO Composite Hydrogels

Rheological tests were carried out using a Discovery Series Hybrid Rheometer (DHR-1, TA Instruments, USA) in a parallel plate configuration, employing sandblasted stainless steel 40 mm diameter plates throughout and a Peltier plate for temperature control. 2 mL iC-EPE prepolymer solution (40 wt %) and 1 ml crosslink initiator dispersion (10 wt % MgO dispersed in DI water, ethanol, or 8 wt % PI solution) was mixed, and the mixture was immediately deposited on the lower plate of the rheometer. The upper plate was immediately brought down to a gap distance of 40 μm, and both storage (G') and loss (G") modulus values as a function of time were determined at a frequency of 1 Hz and a strain of 1%. Each measurement was performed three times. The gel time was approximated by the G'/G" crossover time.

Characterization of Physical Properties of IC-EPE/MGO Composite Hydrogels

Mechanical properties of dried iC-EPE composite hydrogel films were determined on an Instron 5966 machine with a 1 kN (for dried films) or 10 N (for swollen films) load cell (Instron, Norwood, MA) according to ASTM D412A. Dumbbell-shape samples (25 mm×6 mm×1.5 mm, length×width×thickness) were pulled to failure under a strain rate of 500 mm/min. Elastic modulus, tensile stress, and elongation at break were recorded for various films as the average of eight repeats. In order to evaluate the effect of hydration on the mechanical properties of iC-EPE composite hydrogels, the mechanical tests were also conducted on samples after being hydrated in wet conditions for 48 hours.

The sol content and swelling ratio of crosslinked iC-EPE/MgO composite hydrogels were measured according to the known in the art procedures and then calculated using equations (1) and (2), respectively.

$$\text{Sol content } (\%) = \frac{W_i - W_d}{W_i} \times 100 \quad (1)$$

$$\text{Swelling ratio } (\%) = \frac{W_s - W_d}{W_d} \times 100 \quad (2)$$

where $W_i$ denotes the initial mass of dry iC-EPE hydrogel sample, $W_d$ represents the mass of the freeze-dried sample after leaching the uncrosslinked part with 1, 4-dioxane for 48 hours, and W, represents the mass of network sample blotted dry with filter paper after suspending in water for 24 hours.

Degradation profiles were evaluated by in vitro degradation in phosphate-buffered saline (PBS, pH 7.4, 01 M) at 37° C. Disc specimens (7 mm in diameter, 1 mm thick) were accurately weighed ($W_0$) and then were immersed in 10 mL of PBS and incubated at 37° C. The PBS solution was changed every other day. At a predetermined time point, samples were thoroughly washed with DI water and freeze-dried to determine the residual mass ($W_t$). Mass loss was calculated using equation (3):

$$\text{Mass loss (\%)} = \frac{W_0 - W_t}{W_0} \times 100 \quad (3)$$

Adhesion Strength of IC-EPE/MGO Composite Hydrogels

The adhesion strength of iC-EPE composite hydrogels was determined by the lap shear strength test according to the modified ASTM D1002-05 method. Porcine-derived, acellular small intestine submucosa (SIS) material (OASIS®, HealthPoint Ltd. Fort Worth, TX) was cut into 40 mm×4 mm strips and hydrated in PBS for at least 1 hour before testing. After mixing the iC-EPE polymer solution with predetermined amounts of crosslink initiator, 10 μL of the mixture was added and spread over one end of a strip. A second wet strip was subsequently placed in contact with the first one to form an overlapping area of 6 mm×4 mm. The adhered strips were compressed with a 100 g weight for 20 minutes and then were placed in a highly humid chamber for 2 hours prior to testing. The lap shear strength of bonded strips was subsequently measured using Instron 5966 fitted with a 10 N load cell at a rate of 1.3 mm/min. The lap shear strength of fibrin glue (Tisseel, Baxter healthcare Corp.) was used for comparison.

In Vitro Biocompatibility Tests

The in vitro biocompatibility of the crosslinked iC-EPE/MgO composite hydrogels was assessed by testing cell cytotoxicity of the sol content (or leachable fraction) and degradation products. Human-derived mesenchymal stem cells (hMSC, ATCC® PCS-500-012TM, from ATCC, passage 5-10) were used.

The cytotoxicity of the sol content of crosslinked iC-EPE/MgO composite hydrogels was also studied using MTT (methylthiazolyl-diphenyl-tetrazolium bromide) assay against hMSCs. The leachant (sol content) solution of the hydrogel was obtained by incubating 0.5 g dried hydrogel specimens in 5 mL of PBS (pH 7.4) at 37° C. for 24 hours. Next, three different dilutions were prepared: 1×, 10× and 100× (1× was the solution of leached products without dilution, 10× and 100× were times and 100 times diluted from 1× solution with PBS, respectively). To each well of a 96-well cell culture plate, 200 μL of hMSC solution in MG medium with a density of $5\times10^4$ cells/mL was added and incubated for 24 hours. Then, 20 μL of sol content solution with various concentrations was added, and the cells were incubated for another 24 hours, followed by MTT assay.

The cytotoxicity of degradation products of hydrogels was also evaluated. Equal weight (1 g) of dried iC-EPE/MgO hydrogel samples, as well as FDA (Food and Drug Administration)-approved poly (lactic-co-glycolic acid) (PLGA, used as a control, LA/GA=50/50, Mw~60 KDa, purchased from Polyscitech), were fully degraded in 10 mL of 0.2 M NaOH solution. After adjusting pH to 7.4, the resultant solutions were diluted to three concentrations (1×, 10× and 100×) using PBS (pH 7.4) and used for cell culture (the process was the same as used in the sol content cell cytotoxicity study described above) and subsequent MTT analysis.

Cell adhesion and proliferation on iC-EPE composite hydrogels films were also studied against hMSC cells, and the cell morphology was observed by Live/Dead staining assay, using W10 as an example. Briefly, 20 μL of iC-EPE prepolymer solution was mixed with 10 μL of MgO DI water solution (0.088 g/mL), and the mixture was uniformly spread on the surface of a glass slide to form a thin film of W10 with a diameter of 15 mm prior to completion of crosslinking. Then the samples were sterilized by incubation in 70% ethanol for 24 hours, followed by exposure to UV light for 3 hours. After that, the samples were placed in 24-well plates and seeded with 500 μL hMSC solution with a density of 5,000 cells/$cm^2$, followed by MG media replacement the next day. At predetermined time points (cells were incubated for 1, 3 and 7 days), the medium was removed from the well plate, and the cells were washed with PBS then stained by Live/Dead Viability/Cytotoxicity Kit (Invitrogen, molecular probes, Eugene, OR) for the observation of cell morphology using an inverted light microscope (Nikon Eclipse Ti-U) equipped with an ANDOR DL-604M-#VP camera and Prior Lumen 200.

In Vitro Anti-Bacterial Properties of IC-EPE Bioadhesives

The antibacterial properties of iC-EPE composite hydrogels were tested against *Staphylococcus aureus* (*S. aureus*) and *Escherichia coli* (*E. coli*) as positive and negative bacteria models, respectively. *S. aureus* (ATCC® 6538TM) and *E. coli* (ATCC® 25922TM) were purchased from ATCC (American Type Culture Collection) and used according to established safety protocols. Tryptic soy broth (Cat. #: C7141) and tryptic soy agar (Cat. #: C7121) used for *S. aureus* culture were purchased from Criterion (via VWR). Luria broth base (LB broth, Cat. #: 12795-027) and select agar (Cat. #: 30391-023) used for *E. coli* culture were purchased from Invitrogen. *S. aureus* and *E. coli* monocolonies were incubated in sterilized tryptic soy broth and LB broth, respectively, at 37° C. on an orbital shaker overnight and the obtained bacteria suspensions were diluted to desired concentrations prior to use.

W10, E10, W10+8PI, and 8PI were selected as the representative experimental samples, and PEGDA/HEMA (w/w=1/1) was used as a positive control. Firstly, bacteria suspension with an optical density (OD) of 0.07 at 600 nm was prepared. Then the bacteria suspension was diluted with broth medium 100 times to obtain the expected concentration. Colony counting was conducted to determine the bacteria concentration in CFUs (colony forming units) per milliliter. 0.2 g of freeze-dried samples (without removing leachable components) were immersed in 20 ml of the above bacteria suspension and incubated at 37° C. for 24 hours on an orbital shaker. After that, the diluted medium was cast on an agar plate for colony counting. Bacteria growth broth was also tested and served as a negative control. The bacterial inhibition ratios of samples were calculated by equation (4):

$$\text{Inhibition ratio (\%)} = 100 - 100 \times \frac{N_t - N_0}{N_{con} - N_0} \quad (4)$$

where $N_0$ was the bacteria concentration in broth medium before incubation in the unit of CFUs/mL. $N_t$ and $N_{con}$ were the bacteria concentration of broth containing hydrogels and pure broth (control) after incubation for 24 hours, respectively, also in the unit of CFUs/mL.

In Vivo Study

Skin incisions were made on Sprague-Dawley rats (female, 260±50 g, n=5) to evaluate the in vivo biocompatibility and wound healing performance of iC-EPE crosslinked by MgO (10 wt % in water, W10). All in vivo experiments were performed with the approval of the Third Military Medical University, China. Briefly, the rats were anesthetized using 40 mg/kg of ketamine, and the hair on the dorsal side was shaved. The skin surgical area on the dorsum was sterilized with 75% ethanol, and then whole-layer surgical skin injuries were created (2 cm long×0.5 cm deep). The sterilized iC-EPE was mixed with MgO (W10), and the adhesive was dropped into the wounds, followed by finger-clamping for 5 min. In parallel, conventional sutures were used as a positive control. On the $7^{th}$ and $28^{th}$ day post-administration, the treated skin wounds were harvested and fixed with 4% paraformaldehyde for histological study. Hematoxylin and eosin (H&E) staining and Masson trichrome staining were performed to assess the morphology and collagen production, respectively. Immunohistochemistry for CD11 b expression was also performed to evaluate inflammation. CD11 b positive cells in the tissues were detected using rabbit anti-rat Integrin aM (H-61, Santa) and peroxidase-conjugated goat anti-rabbit secondary antibodies (Santa). The stained tissue sections were observed by light microscopy (Nikon, Tokyo, Japan). At different time points after treatment, the number of cells infiltrating into the incision area and the number of CD11 b positive cells were calculated in random areas using Image J. Collagen density (%) was determined by calculating the ratio of blue-stained area to a total area of Masson trichrome staining images using Image J. At least five random areas were selected, and the results were averaged.

Statistical Analysis

All data are presented as mean±standard deviation, with a tested sample number of at least 5. The significance of differences between results was evaluated by the One-Way ANOVA test. A p-value<0.05 (*) was considered to be statistically significant.

Example 1

Synthesis and Characterization of iC-EPE Prepolymers

Figure 2A:
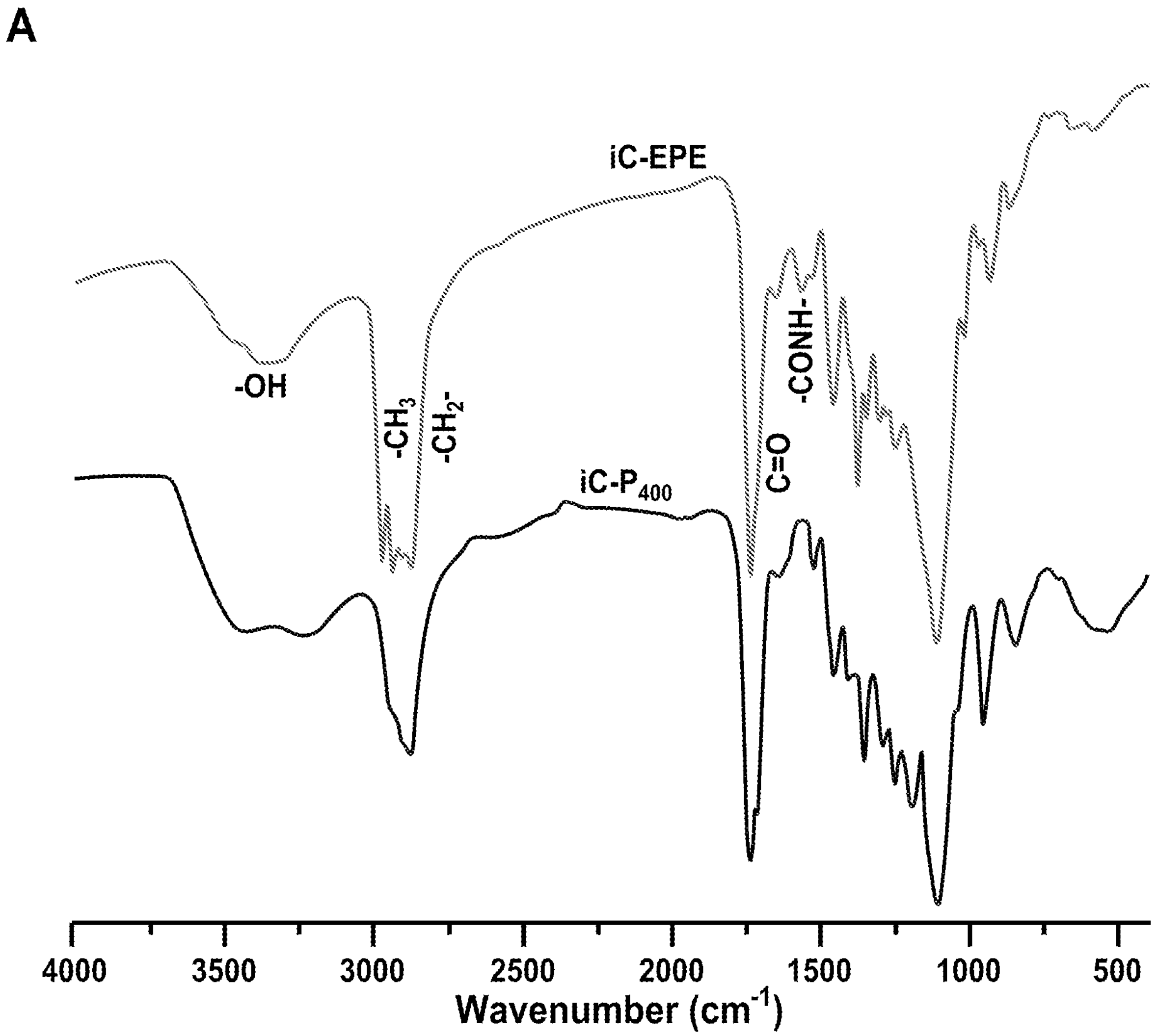
FIGS. 2A-2C show characterization of prepolymers: FTIR (FIG. 2A), $^1$H-NMR (FIG. 2B) and UV-vis absorption spectra (FIG. 2C) of 0.4 mg/mL of iC-EPE and iC-$P_{400}$ (iCMBA composed of citric acid, poly(ethylene glycol) with a molecular weight of 400 Da ($PEG_{400}$), and dopamine) in ethanol/water mixed solvent (w/w=40/60). The insert panel in FIG. 2C is the standard curve of dopamine in a mixed ethanol/water solvent (w/w=40/60).
Figures 2B, 2C:
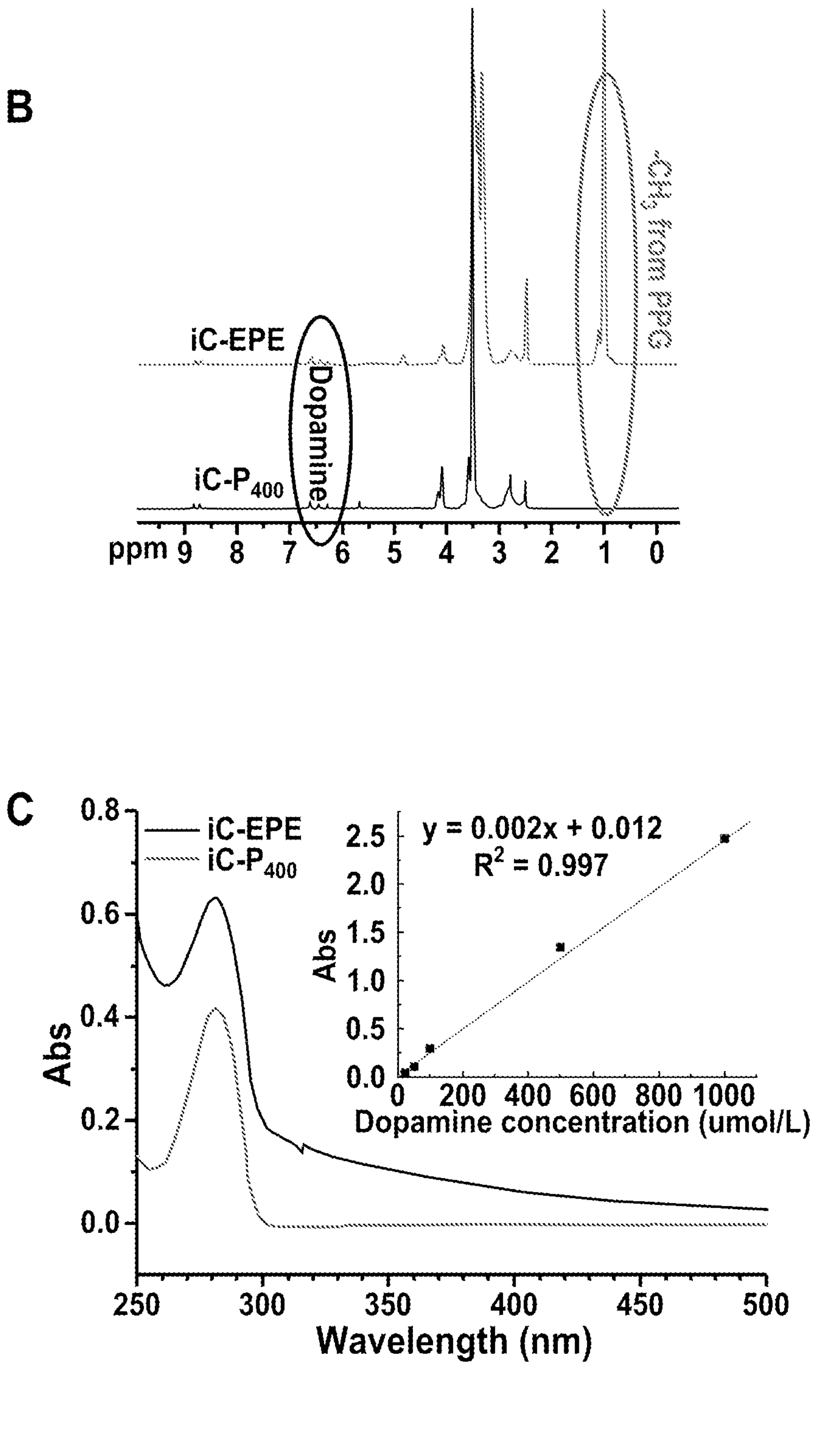

Original iCMBAs used hydrophilic PEG diols to confer water solubility. Thus, and as known, such crosslinked hydrogels possessed very high water swelling ratios, in extreme cases >1000 wt %. To reduce the swelling ratio, more hydrophobic PEG-PPG-PEG (EPE) was used to react with CA and dopamine via a convenient one-pot polycondensation to produce iC-EPE prepolymer (FIG. 1A). FTIR spectra of iC-EPE and iC-$P_{400}$ (synthesized using $PEG_{400}$, for comparison) prepolymers are shown in FIG. 2A. The peak between 1700 and 1748 $cm^{-1}$ was assigned to the carbonyl group (C═O) in the ester group. The peak at 1540 $cm^{-1}$ was assigned to the amide group (—C(═O)—NH—), which confirmed the formation of amide linkages between the —COOH groups of CA and —$NH_2$ groups of dopamine. The peaks around 2932 $cm^{-1}$ and 2870 $cm^{-1}$ were assigned to methyl (—$CH_3$) and methylene (—$CH_2$—) groups from PEG-PPG-PEG, respectively. The relatively broad peak at 3364 $cm^{-1}$ was ascribed to the presence of hydroxyl groups. The $^1$H-NMR spectra of iC-EPE and iC-$P_{400}$ are shown in FIG. 2B. The peak at 1.02 ppm in the iC-EPE spectrum not present in the $^1$H-NMR spectrum of iC-$P_{400}$ was assigned to the protons of —$CH_3$ from EPE, the most characteristic peak of iC-EPE. The multiple peaks between 2.55 and 2.90 ppm were assigned to the protons in methylene groups from citric acid and dopamine. The chemical shifts at 6.40-6.70 ppm shown in the spectra of both iC-EPE and iC-$P_{400}$ prepolymers were assigned to the protons of the phenyl group, characteristic of the catechol group. The FTIR and $^1$H-NMR data further confirm the esterification reaction between CA and EPE and the formation of amide linkages between the —COOH groups of CA and dopamine's —$NH_2$ group. The UV-vis spectrum further verifies the availability of catechol hydroxyl groups in the iC-EPE prepolymer via the UV absorption peak at 280 nm (FIG. 2C). Dopamine content in the iC-EPE prepolymer was determined to be 0.308 mmol/g according to the dopamine standard curve shown in the insert panel in FIG. 2C.

Example 2

Preparation of iC-EPE/MgO Composite Hydrogels and Gel Time Measurement

Catechol mediated crosslinking of polymers often utilize harsh and toxic water-based oxidants, such as sodium (meta) periodate (PI), silver nitrate (SN), or $FeCl_3$. Alternatively, enzymes such as horseradish peroxidase (HRP) and mushroom tyrosinase (MT), while effective when used in the crosslinking of tyramine or tyrosine containing polymers, display long crosslinking times up to several hours and often require large amounts of enzyme, thus reducing both practicality and cost-effectiveness in such systems. Currently, there are a few reports for effective crosslinking of catechol group-containing polymers without the use of toxic oxidants.

Figure 1B:
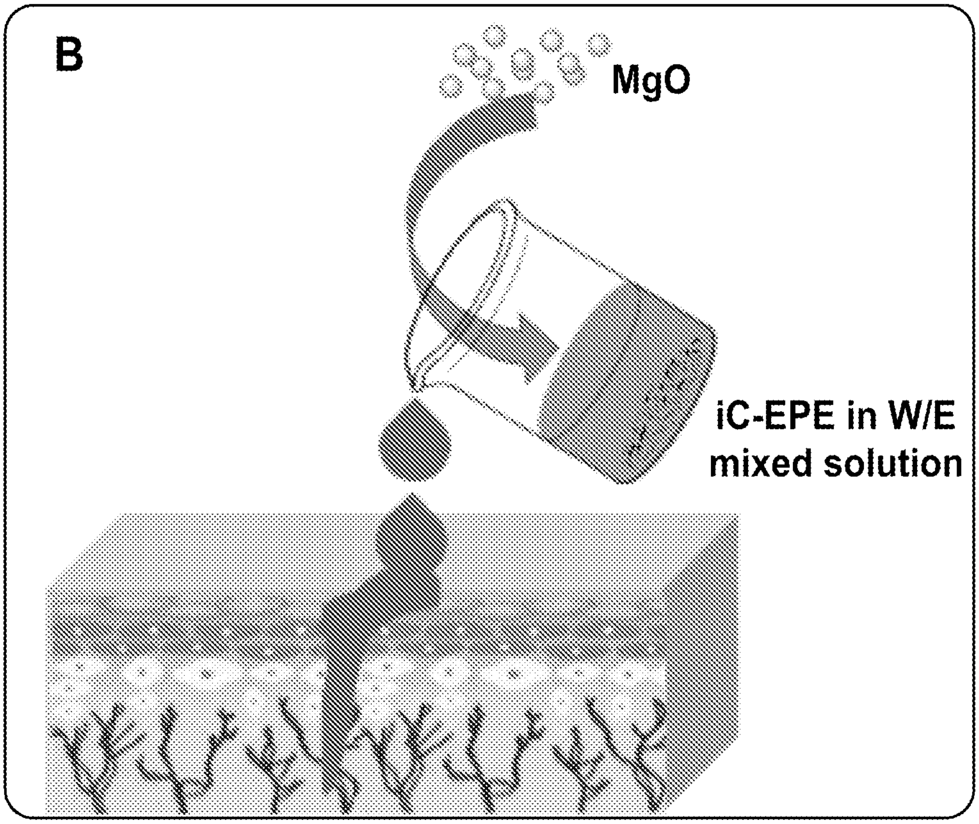
Figure 4:
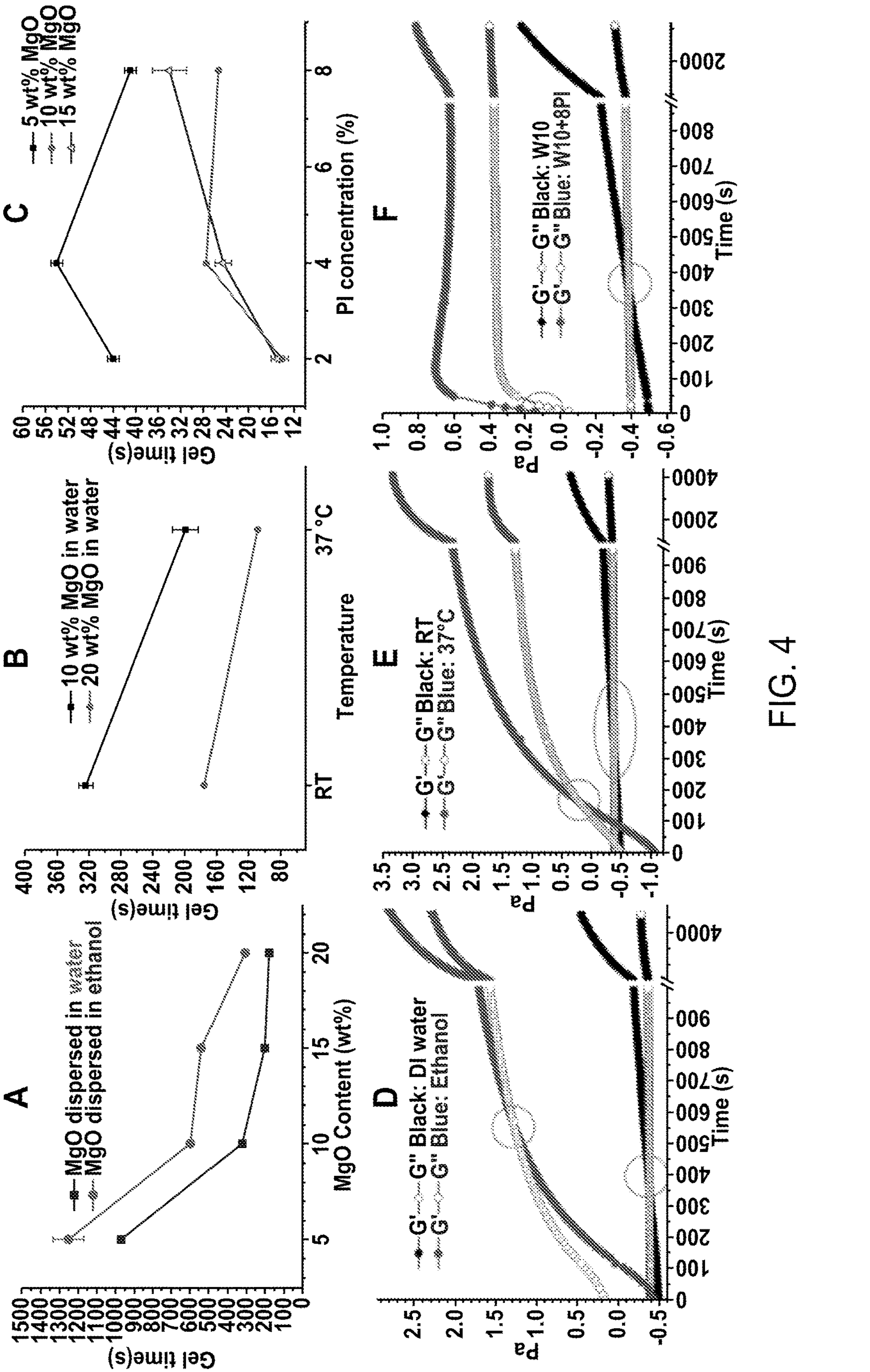
FIGS. 4A-4F depict gelation (Gel) time determination: Gel times (obtained by a tilting test) of iC-EPE crosslinked by MgO at different MgO concentrations (FIG. 4A), different temperatures (FIG. 4B), and different MgO/PI concentrations in water (FIG. 4C); Representative results of rheology tests for iC-EPE crosslinked by 10 wt % MgO dispersions in different solvents (ethanol or water, FIG. 4D), at different temperatures (MgO was dispersed in water, FIG. 4E), or crosslinked by mixed solutions of MgO and 8 wt % PI (FIG. 4F). The gel time was determined by the crossover point (red circle) of storage modulus (G') and loss modulus (G").

Here, it was found that MgO particles are capable of crosslinking iC-EPE or other iCMBAs by simply mixing them with MgO dispersions in water or ethanol (FIG. 1B). The effects of MgO content on the gel time of iC-EPE/MgO composite hydrogels are shown in FIG. 4A and Table 1. Gel time decreased with the increase of MgO content. Moreover, for the same MgO content, MgO dispersed in water crosslinked iC-EPE prepolymer faster than the equivalent amount of MgO dispersed in ethanol. The effects of temperature on gel time are shown in FIG. 4B. For equivalent MgO content, increased temperature resulted in an obvious decrease in gel time. For example, at 10 wt % MgO, the gel time decreased from 324 s at 25° C. (room temperature, RT) to 176 s at 37° C. (human body temperature). The gel times of MgO-induced iC-EPE crosslinking were in the range of 200 to 1300 s (FIGS. 4A-4B), with most gel times decreased compared to the gel time of iC-EPE crosslinked by pure 8 wt % PI (1568±47s, Table 1), and comparable to the gel times of the known iCMBAs crosslinked by PI When mixing MgO and PI together in water, gel times significantly decreased to less than 60 s for all tested samples (FIG. 4C and Table 1). When the MgO content was kept the same, 2 wt % PI led to the fastest crosslinking, while further increasing PI concentration did not induce faster crosslinking. Without wishing to be bound by any theory, it was hypothesized that such an effect is due to the mutual inhibition between MgO and PI. It was further hypothesized that when the PI concentration was 2 wt %, it has promoted the crosslinking of iC-EPE prepolymer by MgO, but when the PI concentration increased to 4 wt %, the mutual inhibition effect between MgO and PI became more prominent. When the PI concentration increased to 8 wt %, compared to that of 4 wt % PI, the gel time decreased again, except in the case of W15+8PI (W15 is defined as 15 wt % of MgO/composite with water as dispersion media for MgO particles, the nomenclature of different iC-EPE composite hydrogels are listed in Table 1), which, without wishing to be bound by any theory, was attributed to relatively increased PI-induced crosslinking over MgO-induced crosslinking (FIG. 4C).

Rheology tests were conducted using representative samples, and the crossover points of the curves of storage modulus (G') and loss modulus (G") were determined to be the gel times (red circles in FIG. 4D-4F). The gel times determined by rheology tests were comparable to those determined by tilting tests, proving that tilting tests are reliable and more convenient and easier to implement. From FIG. 4D, it can be seen that with the same amount of MgO used (10 wt % MgO), when the dispersion solvent of MgO was changed from ethanol to water, the gel time reduced from 558 s to 386 s, which is in agreement with the results from the tilting test results (FIG. 4A). FIG. 4E further confirmed the same trend shown in FIG. 4B that the increase in temperature from RT (25° C.) to 37° C. led to a decrease in gel time. The synergistic effects between MgO and PI were also further confirmed by FIG. 4F that the gel time was vastly reduced from 386 s (W10, using 10 wt % MgO in water) to less than 10 s for W10+8PI (using 10 wt % MgO dispersed in 8 wt % PI solution).

Example 3

Multifaceted MgO Crosslinking Mechanism

Figure 3:
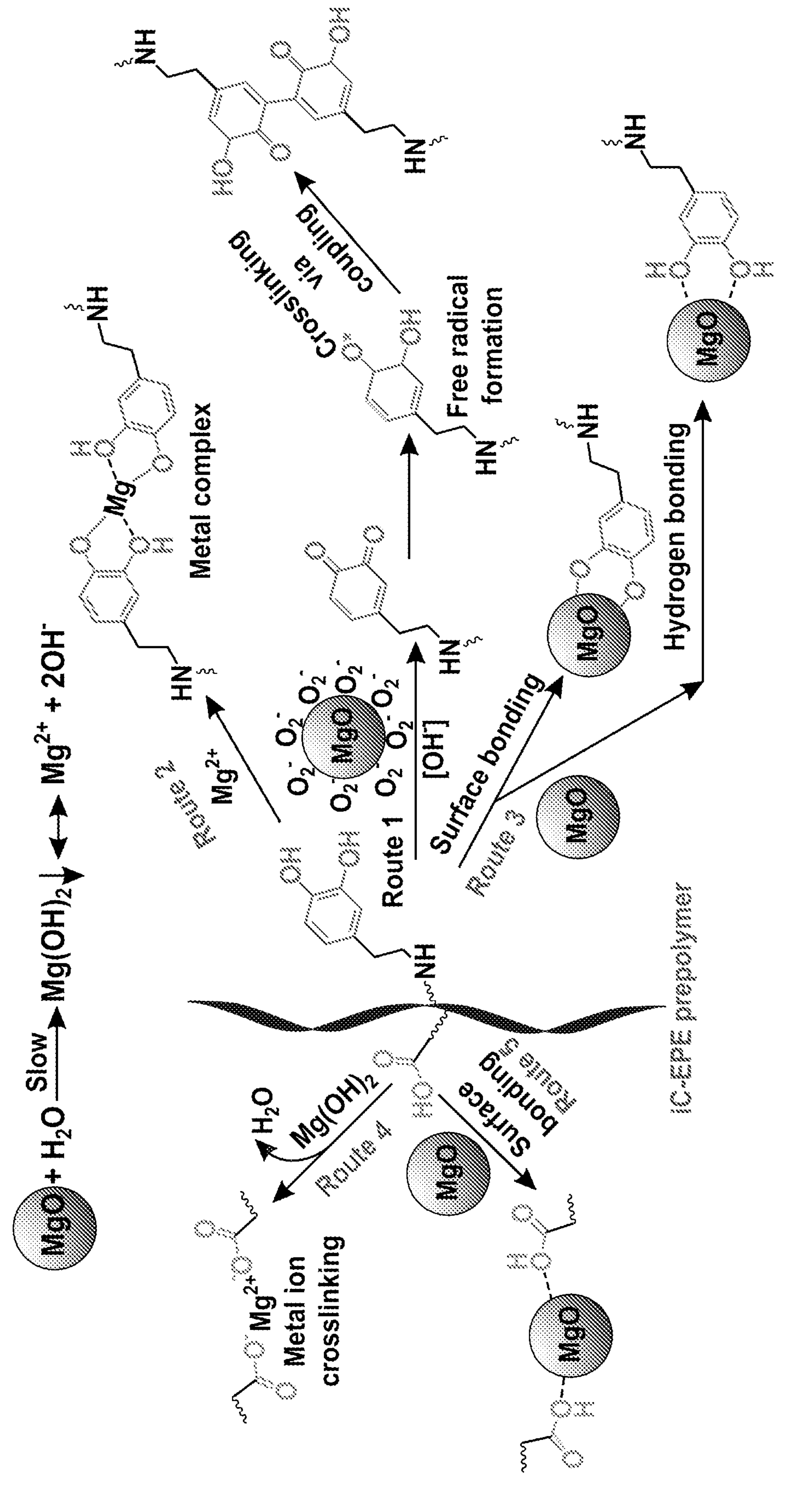
FIG. 3 depicts multifaceted crosslinking mechanisms of iC-EPE by MgO.

The possible crosslinking mechanisms of MgO are exhibited in FIG. 3. Without wishing to be bound by any theory, the slow reaction between MgO and water to create a moderate alkaline condition was assumed to be a significant step (FIG. 3). This could be deduced from the fact that without using any water in the formulation (with iC-EPE dissolved in ethanol and MgO dispersed in ethanol), iC-EPE/MgO could not crosslink while using more water in the formula led to faster crosslinking (Table 2 and FIGS. 4A-4F).

TABLE 2

Gel times of iC-EPE prepolymer crosslinked by MgO, PI, or MgO + PI, at different MgO concentrations, choices of solvents (water (W) or ethanol (E)), and temperature (25 or 37° C.) with/without PI.

| Prepolymer [a] | MgO to composite ratio (wt %) [b] | Testing temperature (° C.) | Measured gel time (s) MgO dispersion solvent/solution: Water (W) | Ethanol (E) | 8 wt % PI solution |
|---|---|---|---|---|---|
| | 0 | | | | 1568 ± 47 |
| | 5 | | | | (8PI)[c] |
| iC-EPE in | 10 | 25 | 969 ± 19 | 1251 ± 83 | 41 ± 1 |
| water/ethanol | 15 | | (W5)[c] | (E5)[c] | (W5 + 8PI)[c] |
| (80/20, w/w) | 20 | | 324 ± 9 | 599 ± 3 | 25.5 ± 0.5 |
| | | | (W10)[c] | (E10)[c] | (W10 + 8PI)[c] |
| | | | 204 ± 9 | 540 ± 10 | |
| | | | (W15)[c] | (E15)[c] | 34 ± 3 |
| | | | 176 ± 2 | 307 ± 13 | (W15 + 8PI)[c] |
| | | | (W20)[c] | (E20)[c] | |
| | 10 | 37 | 199 ± 16 | 348 ± 2 | |
| | 20 | | 109 ± 5 | 224 ± 10 | |
| iC-EPE in ethanol | 10 | 25 | | Un-crosslinkable | |

[a] The iC-EPE prepolymer was dissolved in ethanol/water mixed solution (80/20, w/w) into a 40 wt % solution;

[b] The volume ratios between polymer solution and MgO dispersion were all 2/1 (v/v);

[c] The labels in the parentheses are the sample names of crosslinked iC-EPE composite hydrogels.

Without wishing to be bound by any theory, it was hypothesized that the crosslinking mechanism of iC-EPE/MgO adhesives could be multifaceted:

The reactive oxygen species (ROS), such as strong oxidative superoxide anions ($O_2^-$), on the surface of MgO particles, induced the oxidation of catechol groups at alkaline conditions followed by free radical formation and crosslinking through coupling (route 1 in FIG. 3). The crystal defects of MgO particles can further facilitate the formation of $O_2^-$ on the surface of MgO. The strong oxidizing capability of $O_2^-$ on the surface of MgO particles at alkaline conditions was also, without wishing to be bound by any theory, considered to be a reason for the antimicrobial activity of MgO. Although the overproduction of ROS at the inflamed area is believed to delay or interfere wound healing process, the inclusion of catechol-containing iC-EPE may serve as a ROS scavenger to reduce the negative effects of ROS to wound healing.

Without wishing to be bound by any theory, it was assumed that metal complex formation between magnesium ions ($Mg^{2+}$) and catechol groups could also contribute to the crosslinking (route 2 in FIG. 3).

Further, without wishing to be bound by any theory, it was assumed that since iC-EPE prepolymer also contains free carboxyl (—COOH) groups, the reaction between $Mg(OH)_2$ (or possibly MgO) with —COOH groups and the formation of electrostatic interactions between $Mg^{2+}$ and $—COO^-$ can contribute to crosslinking (route 4 in FIG. 3); however, ion bond formation between $Mg^{2+}$ and $—COO^-$ should be very slow. Such an assumption was supported by the inability to crosslink the —COOH-containing citrate-based prepolymer poly(poly(ethylene glycol) citrate) (PEGC, without catechol groups, synthesized by reacting CA and PEG) with MgO (data not shown).

Again without wishing to be bound by any theory, it was also assumed that the interactions between catechol groups or carboxyl groups with MgO particles through surface bonding or hydrogen bonding (routes 3 and 5 in FIG. 3) can serve as an additional way to crosslink.

In addition to triggering intermolecular crosslinking, oxidized catechol groups (ortho-quinone groups) can also contribute to the strong adhesion to biological surfaces through the formation of covalent bonds with nucleophile groups on tissue surfaces such as —$NH_2$, —SH, —OH and —COOH groups.

Example 4

Properties of Crosslinked iC-EPE

Figure 5:
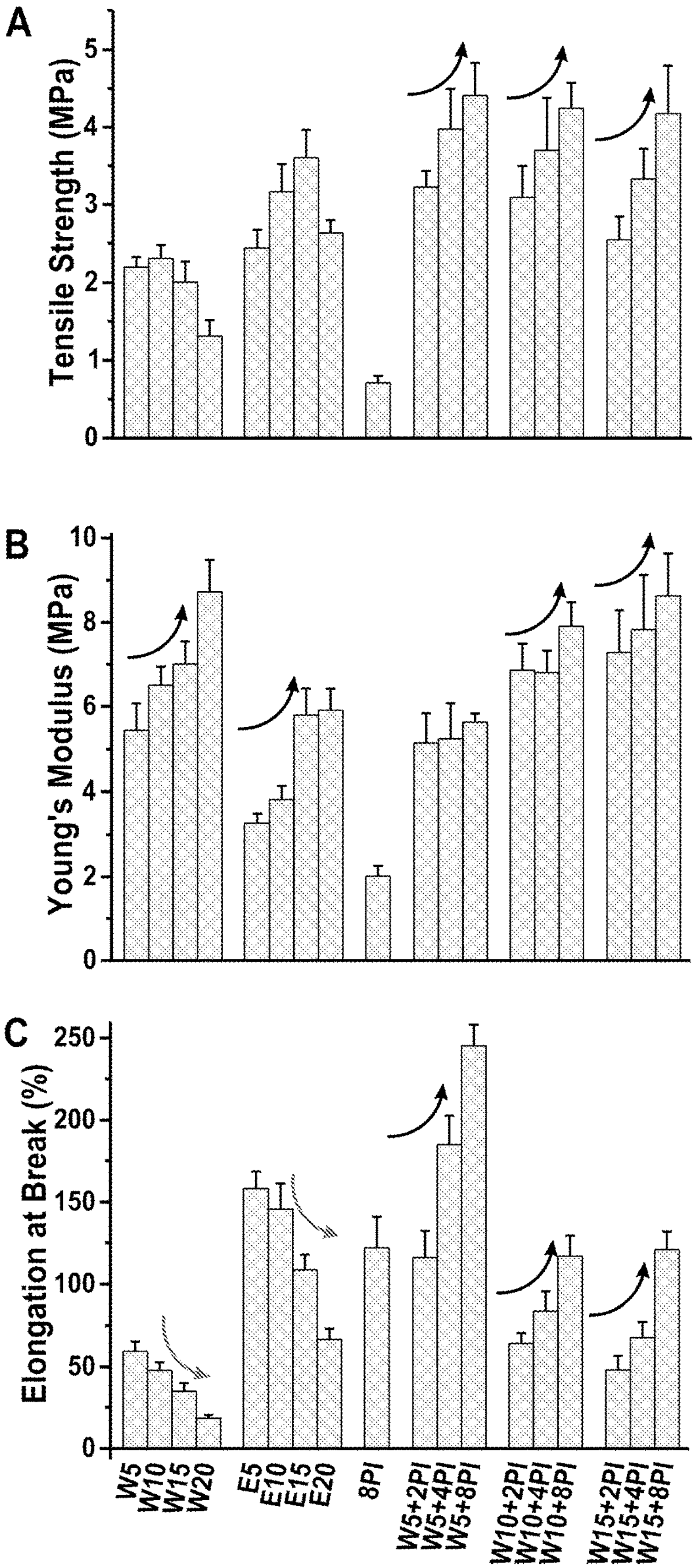
FIGS. 5A-5F depicts characterizations of crosslinked hydrogels: Mechanical, swelling, and degradation properties including tensile strength (FIG. 5A), initial modulus (FIG. 5B), elongation at break (FIG. 5C), sol content (FIG. 5D), swelling ratios (FIG. 5E), and degradation profiles (FIG. 5F) of iC-EPE bioadhesives crosslinked by MgO, MgO+PI or PI.
Figure 5:
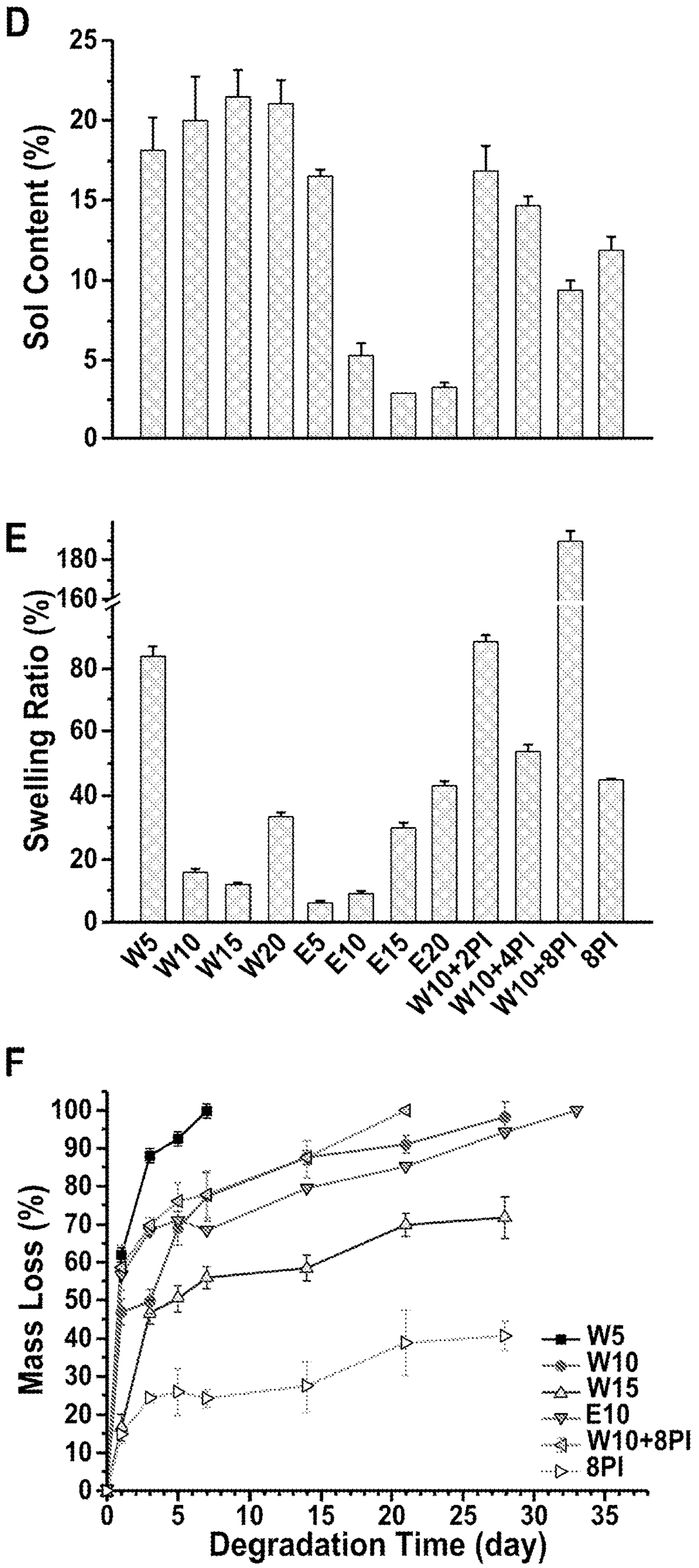

To investigate the mechanical properties of the crosslinked iC-EPE composite hydrogels, tensile tests were carried out at both dry and wet conditions (FIGS. 5A-5F and Table 2). The tensile strengths of dried iC-EPE/MgO composite hydrogels, with/without PI, were in the range of 2 to 5 MPa, comparable with that of the previous iCMBAs crosslinked by PI, which have tensile strengths ranging from 1 to 7.5 MPa. Overall, in the tested formulations, increasing MgO content led to an increase of tensile strengths (FIG. 5A). The elastic moduli (Young's moduli) of crosslinked iC-EPE/MgO hydrogels increased gradually with the increase of the MgO content, whereas the elongation at break decreased (FIGS. 5B-5C). The tensile strengths and moduli of iC-EPE crosslinked by MgO or MgO+PI were much higher than that of the hydrogel crosslinked only by PI, demonstrating that MgO serves not only as a crosslinker but also as a composite filler. The combination of MgO and PI not only enhanced the elastic moduli and tensile strengths but also increased the elongations at break. The stress-strain curves of crosslinked iC-EPE/MgO hydrogels are characteristic of elastomers, which is especially important for soft tissue applications in order to enable mechanical conformity and stress transfer between hydrogels and flexible and dynamic soft tissues (FIG. 5D). The mechanical properties of the crosslinked iC-EPE hydrogels in a wet state are listed in Table 3. It can be seen that tensile strengths decreased when samples were hydrated and swollen. These results suggest that the crosslinked iC-EPE hydrogels have tailorable mechanical properties for various clinical applications.

TABLE 3

Mechanical properties of crosslinked iC-EPE bioadhesives at dry and wet (swollen) states.

| Crosslinked bioadhesives | Tensile Strength (MPa) Dry | Swollen | Elongation at break (%) Dry | Swollen | Modulus (MPa) Dry | Swollen |
|---|---|---|---|---|---|---|
| W5 | 2.19 ± 0.14 | | 59.13 ± 6.22 | | 5.44 ± 0.64 | |
| W10 | 2.30 ± 0.18 | | 47.84 ± 5.04 | | 6.52 ± 0.44 | |
| W15 | 2.00 ± 0.27 | | 35.16 ± 4.77 | | 7.00 ± 0.54 | |
| W20 | 1.31 ± 0.22 | | 18.33 ± 2.63 | | 8.70 ± 0.78 | |
| E5 | 2.43 ± 0.24 | | 157.97 ± 11.00 | | 3.26 ± 0.23 | |
| E10 | 3.16 ± 0.36 | 0.22 ± 0.01 | 145.45 ± 16.04 | 12.71 ± 0.81 | 3.81 ± 0.31 | |
| E15 | 3.60 ± 0.36 | | 108.43 ± 9.50 | | 5.80 ± 0.64 | |
| E20 | 2.63 ± 0.17 | | 182.50 ± 21.74 | | 5.90 ± 0.53 | |
| 8PI | 0.70 ± 0.10 | | 122.13 ± 19.18 | | 1.98 ± 0.27 | |
| W5 + 2PI | 3.22 ± 0.22 | | 115.73 ± 16.7 | | 5.14 ± 0.72 | |
| W5 + 4PI | 3.97 ± 0.53 | | 184.84 ± 17.98 | | 5.24 ± 0.86 | |
| W5 + 8PI | 4.40 ± 0.43 | | 244.8 ± 13.52 | | 5.62 ± 0.23 | |
| W10 + 2PI | 3.09 ± 0.41 | | 64.07 ± 5.63 | | 6.85 ± 0.64 | |
| W10 + 4PI | 3.70 ± 0.68 | | 83.75 ± 11.77 | | 6.75 ± 0.57 | |
| W10 + 8PI | 4.24 ± 0.33 | 0.834 ± 0.12 | 116.47 ± 13.29 | 179.90 ± 14.50 | 7.89 ± 0.58 | 1.50 ± 0.10 |
| W15 + 2PI | 2.55 ± 0.30 | | 48.59 ± 8.30 | | 6.98 ± 0.81 | |
| W15 + 4PI | 3.34 ± 0.38 | | 67.62 ± 9.52 | | 7.82 ± 1.31 | |
| W15 + 8PI | 4.17 ± 0.62 | | 120.36 ± 11.50 | | 8.62 ± 1.03 | |

Sol contents of iC-EPE hydrogels crosslinked by MgO, MgO+PI, or PI are shown in FIG. 5D. The sol contents of the tested formula were all lower than 25%. The hydrogels crosslinked by MgO dispersion in ethanol possessed the lowest sol content, which was much lower than that of the hydrogel crosslinked by MgO dispersion in water or MgO+PI solution. Without wishing to be bound by any theory, it was attributed to the alkalinity of MgO, which could partially destroy the network of the hydrogels. As shown in FIG. 5E, the swelling ratios of iC-EPE hydrogels, crosslinked either by MgO (dispersed in water or ethanol), MgO+PI, or PI, were all lower than 200 wt %, with the lowest <10 wt % (E5). The swelling ratios of EPE based iC formulae were all much lower than that of PEG-based iCMBAs (some >1000 wt %), confirming the benefit of the replacement of hydrophilic PEG with more hydrophobic EPE.

Degradation of the crosslinked iC-EPE composite hydrogels was conducted at 37° C. in PBS and the mass losses at preset time points were recorded (FIG. 5F). iC-EPE hydrogels crosslinked by PI exhibited the slowest degradation rate with less than 40 wt % mass loss after 28 days. The hydrogels crosslinked by 5 wt % MgO dispersion in water exhibited the fastest degradation, with the degradation completed in 7 days. For the hydrogels crosslinked only by MgO, including W5, W10, W15, and E10, the degradation rate decreased with increased MgO content, implying that higher MgO content led to higher crosslinking density. Interestingly, iC-EPE crosslinked by 10 wt % MgO and 8 wt % PI (W10+8PI) degraded much faster than iC-EPE crosslinked only by 8 wt % PI (8PI) or by 10 wt % MgO (W10), supporting the mutual inhibition effect of MgO and PI on the crosslinking of iC-EPE prepolymer. Again, without wishing to be bound by any theory, it was suggested that the alkalinity of MgO in an aqueous solution can also contribute to accelerated degradation.

Example 5

Adhesion Strength

Figure 6:
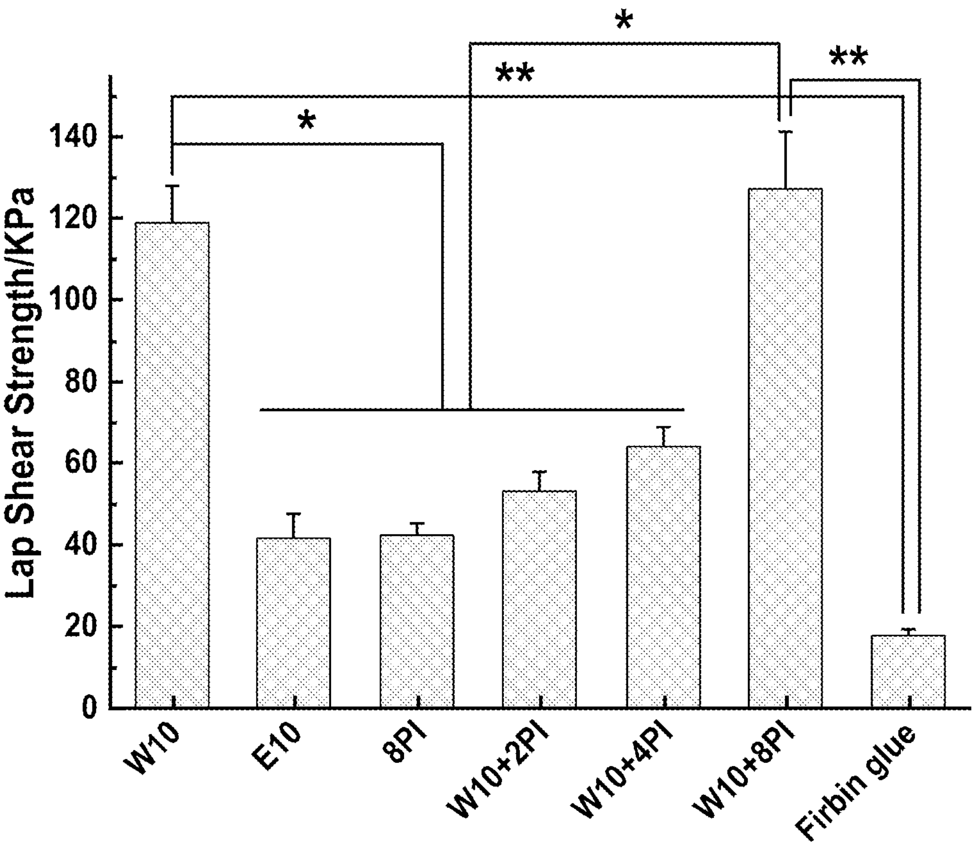
FIG. 6 depicts adhesion strength of iC-EPE crosslinked by MgO, PI (sodium periodate), or MgO+PI and fibrin glue to wet porcine small intestine submucosa measured by lap shear strength testing (*$p<0.05$, **$p<0.01$).

A preliminary assessment of the tissue adhesion strengths of iC-EPE/MgO bioadhesives was carried out by lap shear strength test under wet conditions. The wet lap shear strengths of iC-EPE crosslinked by different crosslinking agents are shown in FIG. 6. The adhesion strengths of all tested formulae were higher than that of commercially available fibrin glue (15.4±2.8 kPa). Although the iC-EPE hydrogels crosslinked by PI (8PI) or MgO/ethanol dispersion (E10) showed the lowest adhesion strengths, and these values were still two-fold that of fibrin glue. The iC-EPE hydrogel crosslinked by MgO and 8 wt % PI (W10+8PI) possessed the highest adhesion strength (127.0±14.0 kPa). Lap shear strength not only reflects the adhesion strength to a substrate but is also closely related to the cohesion strength of the bioadhesive matrix. Thus, the lap shear strength test results further demonstrate that the incorporation of MgO improved the adhesion strengths and cohesion strengths of iC-EPE bioadhesives simultaneously. The adhesion strengths of the iC-EPE/MgO system are superior to that of commercially available fibrin glue and are tunable by varying crosslinking agents.

Example 6

In Vitro Cell Viability and Proliferation

Figure 7:
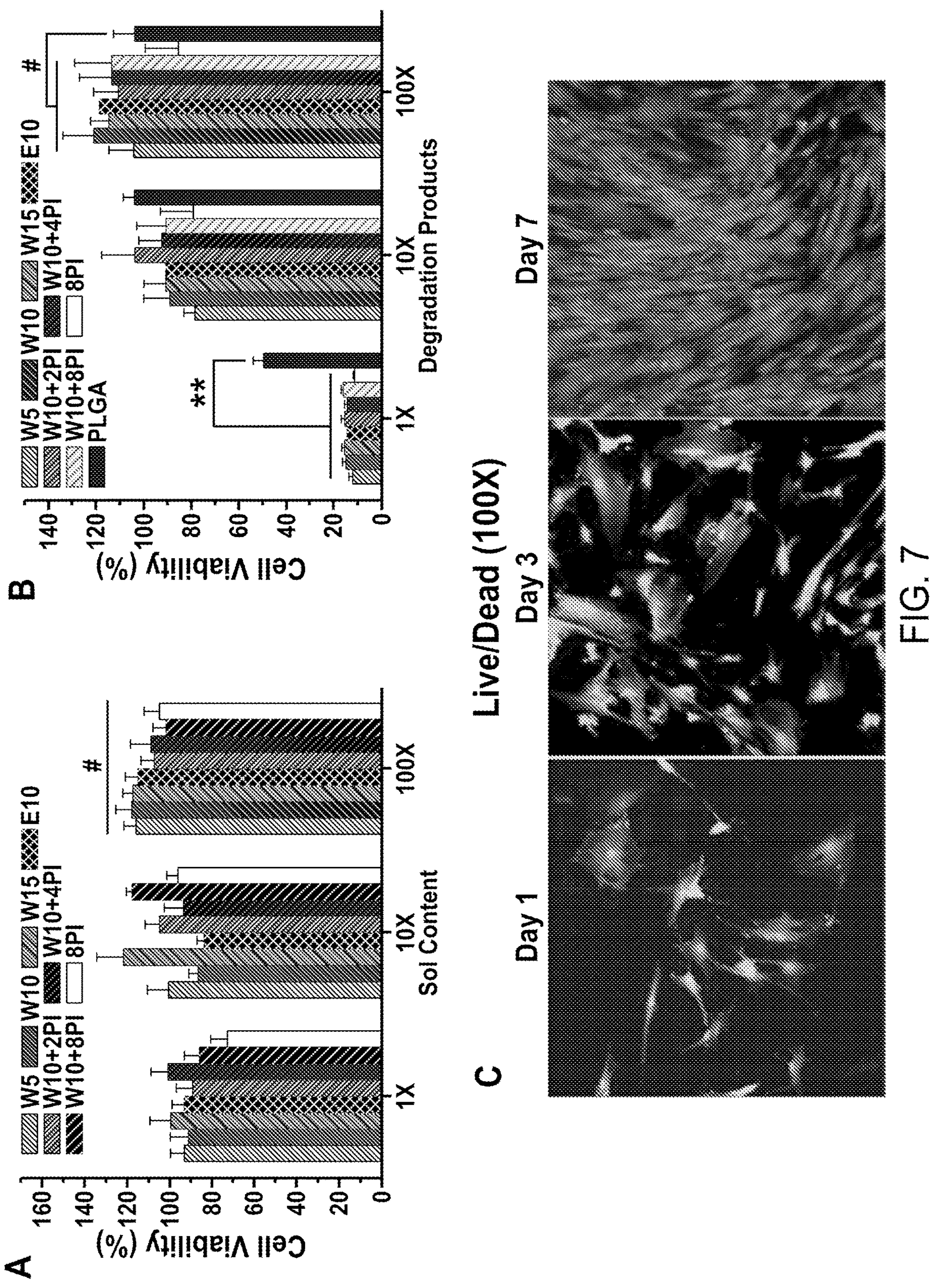
FIGS. 7A-7C depict cytotoxicity evaluation of iC-EPE composite hydrogels: Cytotoxicity against human-derived mesenchymal stem cells (hMSC) by MTT assay for: leachants (sol content) (FIG. 7A) and degradation products (FIG. 7B) of iC-EPE composite hydrogels; Cell proliferation was assessed by Live/Dead assay of hMSCs seeded on MgO (10 wt %) crosslinked iC-EPE cast on glass slides 1, 3, and 7 days post cell seeding (FIG. 7C). #$p>0.05$, **$p<0.01$.

The biocompatibility of iC-EPE hydrogels crosslinked by different crosslinking agents was estimated by conducting cytotoxicity studies of the soluble (leachable) contents and degradation products of various crosslinked iC-EPE hydrogels using MTT assay against human mesenchymal stem cells (hMSCs) (FIGS. 7A-7C). The sol contents of iC-EPE hydrogels at 1× concentration all demonstrated minor cytotoxicity, with hMSC viabilities higher than 80%, except 8PI. The cell viability of all tested samples increased in diluted solutions, with values close to or higher than 100% at 100× diluted sol content (FIG. 7A). The 1× degradation products showed much lower cell viability (<20%) compared to PLGA (~50%). However, the cell viability of the 10× and 100× diluted solutions of degradation products became much higher and was comparable to that of blank media and PLGA (FIG. 7B). The cytotoxicity of crosslinked iC-EPE hydrogels can arise from the release of MgO particles, residual PI, and its reduced components from the hydrogels. The proliferation of hMSCs on crosslinked iC-EPE films was also investigated using W10 as a representative sample by Live/Dead assay over three-time points (1, 3, and 7 days) (FIG. 7D). It could be seen that hMSCs grew well and exhibited stretched/elongated morphology, indicating good cell attachment and proliferation on crosslinked iC-EPE films. These studies clearly indicate that the iC-EPE hydrogels crosslinked by MgO or MgO+PI were cytocompatible to hMSCs.

Example 7

In Vitro Antibacterial Performance

Figure 8:
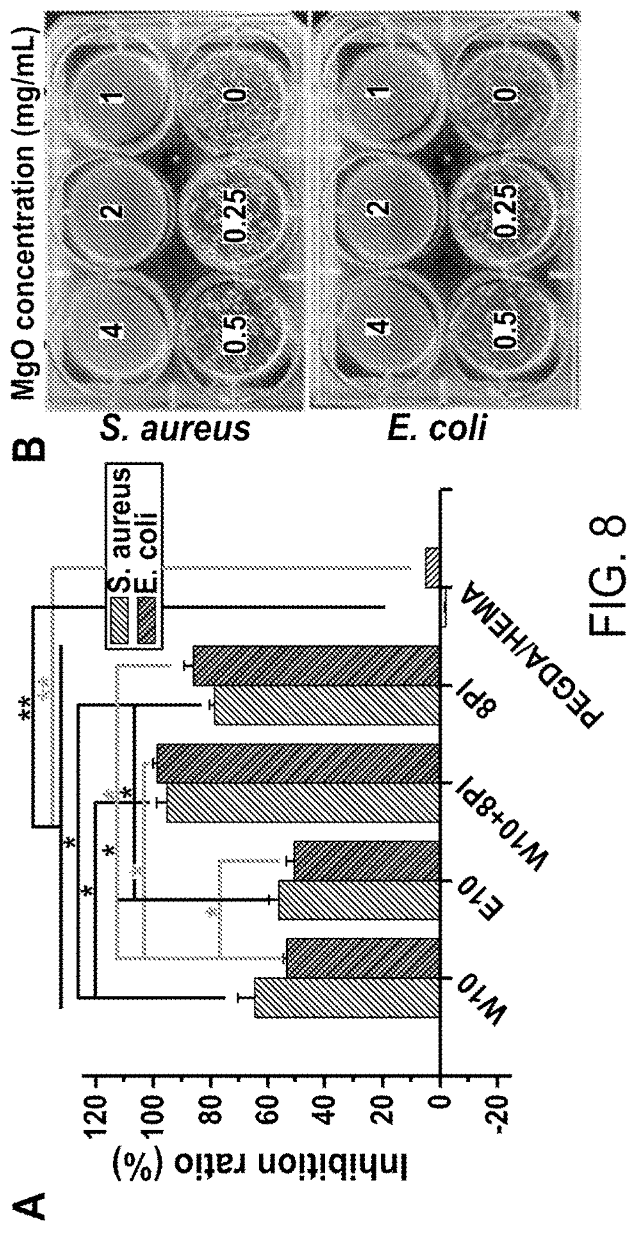
FIGS. 8A-8B depict antibacterial efficacy: Bacterial inhibition ratios of iC-EPE-MgO hydrogels (0.5 g hydrogel in 5 mL bacteria containing broth) against *S. aureus* and *E. coli* (FIG. 8A); and *S. aureus* and *E. coli* growth images on agar gel with different MgO concentrations (the concentrations in mg/mL for MgO dispersed in agar gels in 6-well plates are labeled in black numbers) after 24 hours incubation (FIG. 8B). $*p<0.05$, $**p<0.01$.

The antibacterial performance of the crosslinked iC-EPE hydrogels was assessed using *S. aureus* and *E. coli* as the most medically prevalent Gram-positive and Gram-negative bacteria, respectively, with PEGDA/HEMA as positive control. The bacterial inhibition ratios of crosslinked iC-EPE against *S. aureus* and *E. coli* are shown in FIG. 8A. The iC-EPE hydrogels crosslinked by the combination of MgO and PI (W10+8PI, >95%) exhibited the highest inhibition against both *S. aureus* and *E. coli* among the tested formulae. The hydrogels crosslinked only by PI (8PI, ~80%) displayed decreased inhibition, while the hydrogels crosslinked only by MgO (W10 and E10) exhibited the lowest bacteria inhibitions of around 60%. Without wishing to be bound by any theory, these results could be attributed to 1) PI released much faster than MgO particles because PI is a water-soluble small molecule, while MgO particles (micron-sized) can only disperse in water, and 2) PI itself possesses a much stronger antibacterial effect than MgO particles, which could be seen from our previous work regarding the antibacterial performance of PI and the antibacterial tests of MgO particles described in the following study (FIG. 8B).

In order to further certify the antibacterial property of MgO particles, the antibacterial performance of the MgO particles against *S. aureus* and *E. coli* was evaluated via an agar plate dilution method. FIG. 8B shows representative images for the bactericidal activities of the agar samples with different MgO concentrations. Clearly, higher MgO concentrations led to better antibacterial activity. Negligible bacteria colonies could be observed on the plates with MgO concentrations exceeding 1 mg/mL for *S. aureus* or 2 mg/mL for *E. coli*. Without wishing to be bound by any theory, these results suggested that MgO has considerable antibacterial activity, and the bactericidal efficacy of MgO against *S. aureus* is greater than against *E. coli*.

Based on the experimental data, it was suggested that the antibacterial activity of iC-EPE/MgO bioadhesives can be beneficial in biomedical applications, where microbial infection is a significant challenge to overcome.

Example 8

In Vivo Study

Figure 9:
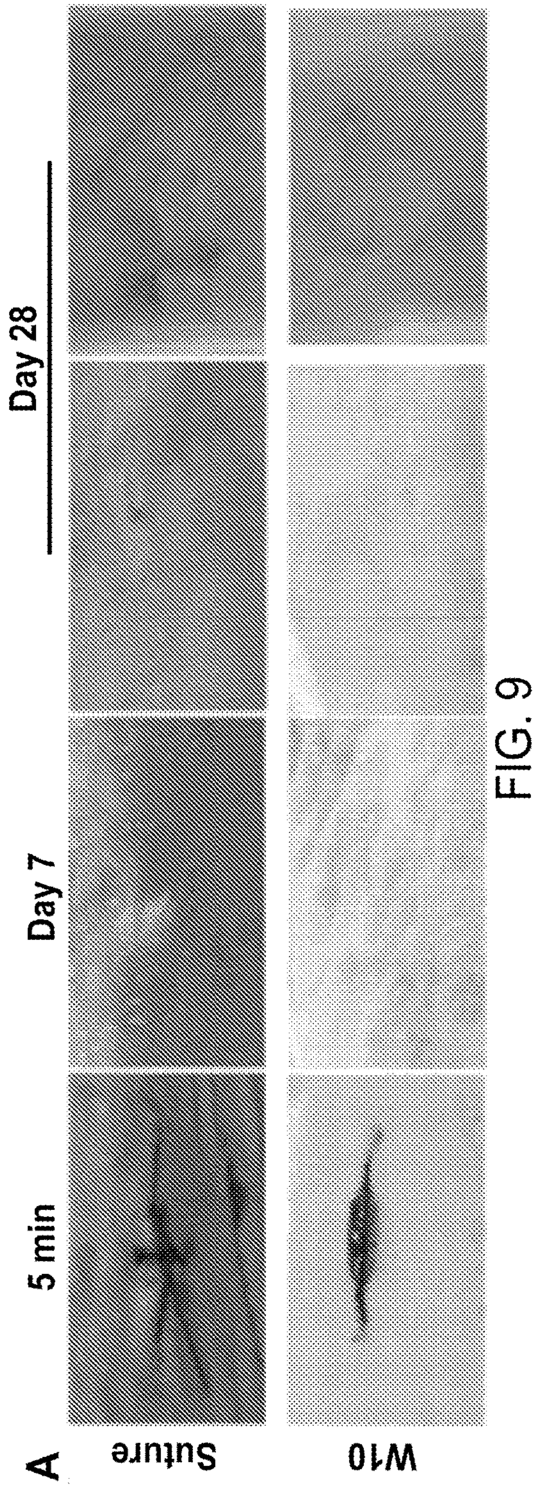
FIGS. 9A-9G depict In vivo evaluation on the biocompatibility and wound closure performance of iC-EPE-MgO (W10).
Figure 9:
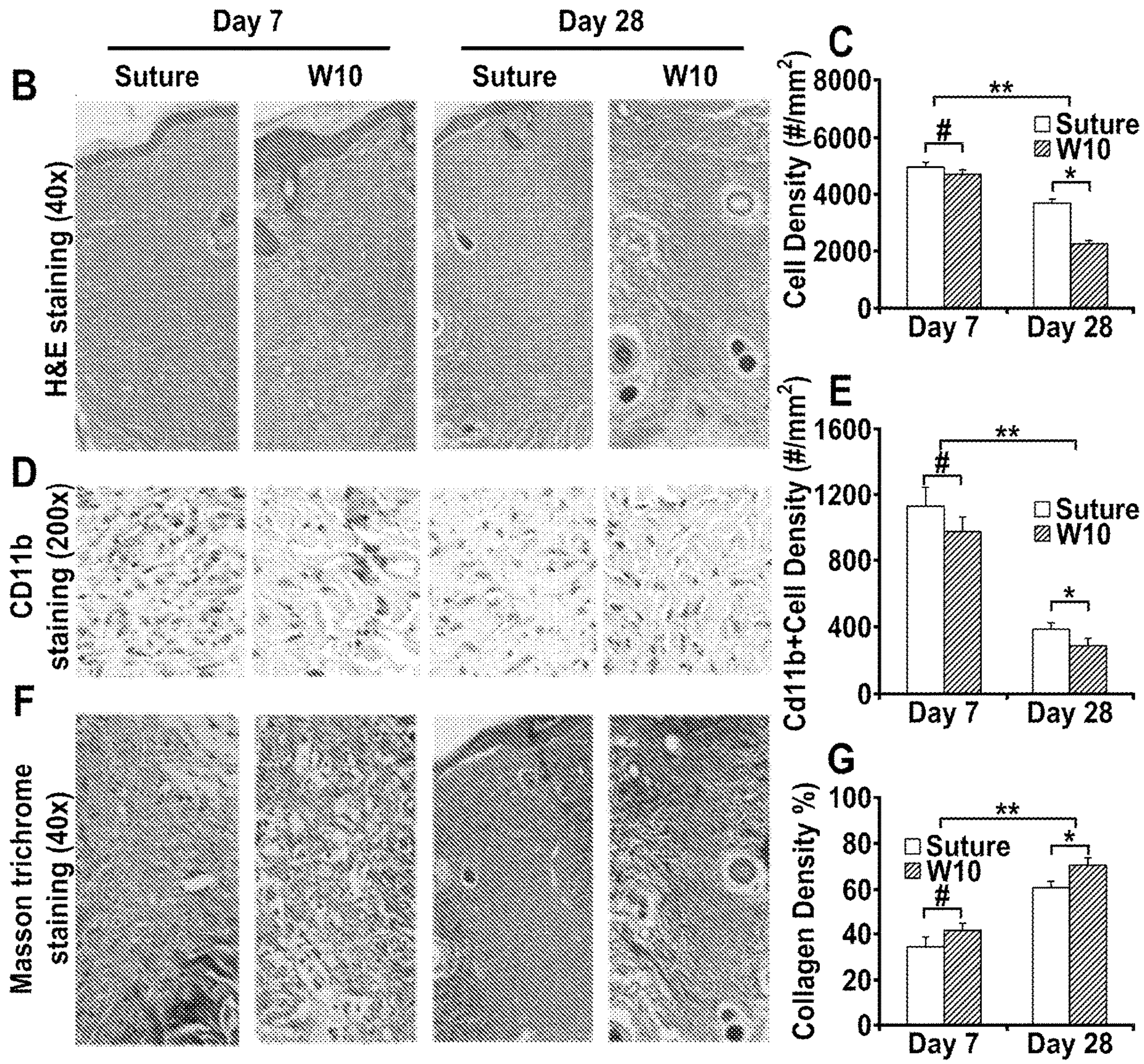

In order to further evaluate the biocompatibility and wound closure efficacy of iC-EPE crosslinked by MgO, an in vivo study was conducted (FIGS. 9A-9G). Upon applying iC-EPE/MgO (W10), the bleeding of incisions on Sprague-Dawley rats was immediately obstructed, and effective wound closure was achieved within 5 minutes (FIG. 9A). The application of W10 in the wounds generated a bulk adhesive chemically crosslinked/adhered to wound tissue via the mussel-inspired strategy [15], providing physical and mechanical barriers against blood loss. Without wishing to be bound by any theory, it was assumed that abundant carboxyl groups on iC-EPE can contribute a hemostatic effect. Previously, $Mg^{2+}$ ions have been reported to play a role in the blood coagulation cascade. Without wishing to be bound by any theory, it was suggested that the inclusion of $Mg^{2+}$ releasing MgO particles could also lead to an accelerated hemostat, another benefit of the iC-EPE/MgO adhesives. Ethanol is the solvent of iC-EPE serves as another hemostatic component, which also aided in bleeding control. Visual observation and comparison between the W10-treated wounds and the sutured wounds at different time points demonstrated high wound healing efficiency of iC-EPE. A diminished scar was observed for the W10-treated wounds compared to the sutured wounds at both day 7 and day 28 (FIG. 9A). Only minor acute inflammation was observed via histological evaluation (H & E staining) on day 7 when W10 was applied (FIG. 9B). Total cell density in the incision area of the W10-treated wounds (4691.7±187.6 #/$mm^2$) showed no significant difference to that of the sutured wound (4975.0±125.0 #/$mm^2$) at day 7 (FIG. 9C), while the total cell density of the wounds treated by W10 (2241.7±142.2 #/$mm^2$) was noticeably less than that of the wounds treated by suturing (3691.7±112.7 #/$mm^2$) at day 28 (FIG. 9C). Similarly, no significant difference between the W10-treated wounds (975.0±90.1 #/$mm^2$) and the sutured wounds (1125.0±114.6 #/$mm^2$) in the densities of CD11 b positive cells in the incision areas on day 7 was detected (FIGS. 9D-9E), while, on day 28, the number of CD11 b positive cells for the W10-treated wounds (291.7±38.2 #/$mm^2$) was significantly less than that of the sutured wound (383.3±38.1 #/$mm^2$, FIG. 9E), indicating the minimal inflammatory response of rats to W10. Furthermore, a higher amount of collagen expression was found at the sites of W10-treated wounds (day 7: 41.7%; day 28: 70.3%) than those treated with sutures (day 7: 34.7%; day 28: 60.3%), especially on day 28 (FIGS. 9F-9G). The above results suggest an excellent in vivo biocompatibility of iC-EPE crosslinked by MgO. The application of iC-EPE/MgO led to improved and accelerated wound healing compared to suturing.

The claims are not intended to include, and should not be interpreted to include, means-plus- or step-plus-function limitations, unless such a limitation is explicitly recited in a given claim using the phrase(s) "means for" or "step for," respectively.

In view of the described processes and compositions, hereinbelow are described certain more particularly described aspects of the inventions. These particularly recited aspects should not, however, be interpreted to have any limiting effect on any different claims containing different or more general teachings described herein, or that the "particular" aspects are somehow limited in some way other than the inherent meanings of the language and formulas literally used therein.

Aspects:

Aspect 1: A composition comprising: a polymer composition that is a polymerization product of one or more monomers of Formula (I), one or more monomers of Formula (II) and/or (II'), one or more monomers of Formula (III), and/or optionally one or more compounds of Formula (IV):

(I)

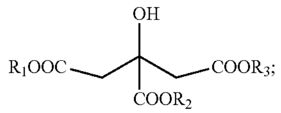

(II)

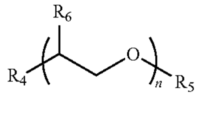

or (II')

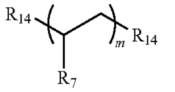

(III)

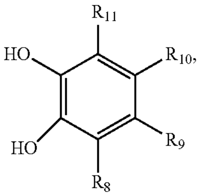

(IV)

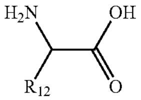

wherein $R_1$, $R_2$, and $R_3$ are, independently, selected from hydrogen, $C_1$-$C_{22}$ alkyl group; wherein each of $R_1$, $R_2$, and $R_3$, can be optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group, $C_2$-$C_{22}$ alkenyl group; $R_5$ is selected from hydrogen, amine, a hydroxyl group, alkoxyl group, or a $C_1$-$C_{22}$ alkyl group; $C_2$-$C_{22}$ alkenyl group; Re is selected from hydrogen, a $C_1$-$C_{22}$ alkyl group, alkenyl group; $R_7$ is selected from hydrogen, amine, a hydroxyl group, alkoxyl group, a $C_1$-$C_{22}$ alkyl group, or a $C_2$-$C_{22}$ alkenyl group; wherein each of $R_4$, $R_5$, $R_6$, and $R_7$, can be optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, $C_1$-$C_{22}$ alkyl group, amine, or a carboxylic acid, wherein each of $R_8$, $R_9$, $R_{10}$, and $R_{11}$, can be optionally substituted with $C_1$-$C_{22}$alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; n and m are, independently, integers from 1 to 2,000; $R_{12}$ is an amino acid side chaining; $R_{14}$ is —OH or —$NH_2$; and wherein the polymer composition is crosslinked to form a polymer network, wherein at least one crosslink in the crosslinked polymer comprises two catechol moieties directly and covalently coupled to each other, and wherein the polymer composition does not comprise metal cations; and b) a compound having a formula $A_bB_a$, wherein A is a metal a monovalent, divalent, or trivalent cation and B is an anion, and wherein a and b are defined by the valency of A and B; wherein the compound behaves as a first crosslinking initiator; and wherein the composition is an adhesive composition.

Aspect 2: The composition of Aspect 1, wherein $R_1$, $R_2$, and $R_3$ are, independently, selected from hydrogen, —$CH_3$ group, or —$CH_2CH_3$ group; $R_4$ is selected from hydrogen, a hydroxyl group, —$NH_2$, —$OCH_3$, —$OCH_2CH_3$, —$CH_3$, —$CH_2CH_3$ group; a $C_3$ to $C_{22}$ alkyl or alkenyl group, —$CH_2CH_2OH$, or —$CH_2CH_2NH_2$; $R_5$ is hydrogen, a hydroxyl group, —$NH_2$, —$OCH_3$, —$OCH_2CH_3$, —$CH_3$, or —$CH_2CH_3$ group, a $C_3$ to $C_{22}$ alkyl or alkenyl group, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$; $R_7$ is selected from hydrogen or —$CH_3$ group; $R_8$, $R_9$, $R_{10}$, and $R_{11}$ are, independently, selected from hydrogen, —$CH_2(CH_2)_xNH_2$, —$CH_2(CHR_{13})NH_2$, or —$CH_2(CH_2)_xCOOH$ groups; $R_{13}$ is —COOH or —$(CH_2)_yCOOH$ group; n and m are, independently, integers from 1 to 2,000; x is an integer from 0 to 20; and y is an integer from 1 to 20.

Aspect 3: The composition of Aspect 1 or 2, wherein the monomer of Formula (III) comprises dopamine of L-DOPA.

Aspect 4: The composition of Aspect 1 or 2, wherein the first crosslinking initiator behaves as a filler.

Aspect 5: The composition of any one of Aspects 1-3, wherein the first crosslinking initiator comprises a metal oxide.

Aspect 6: The composition of Aspect 5, wherein the metal oxide is magnesium oxide, calcium oxide, zinc oxide, copper oxide, barium oxide, iron oxide, or any combination thereof.

Aspect 7: The composition of any one of Aspects 1-6, wherein the polymer composition comprises the one or more monomers of Formula (II) and (II').

Aspect 8: The composition of Aspect 6, wherein the polymerization product comprises a block polymer of one or more monomers of Formula (II) and (II') polymerized with the one or more monomers of Formula (I) and (III).

Aspect 9: The composition of any one of Aspects 1-8, wherein the compound of Formula (IV) is present in the polymerization product.

Aspect 10: The composition of any one of Aspects 1-9, wherein the composition is a hydrogel.

Aspect 11: The composition of any one of Aspects 1-10, wherein the first crosslinking initiator is present in an amount from greater than 0 wt % to less than 100 wt % based on a weight percent of a dry polymerization product.

Aspect 12: The composition of any one of Aspects 1-11, wherein the composition further comprises a second crosslinking initiator comprising sodium periodate.

Aspect 13: The composition of any one of Aspect 1-12, wherein the composition further comprises a solvent.

Aspect 14: The composition of Aspect 13, wherein the solvent is water, ethanol, or a combination thereof.

Aspect 15: The composition of any one of Aspects 1-14, wherein the composition comprises a sol content less than about 25%.

Aspect 16: The composition of any one of Aspects 1-15, wherein the composition exhibits a swelling ratio of less than about 200%.

Aspect 17: The composition of any one of Aspects 1-16, wherein the composition exhibits a tensile strength from about 1 to about 10 MPa in a dry state as measured according to ASTM D412A.

Aspect 18: The composition of any one of Aspects 1-17, wherein the composition exhibits an elongation at break from about 15% to about 150% a dry state as measured according to ASTM D412A.

Aspect 19: The composition of any one of Aspects 1-18, wherein the composition exhibits a modulus from about 1 to about 10 MPa in a dry state as measured according to ASTM D412A.

Aspect 20: The composition of any one of Aspects 1-19, wherein the composition exhibits a lap shear strength of greater than 30 kPa as measured according to a modified ASTM D1002-05 method.

Aspect 21: The composition of any one of Aspects 5-20, wherein the composition exhibits a higher cytocompatibility as measured against human mesenchymal stem cells when compared to a substantially identical reference composition with an absence of the metal oxide.

Aspect 22: The composition of any one of Aspects 12-21, wherein the composition exhibits an increased inhibition against *S. aureus* and *E. coli* when compared to a substantially identical reference composition in the absence of the metal oxide.

Aspect 23: The composition of any one of Aspects 1-22, further comprising at least one pharmaceutically active component.

Aspect 24: The composition of any one of Aspects 1-23, wherein the composition is a wound closing composition.

Aspect 25: A method of making a composition, comprising: a) mixing a polycarboxylic acid of one or more monomers of Formula (I)

(I)

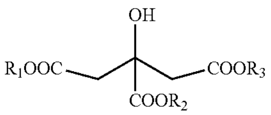

with a compound comprising one or more monomers of Formula (II) and/or (II')

(II)

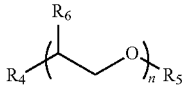

or (II')

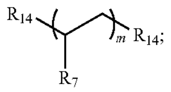

and/or with a compound of one or more monomers of Formula (III)

(III)

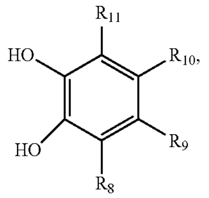

and/or optionally with one or more compounds of Formula (IV)

(IV)

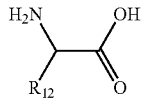

at conditions effective to form a polymer composition configured to be crosslinked; wherein $R_1$, $R_2$, and $R_3$ are, independently, selected from hydrogen, $C_1$-$C_{22}$ alkyl group; wherein each of $R_1$, $R_2$, and $R_3$, can be optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group, $C_2$-$C_{22}$ alkenyl group; $R_5$ is selected from hydrogen, amine, a hydroxyl group, alkoxyl group, or a $C_1$-$C_{22}$ alkyl group, $C_2$-$C_{22}$ alkenyl group; $R_6$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group, or a $C_2$-$C_{22}$ alkenyl group; wherein each of $R_4$, $R_5$, $R_6$, and $R_7$, can be optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, $C_1$-$C_{22}$ alkyl group, amine, or a carboxylic acid, wherein each of $R_8$, $R_9$, $R_{10}$, and $R_{11}$, can be optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; n and m, are independently, integers from 1 to 2,000; $R_{12}$ is an amino acid side chain; $R_{14}$ is —OH or —$NH_2$; and wherein the formed polymer composition does not comprise metal cations; b)

adding a first crosslinking initiator to the formed polymer composition; and c) crosslinking the formed polymer composition to form a composition comprising a crosslinked polymer composition forming a polymer network, wherein at least one crosslink in the crosslinked polymer comprises two catechol moieties directly and covalently coupled to each other; and wherein the composition is an adhesive composition.

Aspect 26: The method of Aspect 25, wherein $R_1$, $R_2$, and $R_3$ are, independently, selected from hydrogen, $-CH_3$ group, or $-CH_2CH_3$ group; $R_4$ is selected from hydrogen, a hydroxyl group, $-NH_2$, $-OCH_3$, $-OCH_2CH_3$, $-CH_3$, $-CH_2CH_3$ group; a $C_3$ to $C_{22}$ alkyl or alkenyl group, $-CH_2CH_2OH$, or $-CH_2CH_2NH_2$; $R_5$ is hydrogen, a hydroxyl group, $-NH_2$, $-OCH_3$, $-OCH_2CH_3$, $-CH_3$, or $-CH_2CH_3$ group, a $C_3$ to $C_{22}$ alkyl or alkenyl group, $-CH_2CH_2OH$, or $-CH_2CH_2NH_2$; $R_6$ is selected from hydrogen, $-CH_3$ group, or $-CH_2CH_3$ group; $-CH_2CH_2OH$, or $-CH_2CH_2NH_2$; $R_7$ is selected from hydrogen or $-CH_3$ group; $R_8$, $R_9$, $R_{10}$, and $R_{11}$ are, independently, selected from hydrogen, $-CH_2(CH_2)_xNH_2$, $-CH_2(CHR_{13})NH_2$, or $-CH_2(CH_2)_xCOOH$ groups; $R_{13}$ is $-COOH$ or $-(CH_2)_yCOOH$ group; n and m are, independently, integers from 1 to 2,000; x is an integer from 0 to 20; and y is an integer from 1 to 20.

Aspect 27: The method of Aspect 25 or 26, wherein the monomer of formula (III) comprises dopamine of L-DOPA.

Aspect 28: The method of any one of Aspects 25-27, wherein the first crosslinking initiator behaves as a filler.

Aspect 29: The method of any one of Aspects 25-28, wherein the first crosslinking initiator comprises a metal oxide.

Aspect 30: The method of Aspect 29, wherein the metal oxide is magnesium oxide, calcium oxide, zinc oxide, copper oxide, barium oxide, iron oxide, or any combination thereof.

Aspect 31: The method of any one of Aspects 25-30, wherein the polymer composition comprises the one or more monomers of Formula (II) and (II').

Aspect 32: The method of Aspect 33, wherein the one or more monomers of Formula (II) and (II') form a block polymer comprising repeating units of Formula (II) and (II') before mixing with the polycarboxylic acid.

Aspect 33: The method of any one of Aspects 25-32, wherein the compound of Formula (IV) is present.

Aspect 34: The method of any one of Aspects 25-33, wherein the composition is a hydrogel.

Aspect 35: The method of any one of Aspects 25-34, wherein the first crosslinking initiator is added in an amount from greater than 0 wt % to less than 100 wt % based on a weight percent of a dry polymerization product.

Aspect 36: The method of any one of Aspects 25-35, wherein the first crosslinking initiator is a solvent dispersion of the first crosslinking initiator.

Aspect 37: The method of Aspect 36, wherein the solvent dispersion comprises water, ethanol, or a combination thereof.

Aspect 38: The method of any one of Aspects 25-37, further comprising a second crosslinking initiator comprising sodium periodate.

Aspect 39: The method of Aspect 38, wherein the second crosslinking is added in the solvent dispersion of the first crosslinking initiator.

Aspect 40: The method of Aspect 39, wherein the second crosslinking initiator is added as a separate solvent dispersion of the second crosslinking initiator.

Aspect 41: The method of Aspect 40, the separate solvent dispersion comprises water, ethanol, or a combination thereof.

Aspect 42: The method of Aspect 34, wherein a gel time needed to form the hydrogel is from about 500 s to less than about 10 s.

Aspect 43: The method of Aspect 42, wherein the first and the second crosslinking initiators have a synergistic effect.

Aspect 44: The method of any one of Aspects 30-43, wherein a crosslinking rate is substantially higher when compared to a substantially identical reference method in the absence of the metal oxide.

Aspect 45: The method of any one of Aspects 30-44, wherein the step of crosslinking comprises: metal oxide initiated crosslinking via coupling of catechol groups of the polymer composition, formation of a metal complex with the catechol groups of the polymer composition, bonding metal oxide via hydrogen bonds or surface bonds with carboxyl groups or catechol groups of the polymer composition, or any combination thereof.

Aspect 46: The method of any one of Aspects 25-45, wherein the formed composition comprises a sol content less than about 25%.

Aspect 47: The method of any one of Aspects 25-46, wherein the formed composition exhibits a swelling ratio of less than about 200%.

Aspect 48: The method of any one of Aspects 25-47, wherein the formed composition exhibits a tensile strength from about 1 to about 10 MPa in a dry state as measured according to ASTM D412A.

Aspect 49: The method of any one of Aspects 25-48, wherein the formed composition exhibits an elongation at break from about 15% to about 150% a dry state as measured according to ASTM D412A.

Aspect 50: The method of any one of Aspects 25-49, wherein the formed composition exhibits a modulus from about 1 to about 10 MPa in a dry state as measured according to ASTM D412A.

Aspect 51: The method of any one of Aspects 25-50, wherein the formed composition exhibits a lap shear strength of greater than 30 kPa as measured according to a modified ASTM D1002-05 method.

Aspect 52: The method of any one of Aspects 30-51, wherein the formed composition exhibits a higher cytocompatibility as measured against human mesenchymal stem cells when compared to a substantially identical reference composition with an absence of the metal oxide.

Aspect 53: The method of any one of Aspects 30-52, wherein the formed composition exhibits an increased inhibition against *S. aureus* and *E. coli* when compared to a substantially identical reference composition in the absence of the metal oxide.

Aspect 54: The method of any one of Aspects 25-53, further comprising adding at least one pharmaceutically active component to the formed composition.

Aspect 55: The method of any one of Aspects 25-54, wherein the formed composition is a wound closing composition.

Aspect 56: A method of adhering a biological tissue, comprising: a) disposing the composition of any one of Aspects 1-24 between a first portion of biological tissue and a second portion of biological tissue; and b) contacting the first portion of biological tissue with the second portion of biological tissue.

Aspect 57: A method of treating disease, comprising disposing the composition of Aspect 23 within the biological body, wherein the at least one pharmaceutically active component is active towards the disease and is configured to be released into the biological body at a predetermined time.

Aspect 58: A method of promoting a biological tissue growth comprising providing a scaffold comprising the composition of any one of Aspects 1-24 and disposing the scaffold in a tissue growth media.

Aspect 59: A crosslinked composition comprising: a) a polymerization product of one or more monomers of Formula (I) and one or more units of a block copolymer comprising one or more monomers of Formula (II), and/or Formula (II'), one or more monomers of Formula (III), and/or optionally one or more compounds of Formula (IV):

(I)

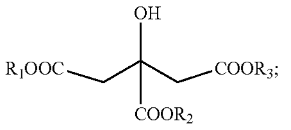

(II)

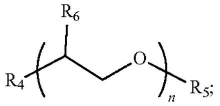

(II')

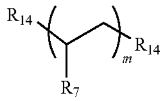

(III)

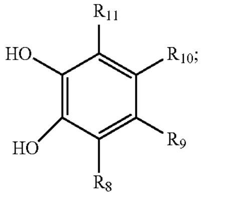

(IV)

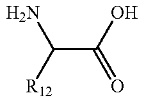

wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; $R_6$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m, are independently integers from 1 to 20; $R_{12}$ is an amino acid side chain; $R_{14}$ is —OH or —$NH_2$; and wherein the polymerization product does not comprise metal cations; and b) a first crosslinking initiator having a formula $A_bO_{a'}$, wherein A is a monovalent, divalent, or trivalent metallic cation and wherein a' and b" are dependent on the valency of A; wherein A is not a transition metal cation and wherein the first crosslinking initiator is configured to crosslink the reaction product to form the crosslinked composition; and wherein the crosslinked composition is a polymer network having at least one crosslink comprising two catechol moieties directly and covalently coupled to each other; wherein the crosslinked composition is a hydrogel or an organogel and is an adhesive composition.

Aspect 60: The crosslinked composition of Aspect 59, wherein $R_1$, $R_2$, and $R_3$ are, independently, selected from hydrogen, —$CH_3$ group, or —$CH_2CH_3$ group; $R_4$ is selected from hydrogen, a hydroxyl group, —$NH_2$, —$OCH_3$, —$OCH_2CH_3$, —$CH_3$, —$CH_2CH_3$ group; a $C_3$ to $C_{22}$ alkyl or alkenyl group, —$CH_2CH_2OH$, or —$CH_2CH_2NH_2$; $R_5$ is hydrogen, a hydroxyl group, —$NH_2$, —$CH_3$, or —$CH_2CH_3$ group, a $C_3$ to $C_{22}$ alkyl or alkenyl group, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$; $R_7$ is selected from hydrogen or —$CH_3$ group; $R_8$, $R_9$, $R_{10}$, and $R_{11}$ are, independently, selected from hydrogen, —$CH_2(CH_2)_xNH_2$, —$CH_2(CHR_{13})NH_2$, or —$CH_2(CH_2)_xCOOH$ groups; and wherein at least one of $R_8$, $R_9$, $R_{10}$, and $R_{11}$ is not hydrogen; $R_{13}$ is —COOH or —$(CH_2)_yCOOH$ group; n and m, are independently integers from 1 to 20; x is an integer from 0 to 20; and y is an integer from 1 to 20.

Aspect 61: The crosslinked composition of Aspect 59 or 60, wherein the nucleophilic group of the one or more monomers of formula (III) is configured to react with at least one of $R_1COO$—, $R_2COO$—, or $R_3COO$— of the one or more monomer of formula (I) to form a covalent bond.

Aspect 62: The crosslinked composition of any one of Aspects 59-61, wherein the block copolymer comprises repeating units of two or more monomers of Formula (II);

(II)

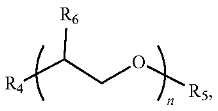

wherein $R_4$ is selected from hydrogen, a hydroxyl group, —$NH_2$, —$CH_2CH_2OH$, or —$CH_2CH_2NH_2$; $R_5$ is hydrogen, a hydroxyl group, —$NH_2$, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$.

Aspect 63: The crosslinked composition of Aspect 62, wherein the block copolymer has a formula (V) or formula (V'):

(V)

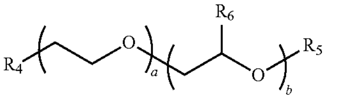

(V')

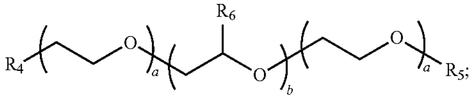

wherein a and b are independently chosen from n=1-20, and wherein $R_6$ is not hydrogen.

Aspect 64: The crosslinked composition of any one of Aspects 59-63, wherein the monomer of Formula (III) comprises dopamine of L-DOPA.

Aspect 65: The crosslinked composition of any one of Aspects 59-64, wherein the polymerization product comprises:

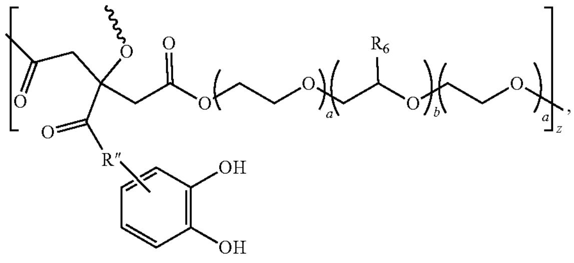

wherein R" is —N(H)$R_{15}$, or —O(CO)($R_{15}$), or —O($R_{15}$); wherein $R_{15}$ is independently selected from $C_1$-$C_{22}$ alkyl group, optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl groups; wherein $R_6$ is not hydrogen; wherein  defines a bond to hydrogen, or optionally to a predetermined polymer chain if present; wherein a and b are independently chosen from n=1-20, and wherein z=1-100.

Aspect 66: The crosslinked composition of any one of Aspects 59-65, wherein the first crosslinking initiator simultaneously behaves as a first filler.

Aspect 67: The crosslinked composition of any one of Aspects 59-66, further comprising a second crosslinking initiator that is different from the first crosslinking initiator.

Aspect 68: The crosslinked composition of Aspect 67, wherein the second crosslinking initiator comprises sodium periodate, silver nitrate, or ferric chloride, or any combination thereof.

Aspect 69: The crosslinked composition of any one of Aspects 66-68, further comprising an additional filler that is different from the first filler.

Aspect 70: The crosslinked composition of any one of Aspects 59-69, wherein the metal oxide is magnesium oxide, calcium oxide, zinc oxide, barium oxide, cesium oxide, or any combination thereof.

Aspect 71: The crosslinked composition of any one of Aspects 59-70, wherein the compound of Formula (IV) is present in the polymerization product.

Aspect 72: The crosslinked composition of any one of Aspects 59-71, wherein the first crosslinking initiator is present in an amount from greater than 0 wt % to less than 100 wt % based on a weight percent of a dry polymerization product.

Aspect 73: The crosslinked composition of any one of Aspects 69-72, wherein the second crosslinking initiator is present in an amount from greater than 0 wt % to about 8 wt % based on a weight percent of a dry polymerization product.

Aspect 74: The crosslinked composition of any one of Aspects 59-73, wherein the crosslinked composition further comprises a solvent.

Aspect 75: The crosslinked composition of Aspect 74, wherein the solvent is water, ethanol, or a combination thereof.

Aspect 76: The crosslinked composition of any one of Aspects 59-75, wherein the crosslinked composition comprises a sol content less than about 25%.

Aspect 77: The crosslinked composition of any one of Aspects 59-76, wherein the crosslinked composition exhibits a swelling ratio of less than about 200

Aspect 78: The crosslinked composition of any one of Aspects 59-77, wherein the crosslinked composition exhibits a tensile strength from about 1 to about MPa in a dry state as measured according to ASTM D412A.

Aspect 79: The crosslinked composition of any one of Aspects 59-78, wherein the crosslinked composition exhibits an elongation at break from about 15% to about 150% a dry state as measured according to ASTM D412A.

Aspect 80: The composition of any one of Aspects 59-79, wherein the crosslinked composition exhibits a modulus from about 1 to about 10 MPa in a dry state as measured according to ASTM D412A.

Aspect 81: The composition of any one of Aspects 59-80, wherein the crosslinked composition exhibits a lap shear strength of greater than 30 kPa as measured according to a modified ASTM D1002-05 method.

Aspect 82: The composition of any one of Aspects 59-81, wherein the crosslinked composition exhibits a higher cytocompatibility as measured against human mesenchymal stem cells when compared to a substantially identical reference composition with an absence of the metal oxide.

Aspect 83: The composition of any one of Aspects 69-82, wherein the crosslinked composition exhibits an increased inhibition against *S. aureus* and *E. coli* when compared to a substantially identical reference composition in the absence of the metal oxide.

Aspect 84: The composition of any one of Aspects 59-83, further comprising at least one pharmaceutically active component.

Aspect 85: The composition of any one of Aspects 59-84, wherein the composition is a wound closing composition.

Aspect 86: A crosslinked composition formed by a) forming a polymerization product by reacting a polycarboxylic acid of one or more monomers of Formula (I) with a block copolymer comprising one or more monomers of Formula (II), and/or Formula (II'), one or more monomers of Formula (III), and/or optionally one or more compounds of Formula (IV):

(I)

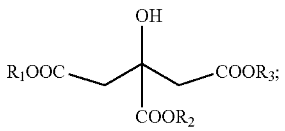

-continued (II)

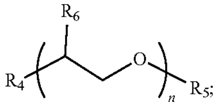

(II')

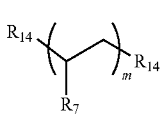

(III)

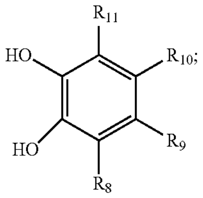

(IV)

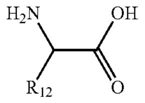

Wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; $R_6$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m, are independently integers from 1 to 20; $R_{12}$ is an amino acid side chain; $R_{14}$ is —OH or —$NH_2$; and wherein the polymerization product does not comprise metal cations; b) crosslinking the polymerization product with a first crosslinking initiator having a formula $A_bO_{a'}$, wherein A is a monovalent, divalent, or trivalent metallic cation and wherein a' and b" are defined by the valency of A; wherein A is not a transition metal cation; wherein the crosslinked composition is a polymer network having at least one crosslink comprising two catechol moieties directly and covalently coupled to each other; wherein the crosslinked composition is a hydrogel or organogel and is an adhesive composition.

Aspect 87: The crosslinked composition of Aspect 86, wherein $R_1$, $R_2$, and $R_3$ are, independently, selected from hydrogen, —$CH_3$ group, or —$CH_2CH_3$ group; $R_4$ is selected from hydrogen, a hydroxyl group, —$NH_2$, —$OCH_3$, —$OCH_2CH_3$, —$CH_3$, —$CH_2CH_3$ group; a $C_3$ to $C_{22}$ alkyl or alkenyl group, —$CH_2CH_2OH$, or —$CH_2CH_2NH_2$; $R_5$ is hydrogen, a hydroxyl group, —$NH_2$, —$CH_3$, or —$CH_2CH_3$ group, a $C_3$ to $C_{22}$ alkyl or alkenyl group, —$CH_2CH_2OH$, or —$CH_2CH_2NH_2$; $R_5$ is selected from hydrogen, —$CH_3$ group, or —$CH_2CH_3$ group; —$CH_2CH_2OH$, or —$CH_2CH_2NH_2$; $R_7$ is selected from hydrogen or —$CH_3$ group; $R_8$, $R_9$, $R_{10}$, and $R_{11}$ are, independently, selected from hydrogen, —$CH_2(CH_2)_xNH_2$, —$CH_2(CHR_{13})NH_2$, or —$CH_2(CH_2)_xCOOH$ groups; and wherein at least one of $R_8$, $R_9$, $R_{10}$, and $R_{11}$ is not hydrogen; $R_{13}$ is —COOH or —$(CH_2)_yCOOH$ group; n and m, are independently integers from 1 to 20; x is an integer from 0 to 20; and y is an integer from 1 to 20.

Aspect 88: The crosslinked composition of Aspects 86 or 8729, wherein the nucleophilic group of the one or more monomers of formula (III) reacts with at least one of $R_1COO$—, $R_2COO$—, or $R_3COO$— of the one or more monomer of formula (I) to form a covalent bond.

Aspect 89: The crosslinked composition of any one of Aspects 86-88, wherein the block copolymer comprises repeating units of two or more monomers of Formula (II);

(II)

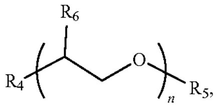

wherein $R_4$ is selected from hydrogen, a hydroxyl group, —$NH_2$, —$CH_2CH_2OH$, or —$CH_2CH_2NH_2$; $R_5$ is hydrogen, a hydroxyl group, —$NH_2$, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$.

Aspect 90: The crosslinked composition of Aspect 89, wherein the block copolymer has a formula (V) or formula (V'):

(V)

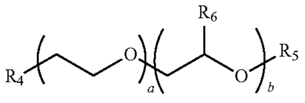

(V')

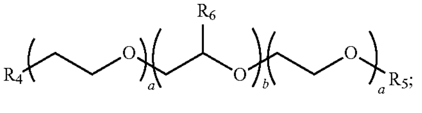

wherein a and b are independently chosen from n=1-20, and wherein $R_6$ is not hydrogen.

Aspect 91: The crosslinked composition of any one of Aspects 86-90, wherein the monomer of Formula (III) comprises dopamine of L-DOPA.

Aspect 92: The crosslinked composition of any one of Aspects 86-91, wherein the polymerization product comprises:

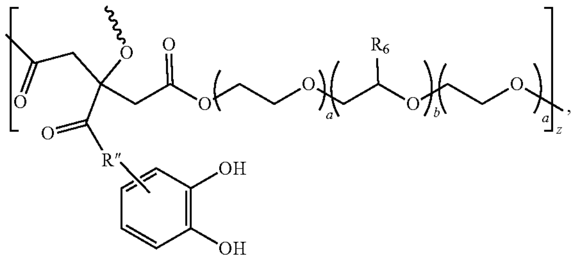

wherein R" is —N(H)$R_{15}$, or —O(CO)($R_{15}$), or —O($R_{15}$); wherein $R_{15}$ is independently selected from $C_1$-$C_{22}$ alkyl group, optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl groups; wherein $R_6$ is not hydrogen; wherein 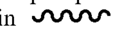 defines a bond to hydrogen, or optionally to a predetermined polymer chain if present; wherein a and b are independently chosen from n=1-20, and wherein z=1-100.

Aspect 93: A method of making a composition, comprising: a) reacting a polycarboxylic acid of one or more monomers of Formula (I)

(I)

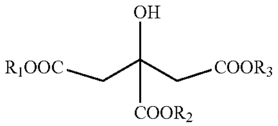

with one or more units of a block copolymer comprising one or more monomers of Formula (II) and (II'), (II)

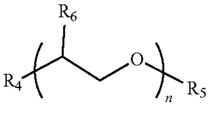 or (II')

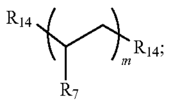

and with a compound of one or more monomers of Formula (III)

(III)

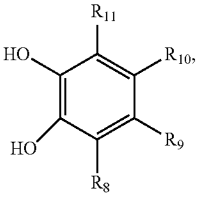

and optionally with one or more compounds of Formula (IV)

(IV)

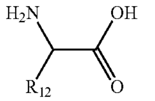

at conditions effective to form a prepolymer composition configured to be crosslinked; wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; $R_6$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m, are independently integers from 1 to 20; $R_{12}$ is an amino acid side chain; $R_{14}$ is —OH or —$NH_2$; and wherein the polymerization product does not comprise metal cations; b) adding a first crosslinking initiator to the prepolymer composition; wherein the first crosslinking initiator has a formula $A_bB_a$, wherein A is a monovalent, divalent, or trivalent metallic cation and B is an anion, and wherein a and b are defined by the valency of A and B; wherein A is not a transition metal cation and c) crosslinking the prepolymer composition to form a crosslinked composition comprising a polymer network, wherein at least one crosslink in the crosslinked polymer comprises two catechol moieties directly and covalently coupled to each other; and wherein the crosslinked composition is a hydrogel or organogel and is adhesive.

Aspect 94: The method of Aspect 93, wherein $R_1$, $R_2$, and $R_3$ are, independently, selected from hydrogen, —$CH_3$ group, or —$CH_2CH_3$ group; $R_4$ is selected from hydrogen, a hydroxyl group, —$NH_2$, —$OCH_3$, —$OCH_2CH_3$, —$CH_3$, —$CH_2CH_3$ group; a $C_3$ to $C_{22}$ alkyl or alkenyl group, —$CH_2CH_2OH$, or —$CH_2CH_2NH_2$; $R_5$ is hydrogen, a hydroxyl group, —$NH_2$, —$CH_3$, or —$CH_2CH_3$ group, a $C_3$ to $C_{22}$ alkyl or alkenyl group, —$CH_2CH_2OH$, or —$CH_2CH_2NH_2$; $R_5$ is selected from hydrogen, —$CH_3$ group, or —$CH_2CH_3$ group; —$CH_2CH_2OH$, or —$CH_2CH_2NH_2$; $R_7$ is selected from hydrogen or —$CH_3$ group; $R_8$, $R_9$, $R_{10}$, and $R_{11}$ are, independently, selected from hydrogen, —$CH_2(CH_2)_xNH_2$, —$CH_2(CHR_{13})NH_2$, or —$CH_2(CH_2)_xCOOH$ groups; and wherein at least one of $R_8$, $R_9$, $R_{10}$, and $R_{11}$ is not hydrogen; $R_{13}$ is —COOH or —$(CH_2)_yCOOH$ group; n and m, are independently integers from 1 to 20; x is an integer from 0 to 20; and y is an integer from 1 to 20.

Aspect 95: The method of Aspect 93 or 94, where the block copolymer is formed prior to reacting in step a).

Aspect 96: The method of any one of Aspects 93-95, wherein the block copolymer is formed prior to reacting in step a) and comprises repeating units of two or more monomers of Formula (II);

(II)

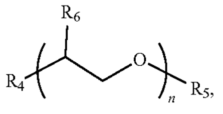

wherein $R_4$ is selected from hydrogen, a hydroxyl group, —$NH_2$, —$CH_2CH_2OH$, or —$CH_2CH_2NH_2$; $R_5$ is hydrogen, a hydroxyl group, —$NH_2$, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$.

Aspect 97: The method of Aspect 96, wherein the block copolymer has a formula (V) or formula (V'):

(V)

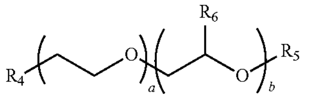

(V')

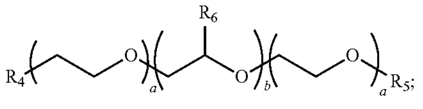

wherein a and b are independently chosen from n=1-20, and wherein $R_6$ is not hydrogen.

Aspect 98: The method of any one of Aspects 93-97, wherein the monomer of formula (III) comprises dopamine of L-DOPA.

Aspect 99: The method of any one of Aspects 93-98, wherein the polymerization product comprises:

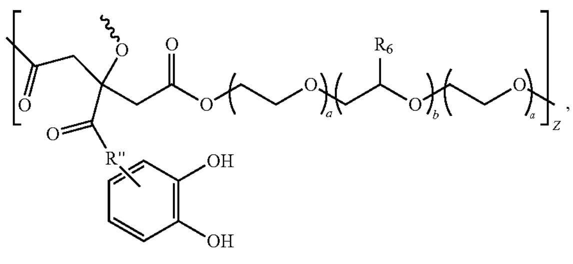

wherein R" is —$N(H)R_{15}$, or —$O(CO)(R_{15})$, or —$O(R_{15})$; wherein $R_{15}$ is independently selected from $C_1$-$C_{22}$ alkyl group, optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl groups; wherein $R_6$ is not hydrogen; wherein 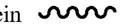 defines a bond to hydrogen, or optionally to a predetermined polymer chain if present; wherein a and b are independently chosen from n=1-20, and wherein z=1-100.

Aspect 100: The method of any one of Aspects 93-99, wherein the first crosslinking initiator simultaneously behaves as a first filler.

Aspect 101: The method of any one of Aspects 93-100, further comprising adding a second crosslinking initiator that is different from the first crosslinking initiator.

Aspect 102: The method of Aspect 101, wherein the second crosslinking initiator comprises sodium periodate, silver nitrate, or ferric chloride, or any combination thereof.

Aspect 103: The method of any one of Aspects 100-102, further comprising an additional filler that is different from the first filler.

Aspect 104: The method of any one of Aspects 100-103, wherein the metal oxide is magnesium oxide, calcium oxide, zinc oxide, barium oxide, cesium oxide, or any combination thereof.

Aspect 105: The method of any one of Aspects 100-104, wherein the compound of Formula (IV) is present.

Aspect 106: The method of any one of Aspects 100-105, wherein the first crosslinking initiator is added in an amount from greater than 0 wt % to less than 100 wt % based on a weight percent of a dry polymerization product.

Aspect 107: The method of any one of Aspects 100-106, wherein the first crosslinking initiator is a solvent dispersion of the first crosslinking initiator.

Aspect 108: The method of Aspect 107, wherein the solvent dispersion comprises water, ethanol, or a combination thereof.

Aspect 109: The method of any one of Aspects 100-108, wherein the second crosslinking initiator is added in an amount from greater than 0 wt % to about 8 wt % based on a weight percent of a dry polymerization product.

Aspect 110: The method any one of Aspects 101-109, wherein the second crosslinking initiator is added together with the first crosslinking initiator, or prior to adding of the first crosslinking initiator; or after adding the first crosslinking initiator.

Aspect 111: The method of any one of Aspects 107-110, wherein the second crosslinking is added in a solvent dispersion of the first crosslinking initiator.

Aspect 112: The method of any one of Aspects 101-111, wherein the second crosslinking initiator is added as a separate solvent dispersion of the second crosslinking initiator.

Aspect 113: The method of Aspect 112, the separate solvent dispersion comprises water, ethanol, or a combination thereof.

Aspect 114: The method of any one of Aspects 101-113, wherein the first and the second crosslinking initiators have a synergistic effect.

Aspect 115: The method of any one of Aspects to 93-114, wherein a gel time needed to form the hydrogel or the organogel is from about 500 s to less than about 10 s.

Aspect 116: The method of any one of Aspects 101-115, wherein a crosslinking rate is substantially higher when compared to a substantially identical reference method in the absence of the metal oxide.

Aspect 117: The method of any one of Aspects 101-116, wherein the step of crosslinking comprises: metal oxide initiated crosslinking via coupling of catechol groups of the polymer composition, formation of a metal complex with the catechol groups of the polymer composition, bonding metal oxide via hydrogen bonds or surface bonds with carboxyl groups or catechol groups of the polymer composition; or any combination thereof.

Aspect 118: The method of any one of Aspects 93-117, wherein the formed crosslinked composition comprises a sol content less than about 25%.

Aspect 119: The method of any one of Aspects 93-118, wherein the formed crosslinked composition exhibits a swelling ratio of less than about 200%.

Aspect 120: The method of any one of Aspects 93-119, wherein the formed crosslinked composition exhibits a tensile strength from about 1 to about 10 MPa in a dry state as measured according to ASTM D412A.

Aspect 121: The method of any one of Aspects 93-120, wherein the formed crosslinked composition exhibits an elongation at break from about 18% to about 150% a dry state as measured according to ASTM D412A.

Aspect 122: The method of any one of Aspects 93-121, wherein the formed crosslinked composition exhibits a modulus from about 1 to about 10 MPa in a dry state as measured according to ASTM D412A.

Aspect 123: The method of any one of Aspects 93-122, wherein the formed crosslinked composition exhibits a lap shear strength of greater than 30 kPa as measured according to a modified ASTM D1002-05 method.

Aspect 124: The method of any one of Aspects 93-123, wherein the formed crosslinked composition exhibits a higher cytocompatibility as measured against human mesenchymal stem cells when compared to a substantially identical reference composition with an absence of the metal oxide.

Aspect 125: The method of any one of Aspects 101-124, wherein the formed crosslinked composition exhibits an increased inhibition against *S. aureus* and *E. coli* when compared to a substantially identical reference composition in the absence of the metal oxide.

Aspect 126: The method of any one of Aspects 93-125, further comprising adding at least one pharmaceutically active component to the formed crosslinked composition.

Aspect 127: The method of any one of Aspects 93-126, wherein the formed crosslinked composition is a wound closing composition.

Aspect 128: A method of adhering a biological tissue, comprising: a) disposing the crosslinked composition of any one of Aspects 59-92 between a first portion of biological tissue and a second portion of biological tissue; and b) contacting the first portion of biological tissue with the second portion of biological tissue.

Aspect 129: A method of treating disease, comprising disposing the composition of Aspect 84, within the biological body, wherein the at least one pharmaceutically active component is active towards the disease and is configured to be released into the biological body at a predetermined time.

Aspect 130: A method of promoting a biological tissue growth comprising providing a scaffold comprising the composition of any one of Aspects 59-92 and disposing the scaffold in a tissue growth media.

Aspect 131: A kit for adhering a biological tissue comprising the crosslinked composition of any one of Aspects 59-92.

Aspect 132: A method of delivering at least one pharmaceutically active component in an efficient amount wherein the method comprises: a) incorporating the at least one pharmaceutically active component into a composition comprising: i) a polymerization product of one or more monomers of Formula (I) and one or more units of a block copolymer comprising one or more monomers of Formula (II), and/or Formula (II'), one or more monomers of Formula (III), and/or optionally one or more compounds of Formula (IV):

(I)

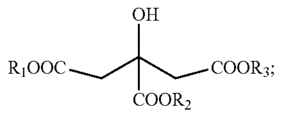

(II)

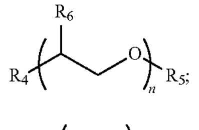

(II')

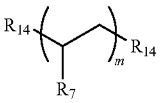

(III)

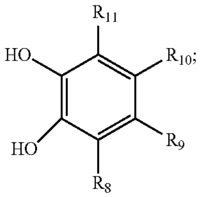

(IV)

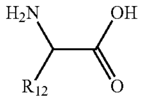

Wherein $R_1$, $R_2$, and $R_3$ are, independently, selected from hydrogen, $C_1$-$C_{22}$ alkyl group; wherein each of $R_1$, $R_2$, and $R_3$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_4$ is selected from hydrogen, a hydroxyl group, amine, alkoxyl group, $C_1$-$C_{22}$ alkyl group; $R_5$ is selected from hydrogen, amine, a hydroxyl group, or a $C_1$-$C_{22}$ alkyl group; $R_6$ is selected from hydrogen, a $C_1$-$C_{22}$ alkyl group, $C_2$-$C_{22}$ alkenyl group; $R_7$ is selected from hydrogen, amine, a hydroxyl group, alkoxyl group, a $C_1$-$C_{22}$ alkyl group; wherein each of $R_4$, $R_5$, $R_6$, and $R_7$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, phosphonyl; $R_8$, $R_9$, $R_{10}$, and $R_{11}$ are, independently, selected from hydrogen, hydroxyl, $C_1$-$C_{22}$ alkyl group, $C_1$-$C_{22}$ alkoxy group, amino group, halide, —SH— group, or a carboxyl group, wherein any of $R_8$, $R_9$, $R_{10}$, and $R_{11}$, are optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl; and wherein at least one of $R_8$, $R_9$, $R_{10}$, and $R_{11}$ comprises at least one nucleophilic group selected from —N(H)—, —O—, —COO—, —Cl, —F; and —S(O)—, —S—; and wherein at least one of the nucleophilic groups is a terminal group; n and m, are independently integers from 1 to 20; $R_{12}$ is an amino acid side chain; $R_{14}$ is —OH or —$NH_2$; and wherein the polymerization product does not comprise metal cations; and ii) a first crosslinking initiator having a formula $A_{b''}O_{a'}$, wherein A is a monovalent, divalent, or trivalent metallic cation and wherein a' and b" are dependent on the valency of A; wherein A is not a transition metal cation and wherein the first crosslinking initiator is configured to crosslink the reaction product to form the crosslinked composition; and wherein the crosslinked composition is a polymer network having at least one crosslink comprising two catechol moieties directly and covalently coupled to each other; wherein the crosslinked composition is a hydrogel or an organogel and is an adhesive composition; b) releasing the at least one pharmaceutical agent into a biological body at a predetermined time.

Aspect 133: The method of Aspect 132, wherein $R_1$, $R_2$, and $R_3$ are, independently, selected from hydrogen, —$CH_3$ group, or —$CH_2CH_3$ group; $R_4$ is selected from hydrogen, a hydroxyl group, —$NH_2$, —$OCH_3$, —$OCH_2CH_3$, —$CH_3$, —$CH_2CH_3$ group; a $C_3$ to $C_{22}$ alkyl or alkenyl group, —$CH_2CH_2OH$, or —$CH_2CH_2NH_2$; $R_6$ is hydrogen, a hydroxyl group, —$NH_2$, —$CH_3$, or —$CH_2CH_3$ group, a $C_3$ to $C_{22}$ alkyl or alkenyl group, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$; $R_7$ is selected from hydrogen or —$CH_3$ group; $R_8$, $R_9$, $R_{10}$, and $R_{11}$ are, independently, selected from hydrogen, —$CH_2(CH_2)_xNH_2$, —$CH_2(CHR_{13})NH_2$, or —$CH_2(CH_2)_xCOOH$ groups; and wherein at least one of $R_8$, $R_9$, $R_{10}$, and $R_{11}$ is not hydrogen; $R_{13}$ is —COOH or —$(CH_2)_yCOOH$ group; n and m, are independently integers from 1 to 20; x is an integer from 0 to 20; and y is an integer from 1 to 20.

Aspect 134: The method of any one of Aspects 132-133, wherein the block copolymer comprises repeating units of two or more monomers of Formula (II);

(II)

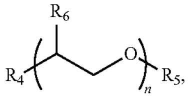

wherein $R_4$ is selected from hydrogen, a hydroxyl group, —$NH_2$, —$CH_2CH_2OH$, or —$CH_2CH_2NH_2$; $R_5$ is hydrogen, a hydroxyl group, —$NH_2$, —$CH_2CH_2OH$, or —$CH_2CH_2NH_2$; $R_6$ is selected from hydrogen, —$CH_3$ group, or —$CH_2CH_3$ group; —$CH_2CH_2OH$, or —$CH_2CH_2NH_2$.

Aspect 135: The method of Aspect 134, wherein the block copolymer has a formula (V) or formula (V'):

(V)

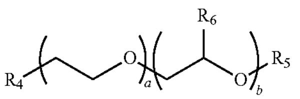

(V')

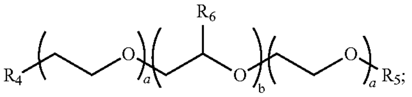

wherein a and b are independently chosen from n=1-20, and wherein $R_6$ is not hydrogen.

Aspect 136: The method of any one of Aspects 132-135, wherein the monomer of Formula (III) comprises dopamine of L-DOPA.

Aspect 137: The method of any one of aspects 132-136, wherein the polymerization product comprises:

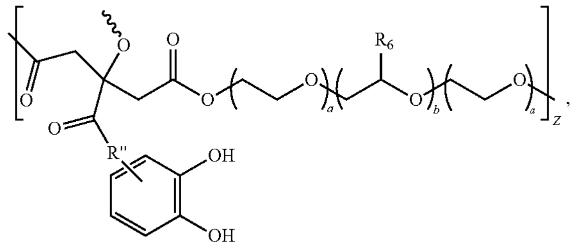

wherein R" is —$N(H)R_{15}$, or —$O(CO)(R_{15})$, or —$O(R_{15})$; wherein $R_{15}$ is independently selected from $C_1$-$C_{22}$ alkyl group, optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl groups; wherein $R_6$ is not hydrogen; wherein  defines a bond to hydrogen, or optionally to a predetermined polymer chain if present; wherein a and b are independently chosen from n=1-20, and wherein z=1-100.

REFERENCES

D. A. Hickman, C. L. Pawlowski, U. D. S. Sekhon, J. Marks, A S Biomaterials and advanced technologies for hemostatic management of bleeding, Adv. Mater. 30 (4) (2018) 1700859-1700899.

D. Xie, J. Guo, M. R. Mehdizadeh, R. T. Tran, R. Chen, D. Sun, G. Qian, D. Jin, X. Bai, J. Yang, Development of injectable citrate-based bioadhesive bone implants, J. Mater. Chem. B. 3 (2015) 387-398.

[A. P. Duarte, J. F. Coelho, J. C. Bordado, M. T. Cidade, M. H. Gil, Surgical adhesives: Systematic review of the main types and development forecast, Prog. Polym. Sci. 37 (8) (2012) 1031-1050.

J. Li, A. D. Celiz, J. Yang, Q. Yang, I. Wamala, W. Whyte, B. R. Seo, N. V. Vasilyev, J. J. Vlassak, Z. Suo, D. J. Mooney, Tough adhesives for diverse wet surfaces, Science 357 (6349) (2017) 378-381.

[J. Guo, W. Sun, J. P. Kim, X. Lu, Q. Li, M. Lin, O. Mrowczynski, E. B. Rizk, J. Cheng, G. Qian, J. Yang, Development of tannin-inspired antimicrobial bioadhesives, Acta Biomater. 72 (2018) 35-44.

N. Annabi, K. Yue, A. Tamayol, A. Khademhosseini, Elastic sealants for surgical applications, Eur. J. Pharm. Biopharm. 95 (2015) 27-39.

T. Fattahi, M. Mohan, G. T. Caldwell, Clinical applications of fibrin sealants, J. Oral. Maxillofac. Surg. 62 (2) (2004) 218-224.

J. L. Lim, W. K. Lee, Enhanced biocompatibility and adhesive properties by aromatic amino acid-modified allyl 2-cyanoacrylate-based bio-glue, Colloid. Surface B. 122 (2014) 669-673.

J. R. Dusick, C. A. Mattozo, F. Esposito, D. F. Kelly, BioGlue for prevention of postoperative cerebrospinal fluid leaks in transsphenoidal surgery: A case series, Surg. Neurol. 66 (2006) 371-376.

W. Furst, A. Banerjee, Conflict of interest disclosure relating to "Release of glutaraldehyde from an albumin-glutaraldehyde tissue adhesive causes significant in vitro and in vivo toxicity, Ann. Thorac. Surg. 79 (2005) 1522-1528.

E. J. Beckman, M. Buckley, S. Agarwal, J. Zhang, U.S. Pat. No. 7,264,823B2 (2007).

P J M Bouten, M. Zonjee, J. Bender, S. T. K. Yauw, H. van Goor, J C M van Hest, R. Hoogenboom, The chemistry of tissue adhesive materials, Prog. Polym. Sci. 39 (7) (2014) 1375-1405.

G. Lee, C. K. Lee, M. Bynevelt, DuraSeal-hematoma: concealed hematoma causing spinal cord compression, Spine 35 (25) (2010) E1522-E1524.

R. Wang, J. Li, W. Chen, T. Xu, S. Yun, Z. Xu, Z. Xu, T. Sato, B. Chi, H. Xu, A biomimetic mussel-inspired ε-poly-L-lysine hydrogel with robust tissue-anchor and anti-infection capacity, Adv. Funct. Mater. 27 (8) (2017) 1604894-1604907.

M. Mehdizadeh, H. Weng, D. Gyawali, L. Tang, J. Yang, Injectable citrate-based mussel-inspired tissue bioadhesives with high wet strength for sutureless wound closure, Biomaterials 33 (32) (2012) 7972-7983.

J. Guo, W. Wang, J. Hu, D. Xie, E. Gerhard, M. Nisic, D. Shan, G. Qian, S. Zheng, J. Yang, Synthesis and characterization of antibacterial and anti-fungal citrate-based mussel-inspired bioadhesives, Biomaterials 85 (2016) 204-217.

J. Guo, G. B. Kim, D. Shan, J. P. Kim, J. Hu, W. Wang, F. G. Hamad, G. Qian, E. B. Rizk, J. Yang, Click chemistry improved wet adhesion strength of mussel-inspired citrate-based antimicrobial bioadhesives, Biomaterials 112 (2017) 275-286.

Y. Liu, H. Meng, Z. Qian, N. Fan, W. Choi, F. Zhao, B. P. Lee, A moldable nanocomposite hydrogel composed of a mussel-inspired polymer and a nanosilicate as a fit-to-shape tissue sealant, Angew. Chem. Int. Ed. 56 (15) (2017) 4224-4228.

Z. Gu, S. Li, F. Zhang, S. Wang, Understanding surface adhesion in nature: A peeling model, Adv. Sci. 3 (7) (2016) 1500327-1500340.

D. G. Barrett, G. G. Bushnell, P. B. Messersmith, Mechanically robust, negative-swelling, mussel-inspired tissue adhesives, Adv. Healthcare Mater. 2 (5) (2013) 745-755.

C. Ma, X. Tian, J. P. Kim, D. Xie, X. Ao, D. Shan, Q. Lin, M. R. Hudock, X. Bai, J. Yang, Citrate-based materials fuel human stem cells by metabonegenic regulation, Proc. Natl. Acad. Sci. U.S.A 115 (50) (2018) E11741-E11750.

D. Shan, S.-R. Kothapalli, D. J. Ravnic, E. Gerhard, J. P. Kim, J. Guo, C. Ma, J. Guo, L. Gui, L. Sun, D. Lu, J. Yang, Development of citrate-based dual-imaging enabled biodegradable electroactive polymers, Adv. Funct. Mater. 28 (34) (2018) 1801787.

J. Guo, Z. Xie, R. T. Tran, D. Xie, D. Jin, X. Bai, J. Yang, Click chemistry plays a dual role in biodegradable polymer design. Adv. Mater. 26 (12) (2014) 1906-1911.

K. Sannier, A. Dompmartin, J. Théron, D. Labbé, M. T. Barrellier, R. Leroyer, P. Touré, D. Leroy, A new sclerosing agent in the treatment of venous malformations. Study on cases, Interv. Neuroradiol. 10 (2) (2004) 113-127.

M. M. Smith, M. P. Lin, R. V. Hovsepian, D. Wood, T. Nguyen, G. R. D. Evans, G. A. Wirth, Postoperative seroma formation after abdominoplasty with placement of continuous infusion local anesthetic pain pump, Can. J. Plast. Surg. 17 (4) (2009) 127-129.

L. Cárdenas-Camarena, L. E. González, Large-volume liposuction and extensive abdominoplasty: a feasible alternative for improving body shape, Plast. Reconstr. Surg. (5) (1998) 1698-1707.

D. J. Hickey, B. Ercan, L. Sun, T. J. Webster, Adding MgO nanoparticles to hydroxyapatite-PLLA nanocomposites for improved bone tissue engineering applications, Acta Biomater. 14 (2015) 175-184.

O. Yamamotoa, T. Ohira, K. Alvarez, M. Fukuda, Antibacterial characteristics of $CaCO_3$—MgO composites, Mater. Sci. Eng. B. 173 (1-3) (2010) 208-212.

Y. Rao, W. Wang, F. Tan, Y. Cai, J. Lu, X. Qiao, Influence of different ions doping on the antibacterial properties of MgO nanopowders, Appl. Surf. Sci. 284 (2013) 726-731.

S. Sakai, K. Hirose, K. Taguchi, Y. Ogushi, K. Kawakami, An injectable, in situ enzymatically gellable, gelatin derivative for drug delivery and tissue engineering, Biomaterials 30 (20) (2009) 3371-3377.

B. P. Lee, J. L. Dalsin, P. B. Messersmith, Synthesis and gelation of DOPA-modified poly(ethylene glycol) hydrogels, Biomacromolecules 3 (5) (2002) 1038-1047.

L. C. Su, Z. Xie, Y. Zhang, K. T. Nguyen, J. Yang, Study on the Antimicrobial Properties of Citrate-Based Biodegradable Polymers, Front. Bioeng. Biotechnol. 2 (2014) 23.

N A. Vasil'eva, L. M. Plyasova, G. V. Odegova, Defective magnesium oxides with oxygen-containing anion fragments incorporated in the oxide structure, Kinet. Catal. (6) (2009) 816-818.

Z.-X. Tang, B.-F. Lv, MgO nanoparticles as antibacterial agent: preparation and activity, Braz. J. Eng Chem. 31 (3) (2014) 591-601.

M. Mittal, M. R. Siddiqui, K. Tran, S. P. Reddy, A. B. Malik, Reactive oxygen species in inflammation and tissue injury. Antioxid.Redox Sign. 20 (2014) 1126-1167.

S. Xu, A. D. Chisholm1, *C. Elegans* epidermal wound induces a mitochondrial ROS burst that promotes wound repair. Dev. Cell 31 (2014) 48-60.

D. Gyawali, P. Nair, Y. Zhang, R. T. Tran, C. Zhang, M. Samchukov, M. Makarov, H. K. Kim, J. Yang, Citric acid-derived in situ crosslinkable biodegradable polymers for cell delivery, Biomaterials 31 (34) (2010) 9092-9105.

F. Sekiya, M, Yoshida, T. Yamashita, Magnesium(II) is a crucial constituent of the blood coagulation cascade. Potentiation of coagulant activities of factor IX by $Mg^{2+}$ ions, J. Biol. Chem. 271 (15) (1996) 8541-8544.

AMHP van den Besselaar, Magnesium and manganese ions accelerate tissue factor-induced coagulation independently of factor IX, Blood Coagul. Fibrinolysis. 13 (1) (2002) 19-23.

E. M. Liotta, S. Prabhakaran, R. S. Sangha, R. A. Bush, A. E. Long, S. A. Trevick, M. B. Potts, B. S. Jahromi, M. Kim, E. M. Manno, F. A. Sorond, A. M. Naidech, M. B. Maas, Magnesium, hemostasis, and outcomes in patients with intracerebral hemorrhage, Neurology 89 (8) (2017) 813-819.

What is claimed is:

1. A crosslinked composition comprising:

a) a polymerization product of:

one or more monomers of Formula (I), one or more units of a block copolymer of Formula (V) or Formula (V'), one or more monomers of Formula (III), and optionally one or more compounds of Formula (IV):

(I)

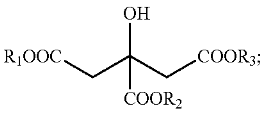

(V)

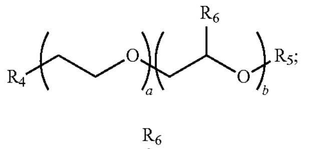

(V')

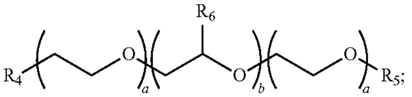

(III)

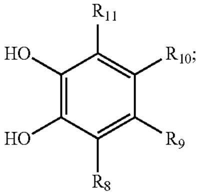

and (IV)

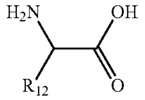

wherein $R_1$, $R_2$, and $R_3$ are, independently, selected from hydrogen, —$CH_3$, and $CH_2CH_3$;

$R_4$ is selected from hydrogen, a hydroxyl group, —$NH_2$, —$OCH_3$, —$OCH_2CH_3$, —$CH_3$, —$CH_2CH_3$, a $C_3$ to $C_{22}$ alkyl or alkenyl group, —$CH_2CH_2OH$, and —$CH_2CH_2NH_2$;

$R_5$ is selected from hydrogen, a hydroxyl group, —$NH_2$, —$CH_3$, —$CH_2CH_3$, a $C_3$ to $C_{22}$ alkyl or alkenyl group, —$CH_2CH_2OH$, and —$CH_2CH_2NH_2$;

$R_6$ is selected from —$CH_3$, —$CH_2CH_3$, —$CH_2CH_2OH$, and —$CH_2CH_2NH_2$;

$R_8$, $R_9$, $R_{10}$, and $R_{11}$ are, independently, selected from hydrogen, —$CH_2$ $(CH_2)_xNH_2$, —$CH_2$ $(CHR_{13})$ $NH_2$, and —$CH_2$ $(CH_2)_xCOOH$ groups; wherein at least one of $R_8$, $R_9$, $R_{10}$, and $R_{11}$ is not hydrogen;

$R_{12}$ is an amino acid side chain;

$R_{13}$ is —COOH or —$(CH_2)_yCOOH$;

x is an integer from 0 to 20;

y is an integer from 1 to 20; and a and b are independently chosen from n=1-20;

wherein the polymerization product does not comprise metal cations; and b) a first crosslinking initiator having a formula $A_{b'}O_{a'}$, wherein A is a monovalent, divalent, or trivalent metallic cation and wherein a' and b' are dependent on the valency of A; wherein A is not a transition metal cation and wherein the first crosslinking initiator is configured to crosslink the polymerization product to form the crosslinked composition; and wherein the crosslinked composition is a polymer network having at least one crosslink comprising two catechol moieties directly and covalently coupled to each other; and wherein the crosslinked composition is a hydrogel or an organogel and is an adhesive composition.

2. The crosslinked composition of claim 1, wherein the monomer of Formula (III) comprises dopamine or L-DOPA.

3. The crosslinked composition of claim 1, wherein the polymerization product comprises:

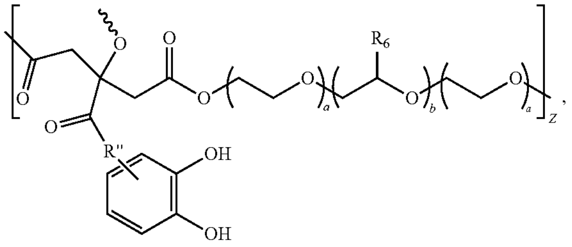

wherein R" is —$N(H)R_{15}$, or —$O(CO)(R_{15})$, or —$O(R_{15})$; wherein $R_{15}$ is independently selected from $C_1$-$C_{22}$ alkyl group, optionally substituted with $C_1$-$C_{22}$ alkyl, $C_1$-$C_{22}$ alkoxy, $C_2$-$C_{22}$ alkenyl, $C_2$-$C_{22}$ alkynyl, $C_6$-$C_{14}$ aryl, $C_1$-$C_{13}$ heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl groups;

wherein $R_6$ is not hydrogen;

wherein ∿∿∿ defines a bond to hydrogen, or optionally to a predetermined polymer chain if present;

wherein a and b are independently chosen from n=1-20, and wherein z=1-100.

4. The crosslinked composition of claim 1, wherein the first crosslinking initiator simultaneously behaves as a first filler.

5. The crosslinked composition of claim 4, further comprising an additional filler that is different from the first filler.

6. The crosslinked composition of claim 1, further comprising a second crosslinking initiator that is different from the first crosslinking initiator.

7. The crosslinked composition of claim 6, wherein the second crosslinking initiator comprises sodium periodate, silver nitrate, or ferric chloride, or any combination thereof.

8. The crosslinked composition of claim 1, wherein the first crosslinking initiator is a metal oxide selected from magnesium oxide, calcium oxide, zinc oxide, barium oxide, cesium oxide, or any combination thereof.

9. The crosslinked composition of claim 1, wherein the compound of Formula (IV) is present in the polymerization product.

10. The crosslinked composition of claim 1, wherein the crosslinked composition comprises a sol content less than about 25%.

11. The composition of claim 1, further comprising at least one pharmaceutically active component.

12. A method of treating disease, comprising disposing the composition of claim 11, within the biological body, wherein the at least one pharmaceutically active component is active towards the disease and is configured to be released into the biological body at a predetermined time.

13. The composition of claim 1, wherein the composition is a wound closing composition.

14. A method of making a composition of claim 1, comprising:

a) reacting a polycarboxylic acid of one or more monomers of Formula (I)

(I)

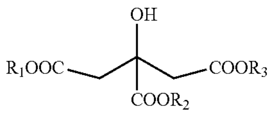

with one or more units of a block copolymer of Formula (V) or Formula (V'), (V)

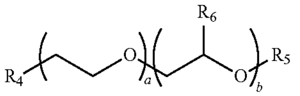

(V')

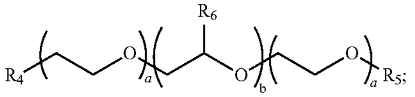

and with a compound of one or more monomers of Formula (III)

(III)

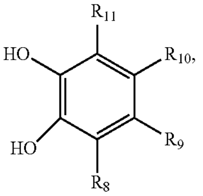

and optionally with one or more compounds of Formula (IV)

(IV)

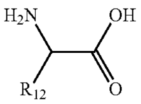

at conditions effective to form a prepolymer composition configured to be crosslinked; wherein $R_1$, $R_2$, and $R_3$ are, independently, selected from hydrogen, $-CH_3$, and $CH_2CH_3$;

$R_4$ is selected from hydrogen, a hydroxyl group, $-NH_2$, $-OCH_3$, $-OCH_2CH_3$, $-CH_3$, $-CH_2CH_3$, a $C_3$ to $C_{22}$ alkyl or alkenyl group, $-CH_2CH_2OH$, and $-CH_2CH_2NH_2$;

$R_5$ is selected from hydrogen, a hydroxyl group, $-NH_2$, $-CH_3$, $-CH_2CH_3$, a $C_3$ to $C_{22}$ alkyl or alkenyl group, $-CH_2CH_2OH$, and $-CH_2CH_2NH_2$;

$R_6$ is selected from $-CH_3$, $-CH_2CH_3$, $-CH_2CH_2OH$, and $-CH_2CH_2NH_2$;

$R_8$, $R_9$, $R_{10}$, and $R_{11}$ are, independently, selected from hydrogen, $-CH_2(CH_2)_xNH_2$, $-CH_2(CHR_{13})NH_2$, and $-CH_2(CH_2)_xCOOH$ groups; wherein at least one of $R_8$, $R_9$, $R_{10}$, and $R_{11}$ is not hydrogen $R_{12}$ is an amino acid side chain;

$R_{13}$ is $-COOH$ or $-(CH_2)_yCOOH$;

x is an integer from 0 to 20;

y is an integer from 1 to 20; and a and b are independently chosen from n=1-20;

wherein the prepolymer composition does not comprise metal cations;

b) adding a first crosslinking initiator to the prepolymer composition; wherein the first crosslinking initiator has a formula AbBa, wherein A is a monovalent, divalent, or trivalent metallic cation and B is an anion, and wherein a and b are defined by the valency of A and B; wherein A is not a transition metal cation and c) crosslinking the prepolymer composition to form a crosslinked composition comprising a polymer network, wherein at least one crosslink in the crosslinked polymer comprises two catechol moieties directly and covalently coupled to each other; and wherein the crosslinked composition is a hydrogel or organogel and is adhesive.

15. The method of claim 14, wherein a gel time needed to form the hydrogel or the organogel is from about 500 s to less than about 10 s.

16. A method of adhering a biological tissue, comprising:

a) disposing the crosslinked composition of claim 1 between a first portion of biological tissue and a second portion of biological tissue; and b) contacting the first portion of biological tissue with the second portion of biological tissue.

17. A method of delivering at least one pharmaceutically active component in an efficient amount wherein the method comprises:

incorporating the at least one pharmaceutically active component into a crosslinked composition of claim 1; and b) releasing the at least one pharmaceutical agent into a biological body at a predetermined time.

18. A method of promoting biological tissue growth comprising providing a scaffold comprising the composition of claim 1 and disposing the scaffold in a tissue growth media.

19. A crosslinked composition formed by a) forming a polymerization product by reacting one or more monomers of Formula (I) with:

a block copolymer of Formula (V) or Formula (V'), one or more monomers of Formula (III), and optionally one or more compounds of Formula (IV):

(I)

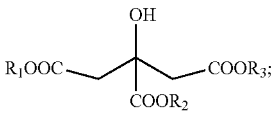

(V)

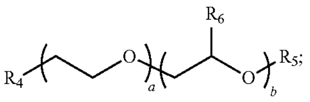

-continued (V')

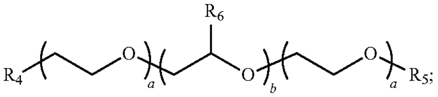

(III)

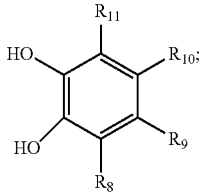

and (IV)

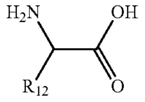

wherein $R_1$, $R_2$, and $R_3$ are, independently, selected from hydrogen, —$CH_3$, and —$CH_2CH_3$;

$R_4$ is selected from hydrogen, a hydroxyl group, —$NH_2$, —$OCH_3$, —$OCH_2CH_3$, —$CH_3$, —$CH_2CH_3$, a $C_3$ to $C_{22}$ alkyl or alkenyl group, —$CH_2CH_2OH$, and —$CH_2CH_2NH_2$;

$R_5$ is selected from hydrogen, a hydroxyl group, —$NH_2$, —$CH_3$, —$CH_2CH_3$, a $C_3$ to $C_{22}$ alkyl or alkenyl group, —$CH_2CH_2OH$, and —$CH_2CH_2NH_2$;

$R_6$ is selected from —$CH_3$, —$CH_2CH_3$, —$CH_2CH_2OH$, and —$CH_2CH_2NH_2$;

$R_8$, $R_9$, $R_{10}$, and $R_{11}$ are, independently, selected from $R_{12}$ is an amino acid side chain;

$R_{13}$ is —COOH or —$(CH_2)_y$COOH;

x is an integer from 0 to 20;

y is an integer from 1 to 20; and a and b are independently chosen from n=1-20;

wherein the polymerization product does not comprise metal cations;

b) crosslinking the polymerization product with a first crosslinking initiator having a formula $A_{b'}O_{a'}$, wherein A is a monovalent, divalent, or trivalent metallic cation and wherein a' and b' are defined by the valency of A; wherein A is not a transition metal cation;

wherein the crosslinked composition is a polymer network having at least one crosslink comprising two catechol moieties directly and covalently coupled to each other; and wherein the crosslinked composition is a hydrogel or organogel and is an adhesive composition.

* * * * *